US012681658B2

(12) United States Patent
Dicks et al.

(10) Patent No.: US 12,681,658 B2
(45) Date of Patent: *Jul. 14, 2026

(54) HEALTH MONITORING AND COMMUNICATIONS DEVICE

(71) Applicant: Life365, Inc., Scottsdale, AZ (US)

(72) Inventors: Kent Dicks, Scottsdale, AZ (US); Eric Vandewater, Scottsdale, AZ (US); Randolph Strength, Scottsdale, AZ (US)

(73) Assignee: Life365, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/084,188

(22) Filed: Mar. 19, 2025

(65) Prior Publication Data

US 2025/0244906 A1 Jul. 31, 2025

Related U.S. Application Data

(63) Continuation of application No. 17/897,047, filed on Aug. 26, 2022, which is a continuation of application (Continued)

(51) Int. Cl.
*G06F 3/06* (2006.01)
*G06F 9/445* (2018.01)
(Continued)

(52) U.S. Cl.
CPC .......... *G06F 3/0643* (2013.01); *G06F 3/0616* (2013.01); *G06F 3/0625* (2013.01);
(Continued)

(58) Field of Classification Search
CPC ..... A61B 5/681; A61B 5/6801; A61B 5/6802; A61B 5/02438; A61B 5/01;
(Continued)

(56) References Cited

U.S. PATENT DOCUMENTS 3,755,630 A 8/1973 Boyer
4,550,370 A 10/1985 Baker
(Continued)

FOREIGN PATENT DOCUMENTS

AU 2002100889 A4 6/2003
WO 0049549 A1 8/2000
(Continued)

OTHER PUBLICATIONS

Mell et al., "The NIST Definition of Cloud Computing," National Institute of Standards and Technology (U.S. Department of Commerce), Special Publication 800-145, 7 pages (Sep. 2011).

(Continued)

*Primary Examiner* — Xuxing Chen
(74) *Attorney, Agent, or Firm* — Snell & Wilmer L.L.P.

(57) ABSTRACT

Devices, systems, and methods for reconfigurable and/or updatable lightweight electronic devices or systems are disclosed. Via use of such a device, system, or method, various capabilities for a user are provided, simplified, secured, and/or made more convenient. The system may interact with various other devices or systems, including those that are cloud-based or communicate through the cloud, and may utilize various local sensors, in order to provide one or more of improved access, monitoring, user diagnostics, and so forth.

20 Claims, 15 Drawing Sheets

Related U.S. Application Data

No. 17/110,347, filed on Dec. 3, 2020, now abandoned, which is a continuation of application No. 16/203,143, filed on Nov. 28, 2018, now Pat. No. 10,942,664, which is a continuation of application No. 15/256,137, filed on Sep. 2, 2016, now Pat. No. 10,185,513, which is a continuation-in-part of application No. 15/188,740, filed on Jun. 21, 2016, now abandoned, which is a continuation of application No. 15/174,632, filed on Jun. 6, 2016, now abandoned.

(60) Provisional application No. 62/264,179, filed on Dec. 7, 2015, provisional application No. 62/213,513, filed on Sep. 2, 2015, provisional application No. 62/171,944, filed on Jun. 5, 2015.

(51) Int. Cl.

| | |
|---|---|
| *G06Q 20/10* | (2012.01) |
| *G06Q 20/14* | (2012.01) |
| *G06Q 20/32* | (2012.01) |
| *G06Q 20/34* | (2012.01) |
| *G06Q 30/0601* | (2023.01) |
| *G07F 9/00* | (2006.01) |
| *G07F 19/00* | (2006.01) |
| *G07G 1/00* | (2006.01) |
| *G16H 40/63* | (2018.01) |
| *H04L 67/10* | (2022.01) |

(52) U.S. Cl.
CPC ............ *G06F 3/064* (2013.01); *G06F 3/0679* (2013.01); *G06F 9/44505* (2013.01); *G06Q 20/108* (2013.01); *G06Q 20/14* (2013.01); *G06Q 20/3226* (2013.01); *G06Q 20/3552* (2013.01); *G06Q 20/356* (2013.01); *G06Q 30/0635* (2013.01); *G07F 9/006* (2013.01); *G07F 19/206* (2013.01); *G07G 1/0009* (2013.01); *G16H 40/63* (2018.01); *H04L 67/10* (2013.01)

(58) Field of Classification Search
CPC .............. A61B 5/02405; A61B 5/0816; A61B 5/02055; A61B 5/256; A61N 1/3925; G16H 10/60; G16H 15/00; G16H 20/30
See application file for complete search history.

(56) References Cited

U.S. PATENT DOCUMENTS

| | | | |
|---|---|---|---|
| 5,006,699 | A | 4/1991 | Felkner et al. |
| 5,404,485 | A | 4/1995 | Ban |
| 5,673,692 | A | 10/1997 | Schulze et al. |
| 5,721,780 | A | 2/1998 | Ensor et al. |
| 5,724,985 | A | 3/1998 | Snell et al. |
| 5,772,586 | A | 6/1998 | Heinonen et al. |
| 5,891,180 | A | 4/1999 | Greeninger et al. |
| 5,936,523 | A | 8/1999 | West |
| 6,024,699 | A | 2/2000 | Surwit et al. |
| 6,034,963 | A | 3/2000 | Minami et al. |
| 6,093,146 | A | 7/2000 | Filangeri |
| 6,302,844 | B1 | 10/2001 | Walker et al. |
| 6,336,900 | B1 | 1/2002 | Alleckson et al. |
| 6,402,691 | B1 | 6/2002 | Peddicord et al. |
| 6,416,471 | B1 | 7/2002 | Kumar et al. |
| 6,443,890 | B1 | 9/2002 | Schulze et al. |
| 6,443,891 | B1 | 9/2002 | Grevious |
| 6,478,736 | B1 | 11/2002 | Mault |
| 6,485,418 | B2 | 11/2002 | Yasushi et al. |
| 6,579,231 | B1 | 6/2003 | Phipps |
| 6,580,948 | B2 | 6/2003 | Haupert et al. |
| 6,598,084 | B1 | 7/2003 | Edwards et al. |
| 6,625,642 | B1 | 9/2003 | Naylor et al. |
| 6,789,157 | B1 | 9/2004 | Lilja et al. |
| 6,790,178 | B1 | 9/2004 | Mault et al. |
| 6,804,558 | B2 | 10/2004 | Haller et al. |
| 6,807,965 | B1 | 10/2004 | Hickle |
| 6,893,396 | B2 | 5/2005 | Schulze et al. |
| 6,903,657 | B2 | 6/2005 | Kwoen |
| 6,915,267 | B2 | 7/2005 | Jackson et al. |
| 6,957,107 | B2 | 10/2005 | Rogers et al. |
| 6,970,969 | B2 | 11/2005 | Wong et al. |
| 6,978,182 | B2 | 12/2005 | Mazar et al. |
| 7,039,810 | B1 | 5/2006 | Nichols |
| 7,044,911 | B2 | 5/2006 | Drinan et al. |
| 7,129,836 | B2 | 10/2006 | Lawson et al. |
| 7,134,996 | B2 | 11/2006 | Bardy |
| 7,154,398 | B2 | 12/2006 | Chen et al. |
| 7,156,808 | B2 | 1/2007 | Quy |
| 7,161,484 | B2 | 1/2007 | Tsoukalis |
| 7,181,017 | B1 | 2/2007 | Nagel |
| 7,231,258 | B2 | 6/2007 | Moore et al. |
| 7,242,306 | B2 | 7/2007 | Wildman et al. |
| 7,265,676 | B2 | 9/2007 | Krause et al. |
| 7,311,666 | B2 | 12/2007 | Stupp et al. |
| 7,414,534 | B1 | 8/2008 | Kroll et al. |
| 7,438,216 | B2 | 10/2008 | Ambekar et al. |
| 7,590,191 | B1 | 9/2009 | Macrae |
| 7,598,878 | B2 | 10/2009 | Goldreich |
| 7,733,224 | B2 | 6/2010 | Tran |
| 7,761,261 | B2 | 7/2010 | Shmueli et al. |
| 7,953,873 | B1 | 5/2011 | Madurzak |
| 8,126,728 | B2 | 2/2012 | Dicks et al. |
| 8,126,729 | B2 | 2/2012 | Dicks et al. |
| 8,126,730 | B2 | 2/2012 | Dicks et al. |
| 8,126,731 | B2 | 2/2012 | Dicks et al. |
| 8,126,732 | B2 | 2/2012 | Dicks et al. |
| 8,126,733 | B2 | 2/2012 | Dicks et al. |
| 8,126,734 | B2 | 2/2012 | Dicks et al. |
| 8,126,735 | B2 | 2/2012 | Dicks et al. |
| 8,131,564 | B2 | 3/2012 | Dicks et al. |
| 8,131,565 | B2 | 3/2012 | Dicks et al. |
| 8,131,566 | B2 | 3/2012 | Dicks et al. |
| 8,140,356 | B2 | 3/2012 | Dicks et al. |
| 8,155,982 | B2 | 4/2012 | Dicks et al. |
| 8,209,195 | B2 | 6/2012 | Dicks et al. |
| 8,214,549 | B2 | 7/2012 | Dicks et al. |
| 8,398,546 | B2 | 3/2013 | Pacione et al. |
| 8,446,275 | B2 | 5/2013 | Utter, II et al. |
| 8,548,828 | B1 | 10/2013 | Longmire |
| 8,644,929 | B2 | 2/2014 | Diebold et al. |
| 8,677,054 | B1 | 3/2014 | Meir et al. |
| 8,725,843 | B2 | 5/2014 | Lockridge et al. |
| 8,734,296 | B1 | 5/2014 | Brumback et al. |
| 8,793,522 | B2 | 7/2014 | Rahman et al. |
| 8,825,428 | B2 | 9/2014 | Addison et al. |
| 8,830,913 | B1 | 9/2014 | Sosa et al. |
| 8,868,377 | B2 | 10/2014 | Yuen et al. |
| 8,886,576 | B1 | 11/2014 | Sanketi et al. |
| 8,909,543 | B2 | 12/2014 | Tropper et al. |
| 8,920,332 | B2 | 12/2014 | Hong et al. |
| 9,026,053 | B2 | 5/2015 | Molettiere et al. |
| 9,031,812 | B2 | 5/2015 | Roberts et al. |
| 9,042,971 | B2 | 5/2015 | Brumback et al. |
| 9,048,923 | B2 | 6/2015 | Molettiere et al. |
| 9,089,760 | B2 | 7/2015 | Tropper |
| 9,106,307 | B2 | 8/2015 | Molettiere et al. |
| 9,258,775 | B1 | 2/2016 | Sosa et al. |
| 9,443,263 | B1 | 9/2016 | Kim |
| 9,451,911 | B1 | 9/2016 | Mirov et al. |
| 9,871,575 | B2 | 1/2018 | Wengrovitz et al. |
| 9,974,492 | B1 | 5/2018 | Dicks et al. |
| 10,185,513 | B1 | 1/2019 | Vandewater |
| 10,388,411 | B1 | 8/2019 | Dicks et al. |
| 10,560,135 | B1 | 2/2020 | Dicks et al. |
| 2001/0005772 | A1 | 6/2001 | Kisakibaru |
| 2001/0051787 | A1 | 12/2001 | Haller et al. |
| 2002/0029157 | A1 | 3/2002 | Marchosky |
| 2002/0072933 | A1 | 6/2002 | Vonk et al. |
| 2002/0116698 | A1 | 8/2002 | Lurie et al. |
| 2002/0128804 | A1 | 9/2002 | Geva |
| 2003/0009088 | A1 | 1/2003 | Korth et al. |

(56)                  References Cited

U.S. PATENT DOCUMENTS

| | | |
|---|---|---|
| 2003/0018742 A1 | 1/2003 | Imago |
| 2003/0050539 A1 | 3/2003 | Naghavi et al. |
| 2003/0065805 A1 | 4/2003 | Barnes |
| 2003/0066065 A1 | 4/2003 | Larkin |
| 2003/0072424 A1 | 4/2003 | Evans et al. |
| 2003/0088295 A1 | 5/2003 | Cox |
| 2003/0088441 A1 | 5/2003 | Mcnerney |
| 2003/0095675 A1 | 5/2003 | Marlow et al. |
| 2003/0149593 A1 | 8/2003 | Mok et al. |
| 2003/0212632 A1 | 11/2003 | Keogh et al. |
| 2003/0216625 A1 | 11/2003 | Phipps |
| 2004/0015132 A1 | 1/2004 | Brown |
| 2004/0078220 A1 | 4/2004 | Jackson |
| 2004/0097796 A1 | 5/2004 | Berman et al. |
| 2004/0100376 A1 | 5/2004 | Lye et al. |
| 2004/0102683 A1 | 5/2004 | Khanuja et al. |
| 2004/0122488 A1 | 6/2004 | Mazar et al. |
| 2004/0127775 A1 | 7/2004 | Miyazaki et al. |
| 2004/0133080 A1 | 7/2004 | Mazar et al. |
| 2004/0152961 A1 | 8/2004 | Carlson et al. |
| 2004/0176983 A1 | 9/2004 | Birkett et al. |
| 2004/0199056 A1 | 10/2004 | Husemann et al. |
| 2004/0210458 A1 | 10/2004 | Evans et al. |
| 2005/0002341 A1 | 1/2005 | Lee et al. |
| 2005/0004700 A1 | 1/2005 | Dimaggio |
| 2005/0010911 A1 | 1/2005 | Kim et al. |
| 2005/0021370 A1 | 1/2005 | Riff et al. |
| 2005/0038680 A1 | 2/2005 | McMahon |
| 2005/0060187 A1 | 3/2005 | Gottesman |
| 2005/0065418 A1 | 3/2005 | Ginor |
| 2005/0065815 A1 | 3/2005 | Mazar et al. |
| 2005/0070767 A1 | 3/2005 | Maschke |
| 2005/0119580 A1 | 6/2005 | Eveland |
| 2005/0137465 A1 | 6/2005 | Cuddihy et al. |
| 2005/0149358 A1 | 7/2005 | Sacco et al. |
| 2005/0171410 A1 | 8/2005 | Hjelt et al. |
| 2005/0171762 A1 | 8/2005 | Ryan et al. |
| 2005/0192649 A1 | 9/2005 | Shehadeh et al. |
| 2005/0197545 A1 | 9/2005 | Hoggle |
| 2005/0203775 A1 | 9/2005 | Chesbrough |
| 2005/0216311 A1 | 9/2005 | Gmelin |
| 2005/0234307 A1 | 10/2005 | Heinonen et al. |
| 2005/0234742 A1 | 10/2005 | Hodgdon |
| 2005/0240111 A1 | 10/2005 | Chung |
| 2005/0251583 A1 | 11/2005 | Rothman et al. |
| 2005/0286306 A1 | 12/2005 | Srinivasan et al. |
| 2006/0020302 A1 | 1/2006 | Torgerson et al. |
| 2006/0026118 A1 | 2/2006 | Jung et al. |
| 2006/0035669 A1 | 2/2006 | Chuprun et al. |
| 2006/0036134 A1 | 2/2006 | Tarassenko et al. |
| 2006/0036802 A1 | 2/2006 | Drukin |
| 2006/0063980 A1 | 3/2006 | Hwang et al. |
| 2006/0064320 A1 | 3/2006 | Postrel |
| 2006/0080680 A1 | 4/2006 | Anwar et al. |
| 2006/0089542 A1 | 4/2006 | Sands |
| 2006/0106806 A1 | 5/2006 | Sperling et al. |
| 2006/0111079 A1 | 5/2006 | Tischer |
| 2006/0116744 A1 | 6/2006 | Von Arx et al. |
| 2006/0135858 A1 | 6/2006 | Nidd et al. |
| 2006/0142648 A1 | 6/2006 | Banet et al. |
| 2006/0161222 A1 | 7/2006 | Haubrich et al. |
| 2006/0167346 A1 | 7/2006 | Sarel |
| 2006/0200007 A1 | 9/2006 | Brockway et al. |
| 2006/0202816 A1 | 9/2006 | Crump et al. |
| 2006/0205564 A1 | 9/2006 | Peterson |
| 2006/0212316 A1 | 9/2006 | Jackson et al. |
| 2006/0218011 A1 | 9/2006 | Walker et al. |
| 2006/0235280 A1 | 10/2006 | Vonk et al. |
| 2006/0242295 A1 | 10/2006 | Husemann et al. |
| 2006/0247549 A1 | 11/2006 | Chan |
| 2006/0253301 A1 | 11/2006 | Simms et al. |
| 2006/0270421 A1 | 11/2006 | Phillips et al. |
| 2006/0293607 A1 | 12/2006 | Alt et al. |
| 2007/0002791 A1 | 1/2007 | Kasprzyk |
| 2007/0004969 A1 | 1/2007 | Kong et al. |
| 2007/0015974 A1 | 1/2007 | Higgins et al. |
| 2007/0016450 A1 | 1/2007 | Bhora et al. |
| 2007/0033072 A1 | 2/2007 | Bildirici |
| 2007/0055552 A1 | 3/2007 | St Clair et al. |
| 2007/0061167 A1 | 3/2007 | Brown |
| 2007/0073266 A1 | 3/2007 | Chmiel et al. |
| 2007/0078497 A1 | 4/2007 | Vandanacker |
| 2007/0083246 A1 | 4/2007 | Mazar et al. |
| 2007/0135855 A1 | 6/2007 | Foshee et al. |
| 2007/0143398 A1 | 6/2007 | Graham |
| 2007/0171076 A1 | 7/2007 | Stevens et al. |
| 2007/0188323 A1 | 8/2007 | Sinclair et al. |
| 2007/0239229 A1 | 10/2007 | Masoud et al. |
| 2007/0250130 A1 | 10/2007 | Ball et al. |
| 2007/0253380 A1 | 11/2007 | Jollota et al. |
| 2007/0267475 A1 | 11/2007 | Hoglund et al. |
| 2007/0276283 A1 | 11/2007 | Hung |
| 2008/0010088 A1 | 1/2008 | Ben-Attar et al. |
| 2008/0028879 A1 | 2/2008 | Robinette et al. |
| 2008/0059239 A1 | 3/2008 | Gerst et al. |
| 2008/0065412 A1 | 3/2008 | Vallone |
| 2008/0082968 A1 | 4/2008 | Chang et al. |
| 2008/0097910 A1 | 4/2008 | Dicks et al. |
| 2008/0126131 A1 | 5/2008 | Lou |
| 2008/0126742 A1 | 5/2008 | Shupak et al. |
| 2008/0129518 A1 | 6/2008 | Carlton-Foss |
| 2008/0221921 A1 | 9/2008 | Love et al. |
| 2008/0301158 A1 | 12/2008 | Brown et al. |
| 2009/0048865 A1 | 2/2009 | Breazeale |
| 2009/0058611 A1 | 3/2009 | Kawamura et al. |
| 2009/0099864 A1 | 4/2009 | Cronrath et al. |
| 2009/0112630 A1 | 4/2009 | Collins et al. |
| 2009/0113413 A1 | 4/2009 | Reinz |
| 2009/0138207 A1 | 5/2009 | Cosentino et al. |
| 2009/0150416 A1 | 6/2009 | Baker et al. |
| 2009/0172773 A1 | 7/2009 | Moore |
| 2009/0204434 A1 | 8/2009 | Breazeale |
| 2009/0233579 A1 | 9/2009 | Castell et al. |
| 2009/0249443 A1 | 10/2009 | Fitzgerald et al. |
| 2009/0299766 A1 | 12/2009 | Friedlander et al. |
| 2010/0007469 A1 | 1/2010 | Cardullo |
| 2010/0045425 A1 | 2/2010 | Chivallier |
| 2010/0299158 A1 | 11/2010 | Siegel et al. |
| 2011/0004574 A1 | 1/2011 | Jeong et al. |
| 2011/0093287 A1 | 4/2011 | Dicks et al. |
| 2011/0106227 A1 | 5/2011 | Desiderio et al. |
| 2011/0124310 A1 | 5/2011 | Theilmann et al. |
| 2011/0167110 A1 | 7/2011 | Hoffberg et al. |
| 2011/0179405 A1 | 7/2011 | Dicks et al. |
| 2012/0005445 A1 | 1/2012 | Escandell et al. |
| 2012/0102633 A1 | 5/2012 | Aulenbach |
| 2012/0109873 A1 | 5/2012 | Xiong et al. |
| 2012/0209657 A1 | 8/2012 | Connolly |
| 2012/0209749 A1 | 8/2012 | Hammad et al. |
| 2012/0265866 A1 | 10/2012 | Stanciu et al. |
| 2012/0266251 A1 | 10/2012 | Birtwhistle et al. |
| 2013/0041290 A1 | 2/2013 | Kording et al. |
| 2013/0066644 A1 | 3/2013 | Dicks et al. |
| 2013/0121116 A1 | 5/2013 | Lee |
| 2013/0132465 A1 | 5/2013 | Brown |
| 2013/0218588 A1 | 8/2013 | Kehr et al. |
| 2013/0226612 A1 | 8/2013 | Carmeli et al. |
| 2013/0290005 A1 | 10/2013 | Vesto et al. |
| 2014/0025398 A1 | 1/2014 | Ridgeway |
| 2014/0046391 A1 | 2/2014 | Cowan et al. |
| 2014/0052475 A1 | 2/2014 | Madan et al. |
| 2014/0142963 A1 | 5/2014 | Hill et al. |
| 2014/0239065 A1 | 8/2014 | Zhou et al. |
| 2014/0249658 A1 | 9/2014 | Curry |
| 2014/0257877 A1 | 9/2014 | L Heureux et al. |
| 2014/0273824 A1 | 9/2014 | Fenner et al. |
| 2014/0273858 A1 | 9/2014 | Panther et al. |
| 2014/0275852 A1 | 9/2014 | Hong et al. |
| 2014/0276244 A1 | 9/2014 | Kamyar |
| 2014/0278941 A1 | 9/2014 | Livingston et al. |
| 2014/0300490 A1 | 10/2014 | Kotz et al. |
| 2014/0316981 A1 | 10/2014 | Muthukrishnan et al. |
| 2014/0330654 A1 | 11/2014 | Turney et al. |

(56) References Cited

U.S. PATENT DOCUMENTS

| | | | | |
|---|---|---|---|---|
| 2014/0378777 A1* | 12/2014 | Conrad | ......... | A61N 2/002 |
| | | | | 600/301 |
| 2015/0058110 A1* | 2/2015 | Roth | ......... | G06Q 20/321 |
| | | | | 705/14.27 |
| 2015/0157274 A1 | 6/2015 | Ghassemzadeh et al. | | |
| 2015/0161331 A1 | 6/2015 | Oleynik | | |
| 2015/0172441 A1 | 6/2015 | Samhat | | |
| 2015/0173631 A1 | 6/2015 | Richards et al. | | |
| 2015/0182160 A1 | 7/2015 | Kim et al. | | |
| 2015/0185042 A1 | 7/2015 | Crawford et al. | | |
| 2015/0185762 A1 | 7/2015 | Magi | | |
| 2015/0228062 A1 | 8/2015 | Joshi et al. | | |
| 2015/0238692 A1 | 8/2015 | Peterson et al. | | |
| 2015/0289820 A1* | 10/2015 | Miller | ......... | A61B 5/681 |
| | | | | 600/300 |
| 2015/0305690 A1* | 10/2015 | Tan | ......... | A61B 5/02055 |
| | | | | 600/549 |
| 2015/0314681 A1* | 11/2015 | Riley, Sr. | ......... | A61B 5/18 |
| | | | | 340/576 |
| 2015/0335282 A1 | 11/2015 | Lee | | |
| 2016/0014129 A1 | 1/2016 | Park et al. | | |
| 2016/0034696 A1 | 2/2016 | Jooste et al. | | |
| 2016/0051191 A1 | 2/2016 | Miller et al. | | |
| 2016/0078739 A1 | 3/2016 | Burton et al. | | |
| 2016/0092659 A1 | 3/2016 | Wei | | |
| 2016/0094525 A1 | 3/2016 | Lin et al. | | |
| 2016/0128626 A1 | 5/2016 | Johnson et al. | | |
| 2016/0171591 A1 | 6/2016 | Williams et al. | | |
| 2016/0231812 A1 | 8/2016 | Hansen et al. | | |
| 2016/0242658 A1 | 8/2016 | Lisogurski | | |
| 2016/0246392 A1 | 8/2016 | Liu et al. | | |
| 2016/0261147 A1 | 9/2016 | Blum et al. | | |
| 2016/0270717 A1* | 9/2016 | Luna | ......... | A61B 5/743 |
| 2016/0327979 A1 | 11/2016 | Lettow | | |
| 2016/0364972 A1 | 12/2016 | Torti | | |
| 2016/0374124 A1 | 12/2016 | Gothe et al. | | |
| 2016/0379473 A1 | 12/2016 | Bharti et al. | | |
| 2017/0005504 A1 | 1/2017 | Rho et al. | | |
| 2017/0010664 A1 | 1/2017 | Tanaka et al. | | |
| 2017/0068533 A1 | 3/2017 | Kiaie et al. | | |
| 2017/0076522 A1 | 3/2017 | Ives-Halperin et al. | | |
| 2017/0083312 A1 | 3/2017 | Pindado et al. | | |
| 2017/0093582 A1 | 3/2017 | Keidar et al. | | |
| 2017/0132613 A1 | 5/2017 | Tunnell et al. | | |
| 2017/0198349 A1 | 7/2017 | Rice | | |
| 2017/0212989 A1 | 7/2017 | Laborde et al. | | |
| 2017/0263113 A1 | 9/2017 | Tiberi et al. | | |
| 2017/0308666 A1 | 10/2017 | Thomson et al. | | |
| 2019/0095119 A1 | 3/2019 | Vandewater | | |
| 2019/0107969 A1 | 4/2019 | Vandewater et al. | | |
| 2025/0388218 A1* | 12/2025 | Yong | ......... | B60W 40/11 |

FOREIGN PATENT DOCUMENTS

| | | |
|---|---|---|
| WO | 02058307 A2 | 7/2002 |
| WO | 2005079667 A1 | 9/2005 |
| WO | 2005101279 A2 | 10/2005 |
| WO | 2006006159 A1 | 1/2006 |
| WO | 2006060669 A2 | 6/2006 |

OTHER PUBLICATIONS

Jeroen Van Den Brand et al., "Flexible and Stretchable Electronics" 2015, pp. 116-120, in Solid-State Electronics 113.

Douglas Hackler et al., "Enabling Electronics With Physically Flexible I Cs and Hybrid Manufacturing" 2015, pp. 633-643, in Proceedings of the IEEE, vol. 103, No. 4.

Kuniharu Takei, "Toward Flexible and Wearable Human-Interactive Health-Monitoring Devices" 2014, Advanced Healthcare Mater, vol. 4, pp. 487-500.

Yang Gao, "Crack-Insensitice Wearable Electronics Enabled Through High-Strength Kevlar Fabrics" 2015, IEEE Transactions on Components, Packaging and Manufacturing Technology.

Michael P Gaj, "Organic light-emitting diodes on shape memory polymer substrates for wearable electronic" 2015, Organic Electronics, vol. 25, pp. 151-155.

Blount et al., "Remote health-care monitoring using Personal Care Connect", IBM Systems Journal, vol. 46, No. I, pp. 95-113, (2007).

Milenkovic et al., "Wireless sensor networks for personal health monitoring: Issues and an implementation", Computer Communications, 13 pages (2006).

Setton et al., "Bluetooth sensors for wireless home and hospital healthcare monitoring", Cyberfab, 6 pages, date unknown.

Korhonen et al., "Health Monitoring in the Home of the Future", IEEE Engineering in Medicine and Biology Magazine, pp. 66-73 (May/Jun. 2003).

"WHMS—Wearable Health Monitoring Systems", Electrical and Computer Engineering, The University of Alabama in Huntsville, http://www.ece.uah.edu/-jovanov/whrms/, 13 pages.

Hung et al., "Implementation of a W AP-Based Telemedicine System for Patient Monitoring" IEEE Transactions of Information Technology in Biomedicine, vol. 7, No. 2, pp. 101-107 (Jun. 2003).

Lee et al., "Design and Implementation of a Mobile-Care System over Wireless Sensor Network for Home Healthcare Applications", Proceedings of the 28th IEEE EMBS Annual International Conference, pp. 6004-6007 (Aug./Sep. 2006).

Chen et al., "An i-Mode Portable Healthcare Monitor", Proceedings of the Second Joint EMBS/BMES Conference, IEEE, pp. 1851-1852 (2002).

Kuo et al., "Design and Implementation of Internet-Based In-House Healthcare and Home Automation Systems", IEEE, pp. 2944-2949 (2003).

Jov Anov et al., "Stress Monitoring Using a Distributed Wireless Intelligent Sensor System", IEEE Engineering in Medicine and Biology Magazine, pp. 49-55 (May/Jun. 2003).

Lubrin et al., "Wireless Remote Healthcare Monitoring with Motes", Proceedings of the International Conference on mobile Business, IEEE Computer Society, 7 pages (2005).

Guo et al., "Implementing a wireless portable healthcare monitoring system for physiological signals", The Institute of Engineering and Technology, 1 page (2007).

Otto et al., "System Architecture of a Wireless Body Area Sensor Network for Ubiquitous Health Monitoring", Journal of Mobile Multimedia, vol. 1, No. 4., pp. 307-326 (2006).

Yu et al., "A Wireless Physiological Signal Monitoring System with Integrated Bluetooth and WiFi Technologies", Proceedings of the 2005 IEEE Engineering in Medicine and Biology 27th Annual Conference pp. 2203-2206 (2005).

"Body Area Networks—A "Healthy Aims" Projects", Zarlink Semiconductor Inc., 1 page (2007).

"Bionformatics" downloaded from webpage http://en.wikipedia.org/wiki/Bioinformatics on Aug. 2, 2007 (9 pages).

Mintz, "Microsoft Launches Health Records Site," downloaded from webpage http://bz.yahoo.com/ap/071004/microsoft_healthvault.html? . v= 1 on Dec. 18, 2007 (3 pages).

"Bluetooth Sig Aims To Improve Healthcare Experience Through Interoperability," downloaded from webpage http://www.bluetooth.com1Bluetooth/Press/SIG/BLUETOOTH SIG_ AIMS_TO_ IMPROVE_HEALTHCARE EXPERIENCE THROUGH INTEROP-ERABILITY.htm (2 nae:es).

How PGP Works, http://www.pgpi.org/doc/pgpintro/.

Princeton University Wordnet; http://wordnetweb.princeton.edu/perl/webwn?s=event; accessed Dec. 19, 2010.

Doc004(http://www.frascati.enea.it/documentation/tru6450/SUPPDOCS/OBJSPEC/DOCU 004 .H TM (Year: 2005).

Tool Interface Standard (TIS) Executable and Linking Format (ELF) Specification Version 1.2, TIS Committee, May 1995, pp. 1-106.

Honda et al., "Wearable, Human-Interactive, Health-Monitoring, Wireless Devices Fabricated by Macroscale Printing Techniques," Advanced Functional Materials, vol. 24, pp. 3299-3304, (2014).

Tajima et al., "Truly Wearable Display Comprised of a Flexible Battery, Flexible Display Panel, and Flexible Printed Circuit," Journal of the Society for Information Display, vol. 22( 5), pp. 237-244, (2015).

(56)     References Cited

OTHER PUBLICATIONS

United States Patent and Trademark Office; Office Action received in U.S. Appl. No. 18/584,330, mailed Oct. 1, 2025.
United States Patent and Trademark Office; Final Office Action received in U.S. Appl. No. 19/083,837, mailed Oct. 21, 2025.
United States Patent and Trademark Office, Office Action received in U.S. Appl. No. 19/075,505, mailed Jun. 3, 2025.
United States Patent and Trademark Office, Office Action received in U.S. Appl. No. 19/072,628, mailed May 8, 2025.
United States Patent and Trademark Office, Office Action received in U.S. Appl. No. 19/083,084, mailed Jun. 17, 2025.
United States Patent and Trademark Office; Office Action received in U.S. Appl. No. 19/083,837, mailed Jun. 26, 2025.

* cited by examiner

| ELF HEADER |
|---|
| *OTHER INFORMATION* |
| CODE SEGMENT |
| DATA SEGMENT |
| *OTHER INFORMATION* |
| RELOCATION SECTION 1 |
| RELOCATION SECTION 2 |
| *OTHER INFORMATION* |
| RELOCATION SECTION N |
| *OTHER INFORMATION* |

1200

| FLM HEADER |
|---|

| CODE SEGMENT HEADER |
|---|

| CODE BLOCK 1 | CODE RELOCATION |
|---|---|

| CODE BLOCK 2 | CODE RELOCATION |
|---|---|

| CODE BLOCK N | CODE RELOCATION |
|---|---|

| DATA SEGMENT HEADER |
|---|

| DATA BLOCK |
|---|

| DATA RELOCATION |
|---|

1300

| FLM HEADER |
| CODE SEGMENT HEADER |

| CODE BLOCK 1 | CODE RELOCATION |
| CODE BLOCK 2 | CODE RELOCATION |
| CODE BLOCK N | CODE RELOCATION |

| DATA SEGMENT HEADER |

| DATA BLOCK |

| DATA RELOCATION |

HEALTH MONITORING AND COMMUNICATIONS DEVICE

CROSS-REFERENCE TO RELATED APPLICATIONS

This application is a continuation of U.S. Ser. No. 17/897, 047 filed on Aug. 26, 2022, now U.S. Patent Application Publication No. 2022-0413728 entitled "COMPUTER SYSTEM FOR FACILITATING FINANCIAL TRANSACTIONS AND REDUCING FRAUD." U.S. Ser. No. 17/897, 047 is a continuation of U.S. Ser. No. 17/110,347 filed on Dec. 3, 2020 and entitled "PERSONAL DATA COMMUNICATIONS DEVICE." U.S. Ser. No. 17/110,347 is a continuation of U.S. Ser. No. 16/203,143 filed on Nov. 28, 2018, now U.S. Pat. No. 10,942,664 entitled "DEVICE CONFIGURED FOR DYNAMIC SOFTWARE CHANGE." U.S. Ser. No. 16/203,143 is a continuation of U.S. Ser. No. 15/256,137 filed on Sep. 2, 2016, now U.S. Pat. No. 10,185,513 entitled "DEVICE CONFIGURED FOR DYNAMIC SOFTWARE CHANGE."

U.S. Ser. No. 15/256,137 is a continuation-in part of U.S. Ser. No. 15/188,740 filed on Jun. 21, 2016 and entitled "SYSTEMS AND METHODS FOR PRODUCT ORDERING AND PAYMENT." U.S. Ser. No. 15/188,740 is a continuation of U.S. Ser. No. 15/174,632 filed on Jun. 6, 2016 and entitled "SYSTEMS AND METHODS FOR PRODUCT ORDERING AND PAYMENT." U.S. Ser. No. 15/174,632 claims the benefit of U.S. Provisional Application Ser. No. 62/171,944 filed on Jun. 5, 2015 and entitled "SYSTEM FOR PRODUCT ORDERING AND PAYMENT."

U.S. Ser. No. 15/256,137 also claims the benefit of: (i) U.S. Provisional Application Ser. No. 62/213,513 filed on Sep. 2, 2015 and entitled "SCHEDULING SECURITY AND MEDICAL DEVICES, SYSTEMS AND METHODS;" and (ii) U.S. Provisional Application Ser. No. 62/264,179 filed on Dec. 7, 2015 and entitled "SCHEDULING SECURITY AND MEDICAL DEVICES, SYSTEMS AND METHODS II."

The entire contents of all the foregoing applications are hereby incorporated herein by reference in their entirety (except for any subject matter disclaimers or disavowals, and except to the extent of any conflict with the disclosure of the present application, in which case the disclosure of the present application shall control).

TECHNICAL FIELD

The present disclosure generally relates to electronic devices. More particularly, exemplary embodiments of the disclosure relate to reconfigurable and/or reprogrammable electronic devices, including wearable devices.

BACKGROUND

Many consumers enjoy buying products and services from various merchants, such as restaurants, coffee shops, retailers, wholesalers, manufacturers and other vendors. As used herein, a "consumer" is any person or entity that purchases or otherwise acquires goods or services. A "merchant" or "establishment" is any entity that sells or otherwise provides goods and services. When ordering some items, consumers may arrive at the establishment, select their item or wait to place an order for the item, pay for the item, and then (sometimes) wait to receive the item(s)

ordered. Each step in this process is time-consuming and may diminish the experience associated with purchasing the item.

In some cases, consumers order items by telephone or on-line and pay for the item at the establishment or when the item is delivered. In an on-line purchase, a consumer typically goes to a merchant's website, reviews the items that can be purchased, and then places an order. For telephone purchases, the consumer calls and places an order. The consumer then pays for the item over the telephone via credit card or when the item is delivered. These steps can be undesirably time consuming. Additionally, the establishment may produce an order and never receive payment, or payment may be made and the order not received, or not received on time.

Additionally, payment over the internet, by telephone, or at a point of sale terminal at a merchant's location typically requires disclosing confidential information such as the payment card number, owner's name, CVV number, card expiration date, and often the card billing address. The information needed to authenticate a charge makes future fraudulent charges possible. As used herein, "payment card" or "card" means a credit card, debit card, or the like.

Devices for monitoring one or more of a user's (1) health, (2) vital signs such as heart rate, blood pressure, or blood oxygen level, (3) daily routine, (4) location, and (5) life activities, are limited in some respects. Especially for wearable devices, the device may be relatively large and bulky, unattractive, and have limited functionality.

SUMMARY

Various embodiments of the present disclosure relate to systems and methods for purchasing one or more items using a user device (also called a "device" herein), which can be a mobile cellular device, such as a cell phone, tablet, personal computer, or the like. A user software application (also called a "user application" or "application" herein) may be loaded on the device or accessible at a remote location by the device. The user application has, or has access to, a memory or database that stores two or more of the date an item(s) was purchased, item(s) purchased or ordered, merchant, merchant location, price paid, current price, other items offered by the merchant, delivery time for the item, time of day, month and/or year prior orders were placed, health information of the user, and information related to an item of food, such as calories, fat content, sugar content, carbohydrate content, whether or not gluten free, and/or other information.

When accessed by the user, the application can determine items previously purchased from one or more merchants, and display merchant(s) and most-frequently, or most recently purchased, items to a user, plus other items offered for sale by the merchant(s). The merchants can be selected as desired, for example from a group of previously-used merchants, from a group of nearby merchants—i.e., merchants that are within a determined distance from the user device, or a group of merchants that belong to a program. The device may display other items that the merchant may be attempting to sell, such as discounted items or holiday specialty items.

Exemplary systems and methods can also be used to easily and/or automatically purchase items. The purchase can be made without the need for a user to order and/or pay at the merchant location.

The user device enables a user to select one or more items to purchase and can facilitate payment to the merchant. The payment can be direct, such as by passing credit card or other payment information to the merchant through a computer or point of sale device. Or, the payment can be indirect through an intermediate system to avoid exposing the user's personal information to the merchant.

By way of example, an exemplary system includes the user device, a merchant payment device, and a payment issuer. As used herein, a payment issuer is a source of funds, such as a bank, associated with the user's card (e.g., a debit card, credit card, or the like) or bank account. The payment issuer can communicate with the user device and/or the user application. After an order has been placed by the user, the merchant payment device sends a request for payment to the user device or application, which forwards the request to the payment issuer including the card or bank account designated by the user. Systems at the payment issuer verify the transaction, for example by checking the user account number, expiration date, source of the payment request, and available funds, and sending a payment verification notification to the merchant system and to the user device. The monetary amount of the transaction is transferred into the merchant's account at the merchant's bank (which is defined as any account designated by the merchant for the receipt of funds). In this manner, the merchant system never has access to the user's confidential card or bank account information, but still receives payment, and the transaction for the sale of the item is consummated. The user and merchant can each verify the transaction was complete by using the verification notification, which may be a number or any other suitable indicia.

In accordance with yet further exemplary embodiments of the disclosure, the user device can be used to place an order ahead of time when a user is expected to arrive at a merchant location. The user device or application communicates directly with a merchant network or server. Payment can be made at the merchant location, or made indirectly as described above.

Exemplary systems and methods can additionally or alternatively perform other functions. For example, exemplary applications can calculate a time and/or distance between a user and a merchant. The system can know or calculate a time to fulfill an order based on historical data or based on a communication sent from merchant after the order is received.

Systems and methods according to the invention may also, once a merchant is selected, prompt the user to either order the same item as previously purchased, or as purchased most frequently, or both, and/or prompt the user to modify the order or select another item.

Additionally, any system or method according to aspects of the invention may include a database, or access one or more databases, for example associated with the user's health. Available information associated with the user's health may include weight, age, medical conditions (such as diabetes, high blood pressure, heart condition, and/or the like), and/or a diet program. The system may communicate with databases such as the individual's electronic health records, EMR (electronic medical record) and/or PHR (personal health record). The application can match this information with information related to food items, such as the sugar amount, salt amount, vitamin amount, contents, cholesterol amount, fat amount or starch amount available from a merchant and suggest items based on the user's medical condition and other factors, such as time of day.

Other aspects of the invention include a wearable electronic device (or "wearable device" or "embedded device") that can be worn by a user (which can be a patient), such as a band on the arm, leg, waist, head, or neck, or be part of an article of clothing, such as a belt or hat, or be attached to an article of clothing or a user.

A wearable device according to the invention can be configured to monitor one or more medical conditions of the user (such as heart rate, perspiration, blood pressure, blood oxygen level, signals sent by a monitor inside of the user's body, and others) either directly or through one or more sensors connected to the device. The device may be configured to communicate with a server, an intermediary device, or any other device (individually or collectively sometimes referred to as a "receiving device" when information is transmitted by the wearable device). In that case, information monitored by the wearable device may be transmitted to one or more receiving devices, and the receiving device may transmit information to the wearable device. The function of the wearable device may change based on many factors, including one or more of its location, the time of day, the day of the week, sensor(s) to which it is connected, a command from a user, and/or signals received from another device. The software on the wearable device may also be automatically changed or updated, or manually changed or updated by the user, and the changed or updated software may alter the function of the device. Changing the software to alter functionality may again be based on one or more factors such as location, sensors connected to the device, conditions detected by the device, a command from a user, the date, and the time of day.

A wearable device, or any device, may include software that is configured to permit dynamic changing or updating of software used with the device.

The system may update over time depending upon the new information it receives, for example based on system updates, new and/or additional data regarding a user or a merchant, and/or the like. The contents of this summary section are provided as a simplified introduction to the disclosure, and are not intended to be used to limit the scope of the appended claims.

BRIEF DESCRIPTION OF THE DRAWING FIGURES

DETAILED DESCRIPTION

The detailed description of exemplary embodiments herein makes reference to the accompanying drawing figures, which illustrate various embodiments by way of illustration. While various embodiments are described in sufficient detail to enable those skilled in the art to practice the disclosure, it should be understood that other embodiments may be realized and that logical and functional changes may be made without departing from the spirit and scope of the disclosure. Thus, the detailed description herein is presented for purposes of illustration only and not of limitation. For example, steps recited in a method or process may be executed in any order unless otherwise noted. Moreover, unless otherwise noted, functions or steps may be performed by one or more third parties.

Exemplary embodiments of the disclosure relate to electronic communication systems and methods to facilitate a transaction between a user and a merchant. As set forth in more detail below, various systems and methods employ a user device having an application thereon to perform various functions. For example, the application can retrieve information relating to a merchant, such as most-frequent purchases made by the user at that merchant. The merchant may be part of a franchise, in which case the information may include most-frequent purchase at the franchise, as opposed to at a single merchant of the franchise.

In accordance with some embodiments of the disclosure, a user and/or a merchant can participate in a program which confers certain privileges to its members. In these cases, various functions described below can be provided by a program manager—e.g., via cloud services described below. Such features can eliminate or reduce wait times for a consumer, reduce or eliminate incorrect orders, and eliminate a need to pay for items at a merchant location. Basic functions of the program can be offered to users for free, with additional functions added for a premium. Similarly, basic functions can be provided to merchants, with premium features provided to merchants for a fee. Or, merchants can be required to pay a fee (e.g., monthly or annually) to join the program.

Additionally or alternatively, exemplary systems and methods can provide a process for using a user device to place an order with a merchant and to pay for the order prior to arriving at a merchant location.

During a typical user/merchant transaction, such as a transaction at a restaurant, coffee shop, or similar merchant, a consumer (user) arrives at a merchant location, orders an item, pays for the item, and then waits to receive the item.

Figure 1:
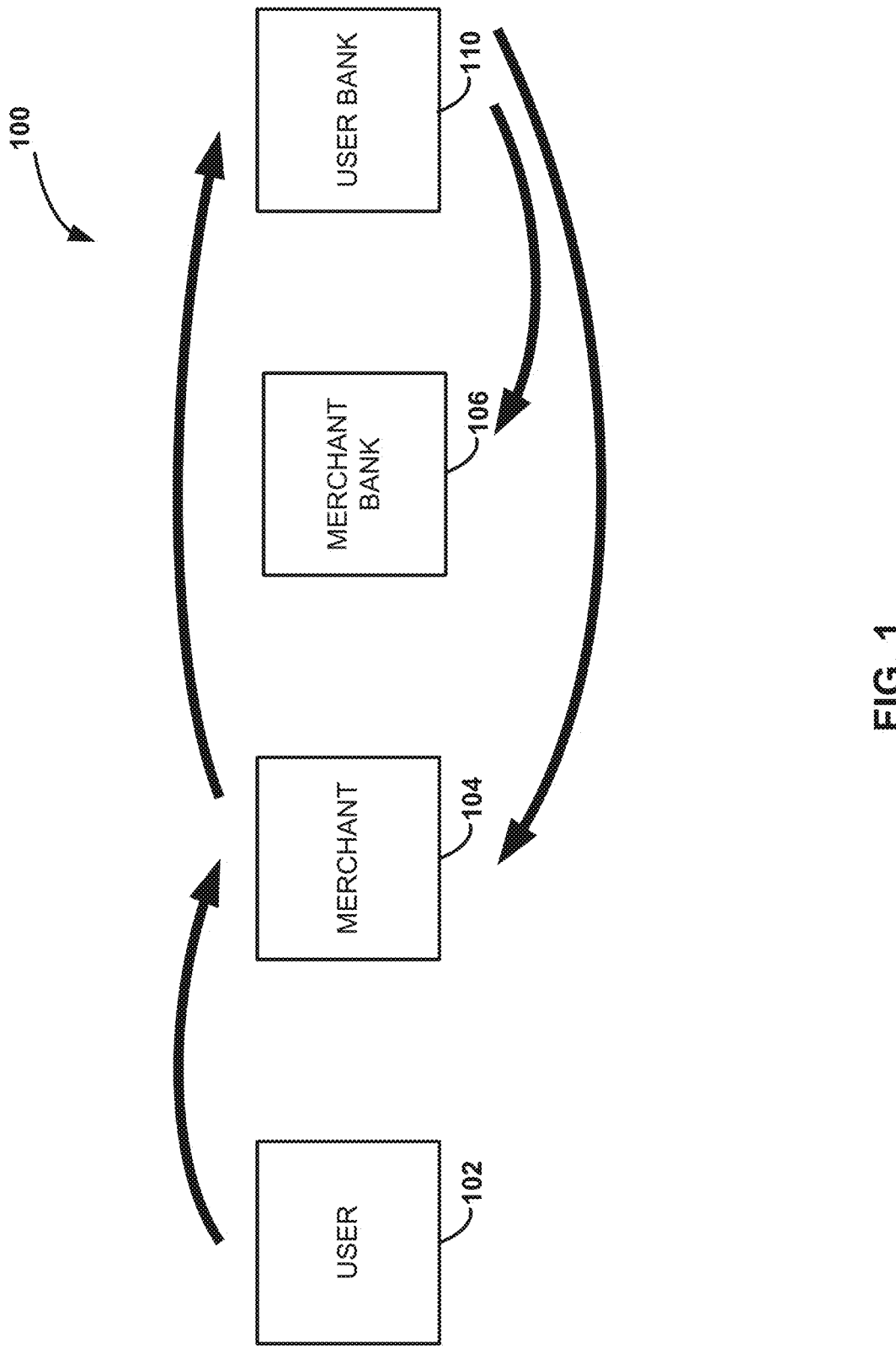
FIG. 1 illustrates a financial transaction system as known in the art.

FIG. 1 illustrates the typical process. In this case, a user 102 presents payment information (e.g., a credit card or debit card) to a merchant. A merchant device 104 then transmits a request for payment to an acquiring bank 106 (e.g. the merchant's bank). Then, e.g., using a financial network 108, acquiring bank 106 requests payment on behalf of the merchant from an issuing financial institution (e.g., the user's bank). While such systems work relatively well, they require the presence of the user at the merchant site prior to or when paying for the item. Such systems also require the user to spend additional time at the merchant site. In addition, user financial information is generally provided by a user directly to merchant device 104. Providing such financial information may be undesirable, because such information can be misused by a third party. In addition, if the user is paying with a credit or debit card, the user and/or merchant may be susceptible to fraud.

Figure 2:
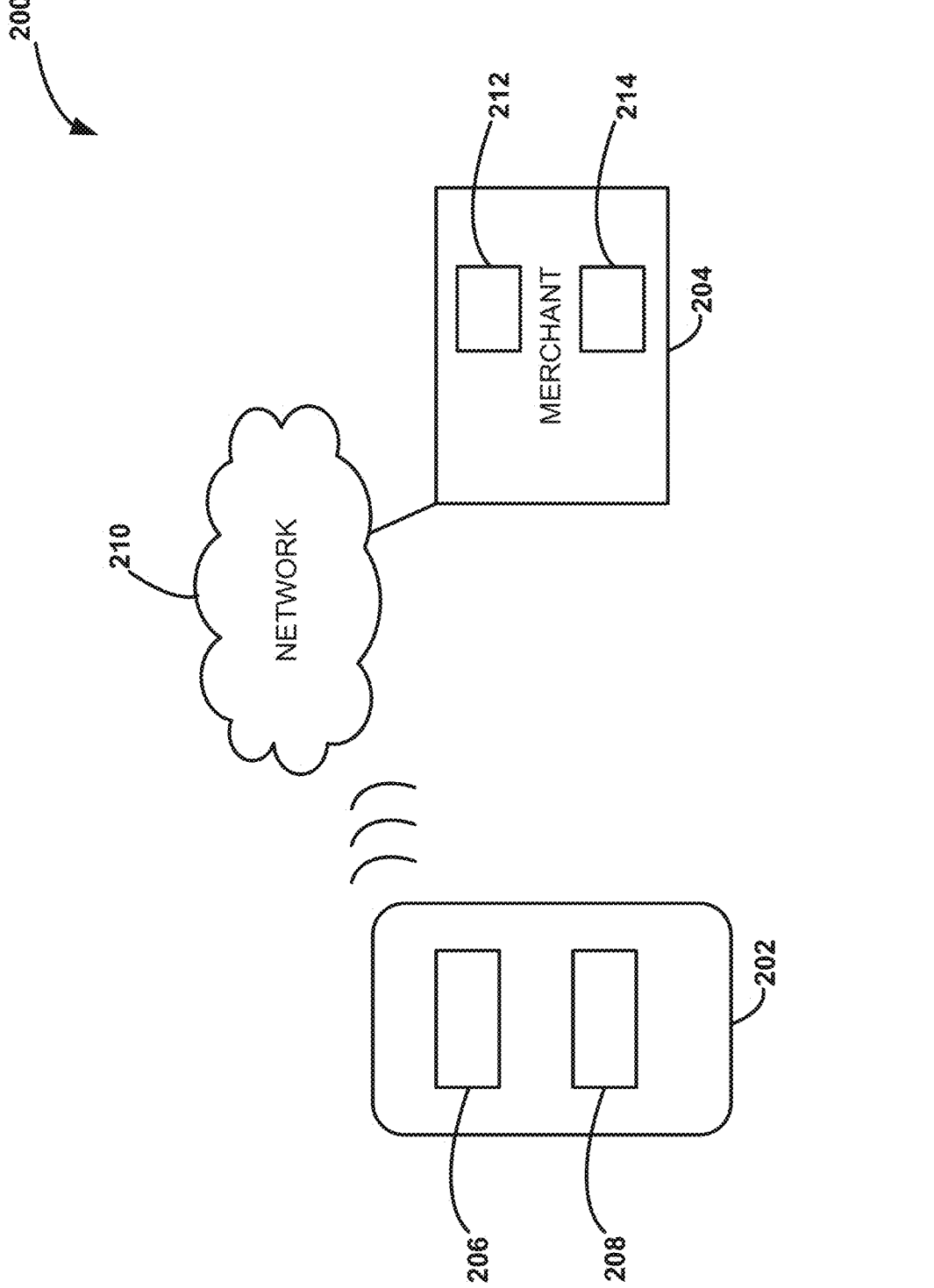
FIG. 2 illustrates an electronic communication and payment system in accordance with exemplary embodiments of the disclosure.

In contrast to these prior approaches, exemplary systems and methods allow for more convenient and/or automated ordering, reduce wait times, provide suggestions for orders, and/or the like. FIG. 2 illustrates an electronic communication and payment system 200 in accordance with various exemplary embodiments of the disclosure. Electronic communication and payment system includes a user device 202 and a merchant device 204. As set forth in more detail below, in accordance with exemplary embodiments of the disclosure, user device 202 can be used to place an order for one or more items—e.g., for later pickup by a user/consumer and can transmit payment (e.g., by way of a credit card payment, debit card payment, token, credit, or the like) to merchant device 204. Communication between user device and merchant device can be direct or be transmitted through a network 210. Additionally or alternatively, the payment can proceed without involvement of other financial institutions, as illustrated in FIG. 2, or may go through one or more intermediary financial institutions, as discussed in more detail below in connection with other figures.

User device 202 can comprise any suitable device with wireless communication features or that can communicate over a network. In the illustrated examples, user device 202 is illustrated using mobile, cellular, satellite, and/or wireless communication. However, the disclosure is not so limited. By way of examples, user device 202 can include a computing unit or system. The computing units or systems may take the form of a computer, a set of computers, a smartphone, a laptop (for example, a MacBook), a notebook, a tablet (for example, an iPad), a hand-held computer, a personal digital assistant, a set-top box, a workstation, a computer-server, a main frame computer, a mini-computer, a PC server, a pervasive computer, a network set of computers, a personal computer, a kiosk, a point of sale (POS) device and/or a terminal, a television, or any other device capable of receiving and/or sending data over a network. User device 202 may run Microsoft Internet Explorer®, Mozilla Firefox®, Google® Chrome, Apple® Safari, Apple® IOS, Android, or any other suitable software package(s). In accordance with various embodiments of the disclosure, user device 202 is global positioning system (GPS) enabled in order to provide and/or utilize location information associated with device 202. For example, device 202 may be configured to support geo-location and/or location-based services.

In accordance with various embodiments of the disclosure, user device 202 includes an application 206 to perform one or more functions as described herein. In accordance with various aspects of these embodiments, application 206 uses GPS-enabled features of user device 202 to allow user device 202 to perform certain functions based on, for example, a distance between a user (with user device 202) and a merchant (with merchant device 204), an expected amount of time it will take a user to reach the merchant (which can depend on one or more modes of transportation, such as walking, driving, public transportation, or combinations thereof). For example, as discussed in more detail below, a user can use user device 202 and application 206 to place an order, wherein the order will be transmitted to a merchant (either directly or through various networks) based on a user proximity to the merchant, an expected time for a user to reach a merchant, or the like.

A consumer can use user device 202 and application 206 to cause various functions to be performed. As used herein, the terms "consumer," "user," "end user," and "customer" may be used interchangeably with each other, and each may include any person, entity, government organization, business, machine, hardware, and/or software. Application 206 can be a stand-alone application, part of an operating system, or a web plug-in. In any of these cases, user device 202 can act as a web client that communicates via a network (e.g., network 210). Web clients may include a browser application which interfaces with a network. Such browser applications typically include internet browsing software installed within a computing unit or a system to conduct online transactions and/or communications.

During a transaction, a user can use user device 202 to review nearby merchants (e.g., based on GPS coordinates) and review recent orders placed with such nearby merchants. The recent order(s) can be displayed as a default (or only) order option. A default option can be, for example, the most recent order, a most-frequent order (e.g., the most frequent from the last 2 or more orders), a most popular order based on transaction data for a merchant, and/or the like. A price can be displayed proximate the item, and an option to buy one or more items can be displayed to the user.

In accordance with some exemplary embodiments of the disclosure, application 206 can be enabled to be continuously running in the background, so that when a user is within a predetermined distance (e.g., 5 miles, 2 miles, 1 mile, 0.5 mile, or the like) from a predefined merchant (e.g., a merchant participating in a program), application 206 automatically displays a user interface, such as one or more user interfaces discussed in more detail below in connections with FIGS. 7-9. The amount of distance or time can be user selected or merchant selected and can be based on, for example, a mode of transportation used by the user and/or an average speed that the user is traveling.

By way of one example, application 206 can be used to calculate where the customer is located relative to a drive-through restaurant or facilities thereof, so as to engage the user at the appropriate time. At the start of the drive-through (i.e., as the user approaches and/or enters the drive-through area of a restaurant) the user is prompted by application 206 as to whether the user wants the same order as a previous order, a most-frequent order item, or the like. At the speaker the user is asked to pull forward, because the order is already in the system. Prior to or at a payment window, the application 206 provides a display requesting payment prior to or after receiving the user's order.

Another example is just-in-time ordering as noted above. In this case, device 202 or 204 or another device, such as a device provided by a cloud service, discussed in more detail below, calculates how far (or how much time) a customer is away from a given location after ordering, and places the order with merchant device 204 after calculating the preparation and any additional time, before the customer arrives at the merchant site. In accordance with some embodiments, a customer can have an option presented on user device 202 to "prepare now," in which case the order is placed in the merchant queue and is processed in order (or with preference to those in the program).

Application 206 can optionally include an option to "pay it forward" and/or "pay it backward." Something trending in coffee lines is the concept of paying for the car ahead of you (e.g., when you are at the speaker) or the car behind you when you are at the pickup window. A user can push a button using application 206 on user device 202 to do either and this can be based on, for example, user device's communications to merchant device 204—either directly or via a cloud service. For privacy reasons, the order of the other person may not be shown to the user paying for such items.

In accordance with additional exemplary embodiments of the disclosure, application 206 can be used to review (e.g., real-time) wait times associated with particular merchants. For example, in the case of restaurants, application 206 can be used to look at restaurants (e.g., restaurants enlisted in a program) in the area to see how long their wait list is. The restaurants can be displayed to a user in certain areas by, for example, choice of food, location, and/or wait times. After receiving such information, users can use the ability to push up on the line with the "put me in line" feature, for example, as discussed below.

In accordance with yet further additional or alternative embodiments, application 206 and user device 202 can be used in connection with pull-up services. In these cases, a merchant can dedicate an area and/or parking spots to users participating in a program. In these cases, a user does not need to go through a drive through or wait in line. Rather, application 206 and/or a cloud service can send an alert to the merchant (e.g., merchant device 204) when a user is near or at the merchant location. A user may come in to get the order or to have it brought to their car. The establishment setup may record the location of the reserved parking spots.

User device 202 can also include a database 208. Database 208 can store information relating to various merchants and can store user order information associated with the merchants. Although illustrated as part of user device 202, database 208 or portions thereof can suitably form part of (and/or be accessed or accessible via) network 210 or another network. Database 208, in accordance with exemplary embodiments of the present disclosure can be implemented as a database management system (DBMS), a relational database management system (e.g., DB2, Oracle, SQL Server, My SQL, ACCESS, etc.), an object-oriented database management system (ODBMS), a file system, or in any another suitable manner. Database 208 can be accessed by a server via a Structure Query Language (SQL) or in any other desired manner. Database 208 may be organized in any suitable manner, including as data tables or lookup tables. Association of certain data may be accomplished through any desired data association technique and data association may be accomplished manually and/or automatically. In one embodiment, database 208 is configured to store information related to a service performed for a customer. Information from database 208 can be used by application 206 to, for example, facilitate performance of various functions described herein.

Database 208 can also store user account information. Phrases and terms similar to "account," "account number," "account code" or "consumer account" as used herein, can include any device, code (e.g., one or more of an authorization/access code, personal identification number ("PIN"), internet code, other identification code, and/or the like), number, letter, symbol, digital certificate, smart chip, digital signal, analog signal, biometric or other identifier/indicia suitably configured to allow the consumer to access, interact with or communicate with the system. In various embodiments, an account number can refer to a fifteen or sixteen digit number on a transaction instrument and a card security code on the transaction instrument. The account number may optionally be located on or associated with a rewards account, charge account, credit account, debit account, pre-paid account, telephone card, embossed card, smart card, magnetic stripe card, bar code card, transponder, radio frequency card or an associated account.

Merchant device 204 can include any suitable system, software, and/or hardware, such as devices noted above in connection with user device 202. A merchant can be a provider, broker and/or any other entity in the distribution chain of items. A merchant can be, for example, a coffee shop, a restaurant, a bookstore, a grocery store, a retail store, a travel agency, a service provider, a social media operator, an on-line merchant, a digital wallet provider, or the like. Phrases and terms similar to "business" or "merchant" may be used herein interchangeably with each other.

Merchant device 204 can include a merchant application 212. Merchant application 212 can facilitate communication between merchant device 204 and user device 202 and/or can facilitate setup of merchant device 204 to be used in accordance with exemplary embodiments of the disclosure. For example, merchant application can be used to receive an order and/or indication of a payment from a customer and, in some cases, can transmit a verification of receipt of payment to user device 202 or to another entity. Merchant application 212 can also allow a merchant to input information regarding the merchant, such as merchant account information, location of merchant, and/or GPS coordinates for locations associated with the merchant (e.g., GPS coordinates of a drive-up window, a pickup window, a payment window, a pickup location, and the like). Additionally or alternatively, merchant application 212 can allow a merchant to enter expected wait times associated with various items. The expected wait times can include preparation time and additional time, which can be entered or calculated using, e.g., one or more of the devices described herein. The additional time can include, for example, additional time associated with a user traveling to the merchant site, additional time associated with additional customers at a merchant site, a time of day, a time of year, and the like.

By way of example, merchant application 212 can prompt a merchant to mark a start of their drive-through where the GPS location will be recorded, stepping at a suitable interval (for example, approximately every 10 feet), then marking the GPS location for a speaker, and then marking a GPS location for a serving window. This allows quick setup of merchant application 212 to get a merchant online quickly. Such information can be used to calculate where in line the user is at in order to pop up the appropriate user interface when the user is close to the merchant. Such information can be stored on merchant device 204 and/or on part of a network or cloud service discussed below.

Merchant device 204 can also include a database 214. Database 214 can be used to store payment information, such as customer name, order, and indication of payment received. Database 214 can include the same system and/or software described above in connection with database 208, or may differ from database 208, as desired.

Network 210 can include a local area network (LAN), a wide area network, a personal area network, a campus area network, a metropolitan area network, a global area network, a financial network, the internet, or the like. Network 210 can be coupled to one or more user devices 202, merchant devices 204, and/or other devices using an Ethernet connection, other wired connections, wireless interfaces, such as Bluetooth, W-Fi, or mobile communication protocols, such as wireless application protocol (WAP), or the like. Network 210 can be coupled to other networks and/or to other devices.

Network 210 may comprise any suitable electronic communications systems or methods which incorporate software and/or hardware components. Communication may be accomplished through any suitable communication channels, such as, for example, a telephone network, an extranet, an intranet, the internet, point of interaction device (point of sale device, personal digital assistant, smart phone, cellular phone (e.g., iPhone®, Windows Phone®, Android, or Blackberry®), kiosk, etc.), online communications, satellite communications, off-line communications, wireless communications, transponder communications, local area network (LAN), wide area network (WAN), virtual private network (VPN), networked or linked devices, keyboard, mouse and/or any suitable communication, data input modality, and any combinations thereof. Network 210 may be implemented with TCP/IP communications protocols and/or using IPX, Appletalk, IP-6, NetBIOS, OSI, any tunneling protocol (e.g., IPsec, SSH), or any number of suitable existing or future protocols. If network 210 is in the nature of a public network, such as the internet, it may be advantageous to presume the network 210 to be insecure and open to eaves-droppers. Specific information related to the protocols, standards, and application software utilized in connection with the internet is generally known and, as such, need not be detailed herein.

The various system components described herein can be independently, separately or collectively coupled to network 210 via one or more data links including, for example, a connection to an Internet Service Provider (ISP) over a local loop as is typically used in connection with standard modem communication, cable modem, Dish networks, ISDN, Digital Subscriber Line (DSL), or various wireless communication methods. The systems and methods disclosed herein contemplate the use, sale and/or distribution of any goods, services or information over any network having functionality similar to that described above with reference to network 210.

Figure 3:
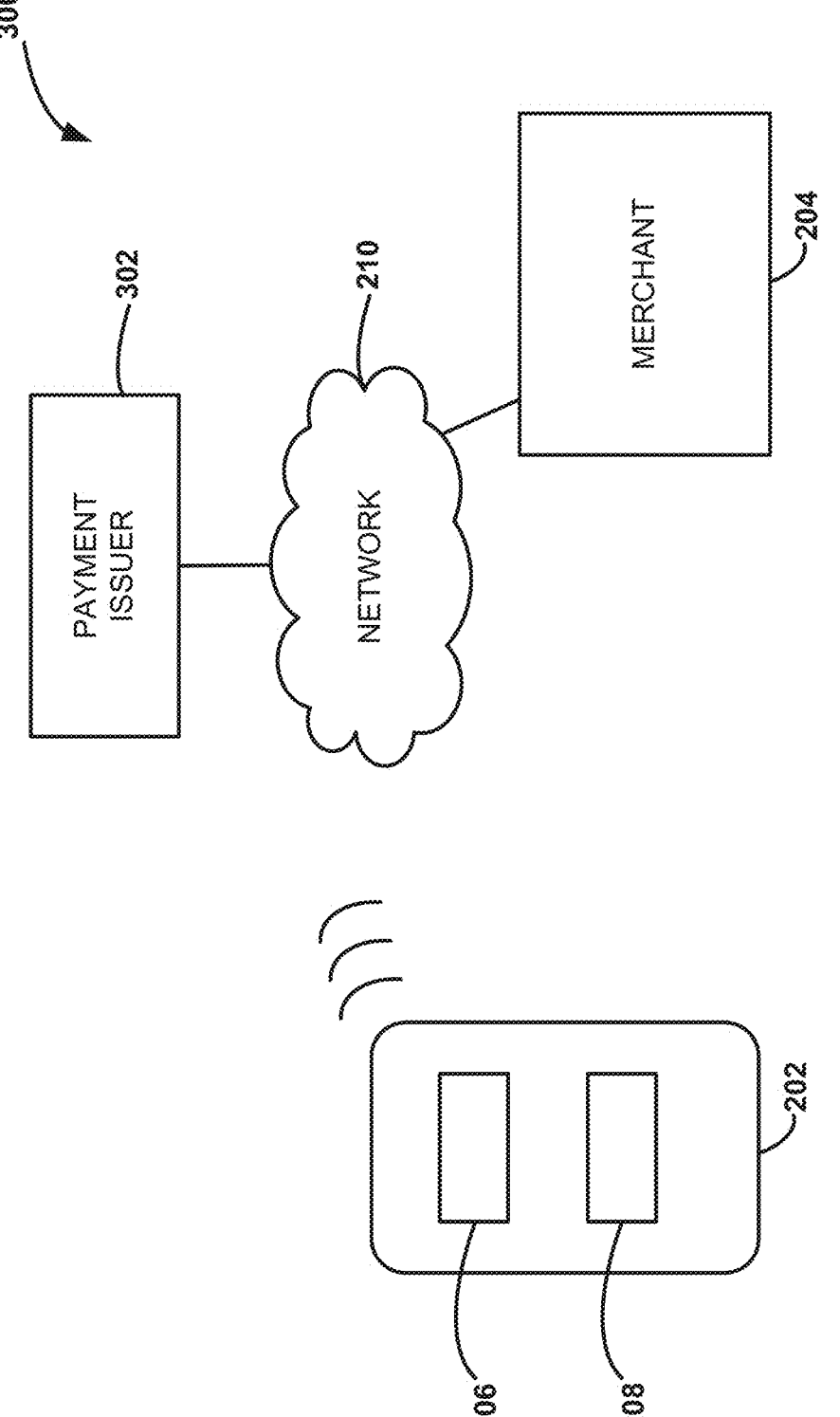
FIG. 3 illustrates another exemplary electronic communication and payment system in accordance with embodiments of the disclosure.

FIG. 3 illustrates another exemplary electronic communication and payment system in accordance with additional exemplary embodiments of the disclosure. System 300 is similar to system 200, except system 300 includes a payment issuer 302.

Payment issuer 302 can be any entity that offers transaction account services, such as a financial institution. The financial institution can represent any type of bank, lender or other type of account-issuing institution, such as credit card companies, card-sponsoring companies, or third-party issuers under contract with financial institutions. It is further noted that other participants may be involved in some phases of the transaction, such as an intermediary settlement institution.

Payment issuer 302 can include a company (e.g., a third party) appointed (e.g., by a merchant) to handle transactions for merchant banks. In accordance with some exemplary embodiments of the disclosure, payment issuer 302 can be broken down into two types: front-end and back-end. A front-end payment issuer 302 can have connections to various transaction accounts and supply authorization and settlement services to the merchant banks' merchants. A back-end payment issuer 302 accepts settlements from front-end processors and, via the Federal Reserve bank, move money from an issuing bank to the merchant bank. In an operation that will usually take a few seconds, the payment issuer can both check the details received by forwarding the details to the respective account's issuing bank or card association for verification, and may carry out a series of anti-fraud measures against the transaction. Additional parameters, including the account's country of issue and its previous payment history, may be used to gauge the probability of the transaction being approved. In response to the payment issuer receiving confirmation that the transaction account details have been verified, the information may be relayed back to the merchant and/or the user. In response to the verification being denied, the payment issuer can relay corresponding information to the merchant and/or the user.

As used herein, "transmit" may include sending electronic data from one system component to another over a network connection. Additionally, as used herein, "data" may include encompassing information such as commands, queries, files, data for storage, and the like in digital or any other form.

To conduct a transaction using electronic communication and payment system 300, a user can select a merchant and item(s) using application 206 and database 208. A user can then select to pay for the items using application 206. The payment information for the transaction can be stored in database 208 and can include one or more payment options. Once the user selects payment, the payment request is transmitted to payment issuer 302—e.g., using network 210. Once payment issuer 302 receives the payment request, payment issuer 302 can send indication of payment, payment, or a token to merchant device 204. Payment issuer 302 and/or merchant device 204 can send user device 202 verification of payment, which a user can present to a merchant upon pickup of the ordered item(s).

Figure 4:
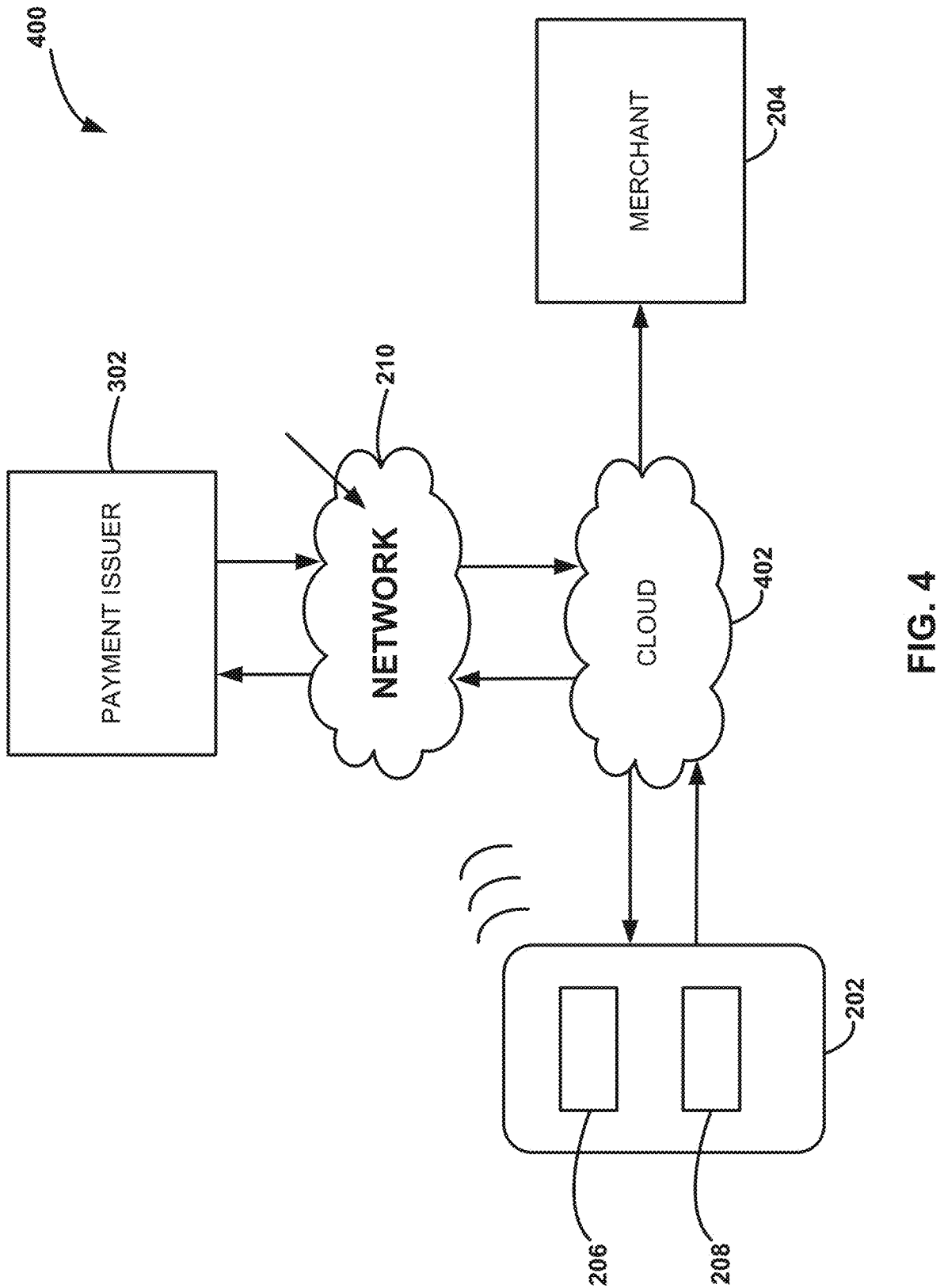
FIG. 4 illustrates another exemplary electronic communication and payment system in accordance with various embodiments of the disclosure.

FIG. 4 illustrates another electronic communication and payment system 400 in accordance with further exemplary embodiments of the disclosure. Electronic communication and payment system 400 is similar to electronic communication and payment system 300, except electronic communication and payment system 400 includes a cloud service 402.

Cloud service 402 can include one or more servers or other device capable of performing exemplary cloud service functions. In various exemplary embodiments, cloud service 402 can include any of the network components described above in connection with network 210. Further, although illustrated separately, cloud service 402 may form part of network 210.

In accordance with exemplary embodiments of the disclosure, cloud service 402 can facilitate user and merchant account setup and/or can store information, such as account information, associated with merchants and/or users. In accordance with further examples, cloud service 402 can additionally or alternatively act as a payment intermediary, such that user account information is not passed to merchant device 204.

For example, cloud service 402 can receive and store merchant information received from merchant device 204. A merchant can enter merchant information, such as location (e.g., address and/or GPS location), menu items, specials, and prices. The merchant information can include specific information, such as GPS locations of drive-up windows, payment windows, and the like.

Similarly, cloud service 402 can receive and store user information, such as one or more of: a user device identifier, merchants, related items (e.g., for each of one or more merchants), payment information (e.g., credit card, debit card, third-party service such as PayPal, or the like). Alternatively, some, including any combination, of such information can be stored on user device 202—e.g., in database 208.

In the illustrated example, when a user places an order using user device 202, cloud service 402 receives the order, and passes a payment request to payment issuer 302—e.g., through network 210. Payment issuer 302 then issues a payment to cloud service 402. The payment can reside with cloud service 402 for a prescribed period of time or until a merchant requests such information. Alternatively, the payment or a corresponding credit can be pushed to merchant device 204. In accordance with some embodiments of the disclosure, the payment information provided by cloud service 402 to merchant device 204 can be in the form of a token or credit, such that user account information and/or payment issuer account information is never passed to merchant device 204. Once merchant device 204 or cloud service 402 receives payment, verification of the payment to user device 202 can be transmitted—either directly from merchant device 204, via cloud service 402 (which can then store such verification), or via another network.

Figure 5:
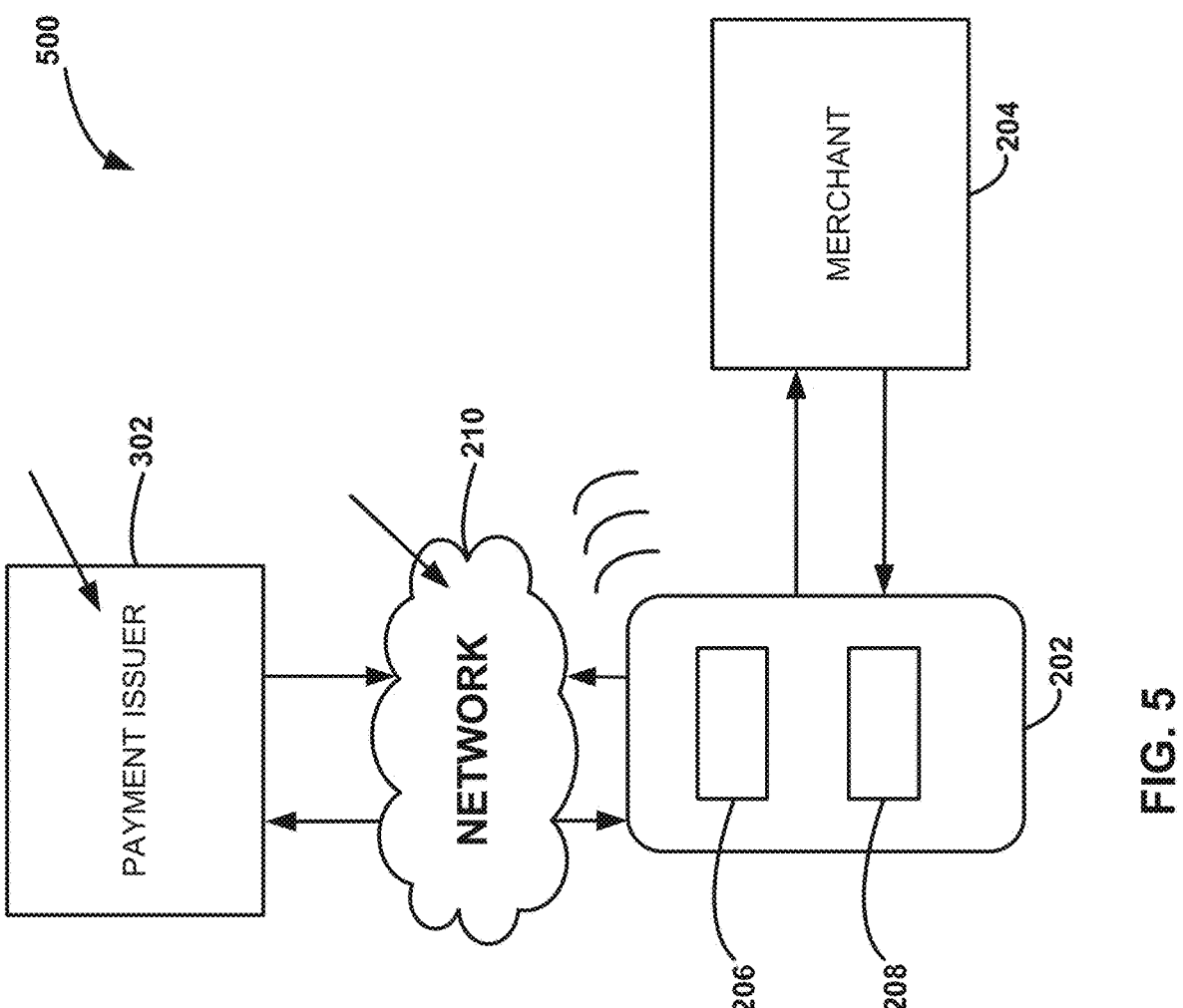
FIG. 5 illustrates another exemplary electronic communication and payment system in accordance with various embodiments of the disclosure.

FIG. 5 illustrates another electronic communication and payment system 500 in accordance with yet further exemplary embodiments of the disclosure. Electronic communication and payment system 500 is similar to electronic communication and payment system 400, except in the illustrated example of electronic communication and payment system 500, payment information from payment issuer 302 is passed through one or more networks 210 (which may include a cloud service 402 as described above) to user device 202. In this case, merchant information and/or user information can be stored in a cloud service, such as cloud service 402. When an order is placed using user device 202, a payment request is transmitted using network 210 to payment issuer 302. Payment issuer 302 then transmits a form of payment to user device 202 via network 210. User device 202 then transmits a payment (e.g., token, or credit) to merchant device 204. Although illustrated as a direct payment, the payment from user device 202 to merchant 204 can go through a suitable network. In accordance with some examples, merchant device 204 can send to user device 202 a verification of payment, which a user can then present to a merchant when picking up the ordered items.

Figure 6:
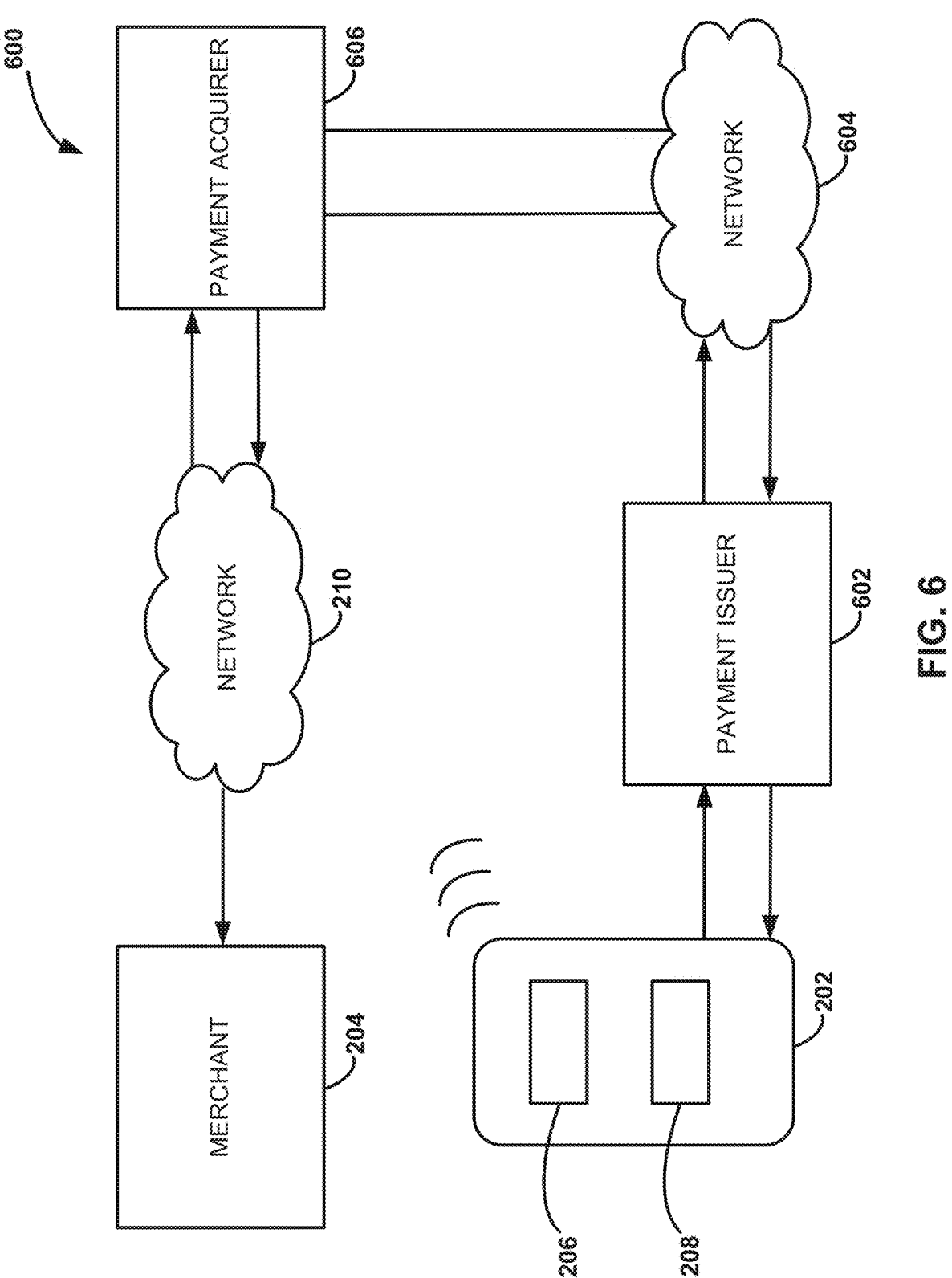
FIG. 6 illustrates a further exemplary electronic communication and payment system in accordance with various embodiments of the disclosure.

Turning now to FIG. 6, another electronic communication and payment system 600, in accordance with additional exemplary embodiments of the disclosure, is illustrated. Electronic communication and payment system 600 is similar to electronic communication and payment system 400, except electronic communication and payment system 600 utilizes a payment issuer 602, a network 604, and a payment acquirer 606.

Payment issuer 602 can be the same as or similar to payment issuer 302. Network 604 can include any of the network components described above in connection with network 210. By way of example, network 604 can include a bank or financial network.

Payment acquirer 606 can include any suitable financial institution, such as those described herein. In the illustrated example, a merchant using merchant device 204 can have a merchant account with payment acquirer 606.

In an illustrated example, when a user places an order to a merchant using user device 202, the order can be received via network 210 (which can be or include cloud service 402, as described above). Information regarding the order, such as a payment request, can then be transmitted to payment acquirer 606 and to payment issuer 602—e.g., via network 604. Order information can then be transmitted to merchant device 204 using network 210. Payment issuer 602 then transmits payment to payment acquirer 606 via network 604. Once payment is received by payment acquirer 606, a notification of receipt of payment can be sent to merchant device 204, so that the merchant receives an indication of the payment. Similar to other embodiments described above, in accordance with some examples of the disclosure, the indication of payment from payment acquirer 606 and/or network 210 to merchant device 204 does not include user account information, so that the merchant does not receive such information. Thus, any fraud on the user that originates at a merchant site or with merchant device 204 can be mitigated or eliminated.

In accordance with some exemplary embodiments of the disclosure, network 210 (e.g., a cloud service) can send verification of payment to user device 202. Additionally or alternatively, merchant device 204 can transmit a verification of payment to user device 202. Such verification can be displayed on user device 202 (e.g., using application 206) when picking up the ordered item(s) from the merchant.

Figure 7:
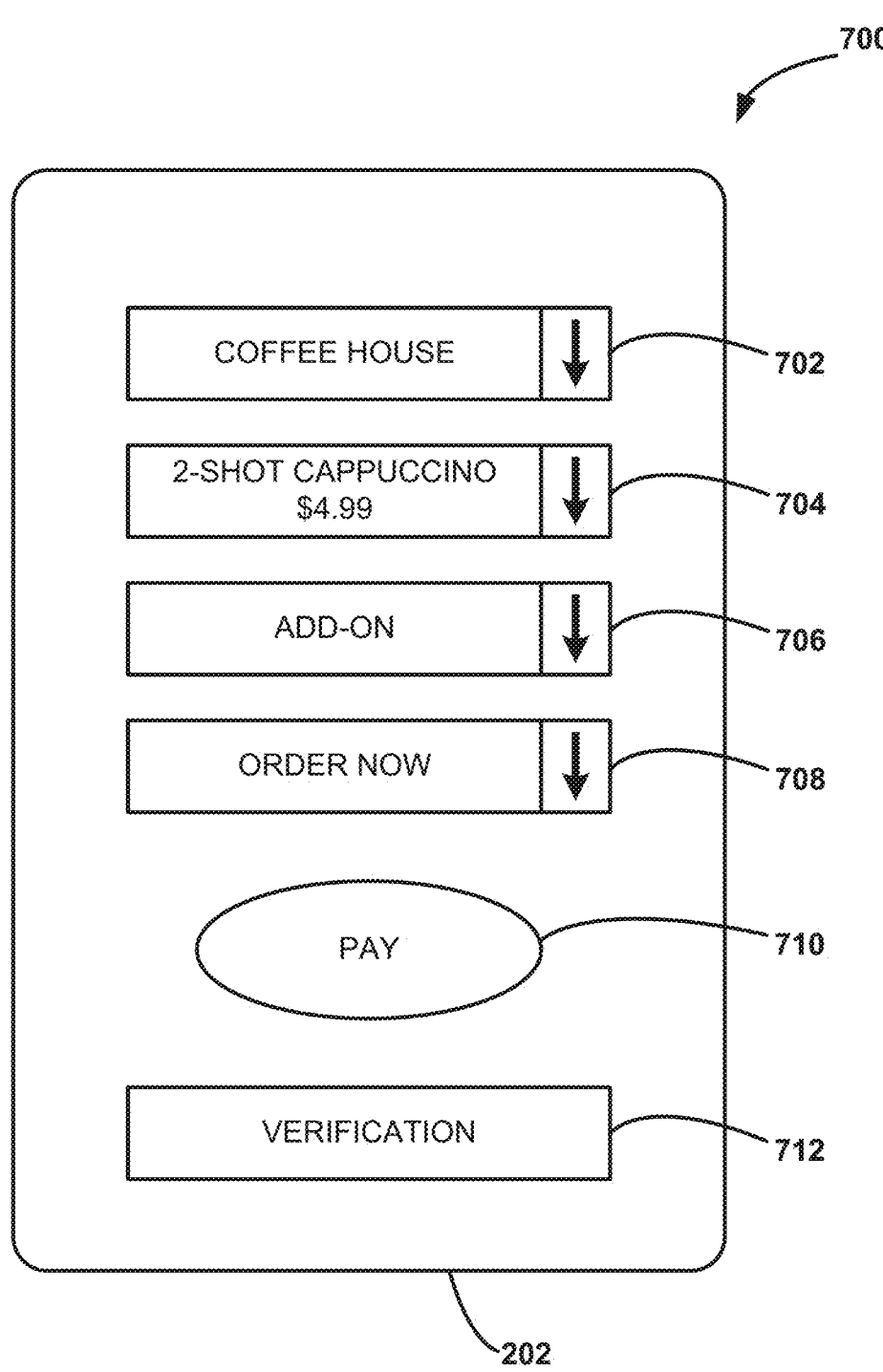
FIG. 7 illustrates an exemplary user interface on a user device in accordance with exemplary embodiments of the disclosure.
Figure 8:
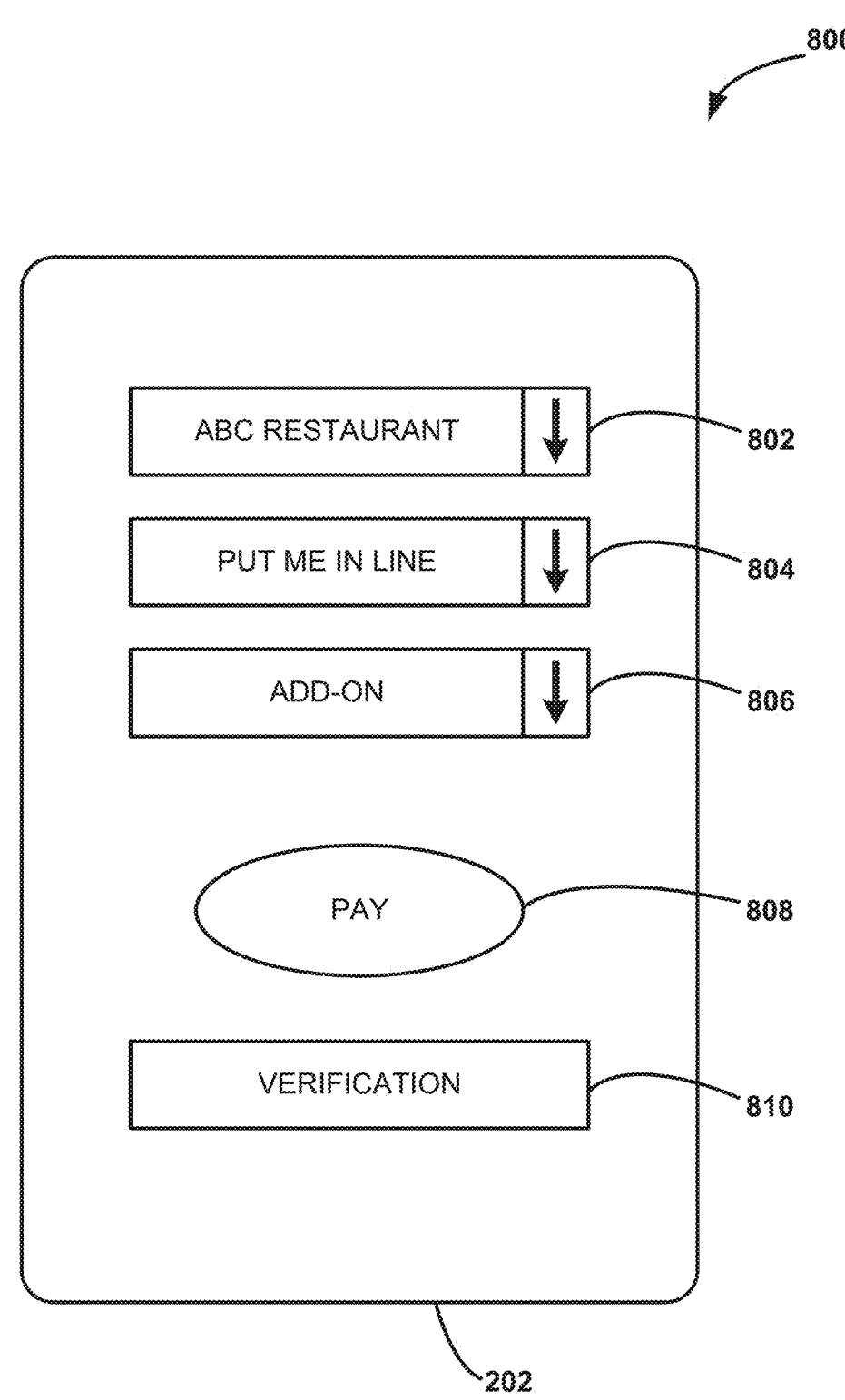
FIG. 8 illustrates another exemplary user interface on a user device in accordance with exemplary embodiments of the disclosure.
Figure 9:
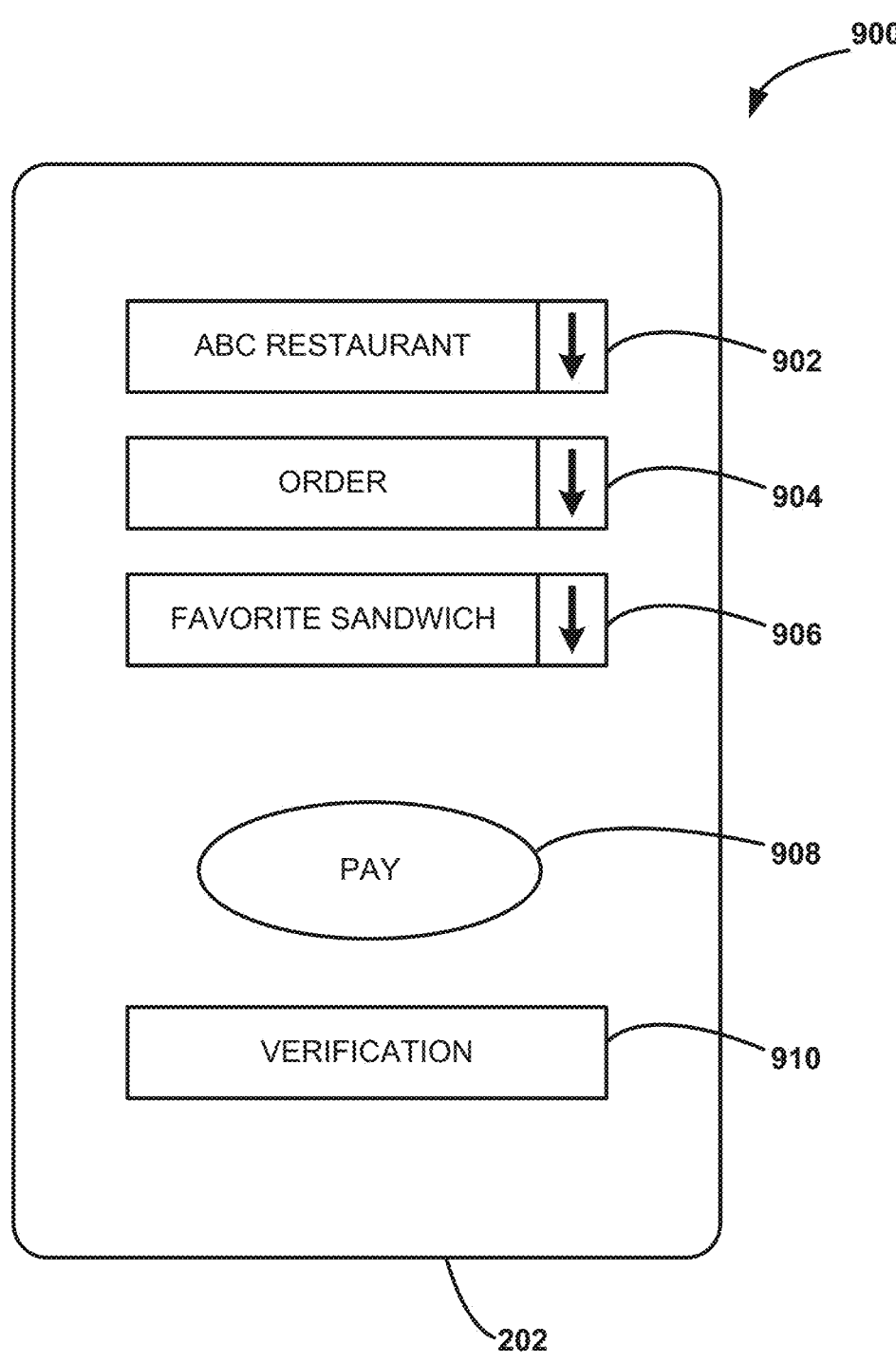
FIG. 9 illustrates another exemplary user interface on a user device in accordance with exemplary embodiments of the disclosure.
Figure 10:
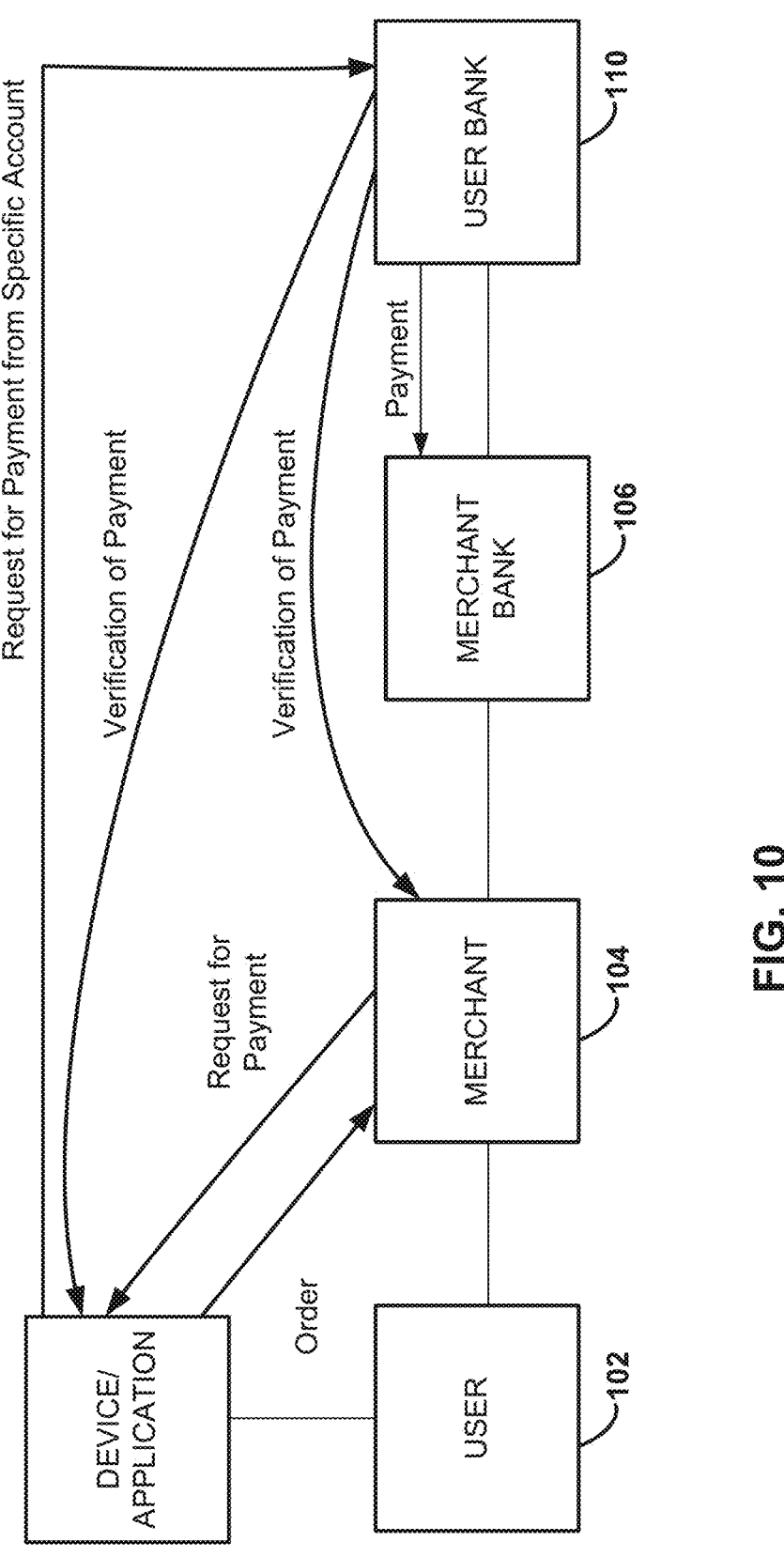
FIG. 10 illustrates a device and method for indirect payment to a merchant.

Turning now to FIGS. 7-9, various functions of user device 202 and user application 206 are described in connection with exemplary user interfaces. The illustrated user interfaces can be used in accordance with any of the exemplary electronic communication and payment systems described above.

FIG. 7 illustrates a user interface 700 in accordance with various examples of the disclosure. In the illustrated example, user interface 700 includes a display 702 to display information associated with a merchant. Display 702 can be configured to display information associated with only a particular merchant, to display a default merchant and have a drop-down or other selection box (as illustrated), or display information associated with multiple merchants. In accordance with various aspects of these embodiments, display 702 and/or user application 206 allows a user to enter or select a merchant.

Display 704 allows a user to select one or more items associated with a selected (or default or only) merchant. As noted above, to provide an improved user experience, application 206 can be configured to automatically display a most-frequently purchased item by a user on display 704. If a user desires to order another item, a user can use selection box 704 to order an alternative item from the merchant.

Display 706 allows a user to select one or more additional items to add to an order. Application 206 can cause to be displayed additional displays 706 if a user selects one or more add-on items.

Application 206 can allow a user to select from various ordering options, such as ordering now, ordering when within a distance or time from a merchant, ordering when within a distance or time of the merchant that is about the same as an estimated time to prepare the item(s) for pickup, or the like. For example, a predetermined amount of time to prepare an item, which can be based on, for example, an average amount of time to prepare the item, can be used to estimate an amount of time to prepare an ordered/selected item. In addition to a preparation time, an estimated time can be based on, for example, a time of day, a number of people in line, an additional amount of time supplied by a merchant, a time of year, an additional amount of time based on, for example, a special event, or the like. Application 206 can be configured to place the order (e.g., as a selected option) when a time for user device 202 to arrive at the merchant is about the same as an estimated time to prepare the item.

A user can select pay option 710 to pay for the ordered item(s). When payment option 710 is selected, payment information previously stored in database 208 can be used to pay for the selected items. If no prior payment information is stored in database 208, then a user can be prompted to enter payment information and such information can be stored in database 208. The user can be prompted whether or not to store the payment information.

Display 712 can pop up once payment verification is received by a merchant device (e.g., merchant device 204), a payment issuer (e.g., payment issuer 302), and/or a cloud service (e.g., cloud service 402). A user can show a merchant the verification as evidence that a payment for one or more items was made.

FIG. 8 illustrates another user interface 800 for additional or alternative functions of user device 202 and/or exemplary electronic communication and payment systems, such as those described herein. User interface 800 is similar to user interface 700, but user interface 800 does not include an option for add-on items. In addition, interface 800 includes a window 804 that allows a user to select a function, such as order, get in line, pay it forward, pay it backward, pay now, or the like. Displays 802, 806, 808, and 810 can be the same as or similar to displays 702, 704, 710, and 712. Display 806 options can depend on the function selected with display 804.

In the example illustrated in FIG. 8, device 202 can be used to place a customer in a queue by selecting "put me in line." For example, if a merchant typically has a long waiting line, a user can use user device 202 and application 206 to communicate with the merchant—e.g., using merchant device 204 to indicate that the user desires to be in a queue.

By way of example, a user can be put on a wait list from a remote location using user device 202. The list can be adjusted (the user moving down the list) if the user's arrival time (e.g., based on the user's device's GPS location) is less than X (e.g., 30, 20, 10, 5, or the like) minutes away from the merchant or moved up on a list if the user is more than x minutes away from the merchant.

In accordance with some exemplary embodiments, a user's device (e.g. user device 202) can be used in a manner similar to a pager. Many restaurants use a pager that is given to patrons to signal the customers when their tables are ready. In accordance with some embodiments of the disclosure, merchant device 204 can transmit a signal to user device 202—either directly or indirectly—to notify the user that the table (or item) is ready. A pop-up, message, vibration, or other suitable technique may be utilized to inform the user, as desired.

FIG. 9 illustrates another user interface 900 that can be used, for example, for a pull-up service. User interface 900 is similar to user interface 700, but user interface 900 is simplified and does not include an option for add-ons (but in other examples a user interface may include such a display) or alternative payment options. In addition, user interface 900 includes a window 904 that allows a user to select a function, such as order now, get in line, pay it forward, or the like. Displays 902, 906, 908, and 910 can be the same as or similar to displays 702, 704, 710, and 712. The user interfaces illustrated herein are merely for presenting various examples; the invention is not limited to the specific examples shown. For example, various combinations of exemplary displays are considered to be within the scope of this disclosure.

Systems and methods according to the invention may also, once a merchant is selected, prompt the user to either order the same item as previously purchased, or as purchased most frequently, or both, and/or prompt the user to modify the order or select another item.

Additionally, any system or method according to aspects of the invention may include a database, or access one or more databases associated with the user's health. Available information associated with the user's health may include weight, age, medical conditions (such as diabetes, high blood pressure, or heart condition), and/or a diet program. The system may communicate with databases such as the individual's electronic health records, EMR (electronic medical record) and/or PHR (personal health record). The application can match this information with information related to food items, such as blood sugar level, diabetes, high blood pressure, heart condition, and information, such as the sugar amount, salt amount, vitamin amount, contents, cholesterol amount, fat amount or starch amount available from a merchant and suggest items based on the user's medical condition and other factors, such as time of day.

The system is smart and updates over time depending upon the new information it receives, for example based on system updates, new and/or additional data regarding a user or a merchant, and/or the like. In some exemplary embodiments, for example when application 206 is utilized to order a beverage, application 206 may monitor and/or note when the user actually picked up the beverage order. Future orders placed with that merchant may take into account lead times for order pickup based on historical lead time information.

For example, user device 202 and/or application 206 may contact a merchant which supplies food items. Based on the information available to the application or device (for example, a user location), and an analysis of the available food items from the merchant and the user's health condition, the device may display a message such as "I see that you are at (or are ordering from) restaurant X. May I suggest meal Y, which has 500 calories and costs $5.75 plus tax?" The user then has the option to select that item or request to review different items from the merchant's menu.

In certain exemplary embodiments, via operation of application 206, user device 202 may be operative to automatically make a location-based payment, for example an access payment for a toll-road. As user device 202 approaches and/or passes an electronic toll sensor, application 206 may prompt the user to confirm that they would like to pay the toll. In some embodiments, application 206 may be configured to automatically pay a toll on behalf of the user, for example via utilizing one or more of the networks and/or techniques disclosed above.

As will be appreciated by one of ordinary skill in the art, the system may be embodied as a customization of an existing system, an add-on product, a processing apparatus executing upgraded software, a standalone system, a distributed system, a method, a data processing system, a device for data processing, and/or a computer program product. Accordingly, any portion of the system or a module may take the form of a processing apparatus executing code, an internet-based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

Exemplary systems and methods are described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, may be implemented by computer program instructions operative on computer hardware.

Via application of principles of the present disclosure, operation of user device 202 may be improved. For example, via operation of application 206, a user may spend less time utilizing user device 202 searching for directions, searching for suitable restaurants, reviewing electronic menus, and/or the like, thus saving battery life on user device 202 and allowing user device 202 to operate for a longer period of time between charges. Additionally, via operation of application 206, electricity use in network 210 and/or at merchant device 204 may be reduced, for example due to streamlining of order processes and/or elimination of redundant and/or inefficient steps. Yet further, the security of operation of user device 202, merchant device 204, and/or network 210 is improved, for example by eliminating the communication to a merchant device 204 of payment card information associated with a user of user device 202. In this manner, fraud and abuse may be reduced.

In various exemplary embodiments user device 202 may comprise and/or be configured to be wearable, adjustable, flexible, conformable, reprogrammable, and/or reconfigurable. For example, user device 202 may utilize a plurality of applications 206. In these exemplary embodiments, principles of the present disclosure may utilize electronic devices and/or methods disclosed in one or more of the following: (i) U.S. Patent Application Publication No. 2013/0066644 entitled "METHODS FOR PERSONAL EMERGENCY INTERVENTION" published on Mar. 14, 2013; (ii) U.S. Pat. No. 8,126,728 entitled "SYSTEMS AND METHODS FOR PROCESSING AND TRANSMITTAL OF MEDICAL DATA THROUGH AN INTERMEDIARY DEVICE" issued on Feb. 28, 2012; (iii) U.S. Patent Application Publication No. 2009/0249443 entitled "METHOD FOR MONITORING THE UNAUTHORIZED USE OF A DEVICE" published on Oct. 1, 2009; (iv) Jeroen van den Brand, et al., "Flexible and Stretchable Electronics for Wearable Health Devices" in *Solid-State Electronics* 113 (2015), pp. 116-120; (v) Michael P. Gaj, et al., "Organic light-emitting diodes on shape memory polymer substrates for wearable electronics" in *Organic Electronics* 25 (2015), pp. 151-155; (vi) Yang Gao, et al., "Crack-Insensitive Wearable Electronics Enabled Through High-Strength Kevlar Fabrics" in *IEEE Transactions on Components, Packaging and Manufacturing Technology* (Vol. 5, Issue 9, September 2015) pp. 1230-1236; (vii) Douglas Hackler, et al., "Enabling Electronics With Physically Flexible ICs and Hybrid Manufacturing" in *Proceedings of the IEEE* (Vol. 103, No. 4, April 2015); (viii) Wataru Honda, et al., "Wearable, Human-Interactive, Health-Monitoring, Wireless Devices Fabricated by Macroscale Printing Techniques" in *Advanced Functional Materials* (2014, Vol. 24) pp. 3299-3304; (ix) Ryota Tajima, et al., "Truly wearable display comprised of a flexible battery, flexible display panel, and flexible printed circuit" in *Journal of the Society for Information Display* (22/5, 2015) pp. 237-244; and (x) Kuniharu Takei, et al., "Towards Flexible and Wearable Human-Interactive Health-Monitoring Devices" in *Advanced Healthcare Materials* (2015, 4) pp. 487-500. Each of the foregoing references are hereby incorporated by reference in their entirety for all purposes (except for any subject matter disclaimers or disavowals, and except to the extent of any conflict with the disclosure of the present application, in which case the disclosure of the present application shall control).

For example, in various exemplary embodiments, user device 202 may comprise a device that is wearable, flexible, portable, injectable, implantable, and/or otherwise configured to interact with, accompany, and/or be integrated with or coupled to a human body, an item of clothing, an item of furniture, a vehicle, a living space, a public area, a building, an item of infrastructure, and/or the like. Moreover, user device 202 may comprise a variety of electronic components, circuits, and capabilities. In particular, in various exemplary embodiments user device 202 may be updatable, reprogrammable, repurposable, re-usable, and/or otherwise able to be reconfigured and/or revised, for example in connection with specialized software and programming approaches disclosed in connection with FIGS. 11, 12, 13, and 14.

With reference now to FIGS. 11 through 14, advantages of independent software modules that are loadable individually and on demand has long been recognized and widely used on larger computer systems. It provides a high level of flexibility in the range of functionality a particular system can provide. Instead of requiring all functionality to be included in one monolithic code base, the system has access to a large set of modules that are stored somewhere highly optimized for low-cost, long-term storage. By loading modules from this storage into high premium program space only when needed, the system is able to offer extended functionality while keeping the costs for premium resources under control. Using this methodology allows programmability and flexibility that is limited only by the number of modules offered and the amount of long-term storage space available to store them on. Most standard operating systems from mainframes to PC's and smartphones are based on this basic principle.

Although this approach is widely used on larger systems, lightweight embedded systems (for example, certain exemplary embodiments of user device 202) may lack the resources and level of hardware support required to implement this type of architecture. Prior implementations that support loadable modules heavily rely on the presence of large amounts of code and data memory and built-in hardware support like an MMU (Memory Management Unit) to provide virtual addressing capabilities. Although the costs for processors continue to fall while capabilities increase, the tradeoff between higher end processors vs. lightweight solutions continues to persist as factors such as cost, power consumption and size remain factors in design decisions for products that are always expected to do more for less: less money, less battery power and smaller form factors, particularly for Internet of Things (IoT) and wearable devices.

As a result, most embedded systems that are designed around lightweight processors typically offer very limited and linear functionality. Lacking capabilities as described above, the firmware is implemented as one large monolithic system with functionality dedicated to a few main tasks and no ability to extend or change services without reprogramming the entire code base (and then only when the device is actually able to update the firmware).

In contrast, exemplary principles, systems, and methods disclosed herein allow certain lightweight systems to implement programmability and improved and varied performance through loadable modules without the need for resources and capabilities only present on larger processor systems.

Figure 11:
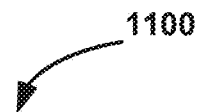
FIG. 11 illustrates an Executable and Linkable Format file as known in the art.

With continued reference to FIG. 11, although each processor manufacturer provides proprietary solutions, development environments and additional tools to aid in development of embedded devices around their products, nearly all rely heavily on, or at least support, the use of the GNU toolchain to perform code compilation and linking into binary images suitable for execution on a target system. A large variety of toolchain builds are available, targeting many processor architectures for many different types of operating systems. The most common output format produced by such tools is ELF (Executable and Linkable Format). A typical (simplified) structure of an ELF file 1100 is shown in FIG. 11. Although ELF file 1100 may contain all the information needed to load and relocate a program image into memory, the format itself is not particularly designed for, nor suitable for, use in lightweight systems. Accordingly, exemplary principles, systems, and methods of the present disclosure are configured to utilize ELF file 1100 as an input, in order to create a new format and new approach that is suitable for certain lightweight embedded systems, such as certain instances of user device 202. It will be appreciated that this problem and solution are inextricably tied to certain specialized computer technology, and cannot be performed on pen and paper or as a purely mental process. Moreover, the exemplary approaches disclosed herein improve the functioning of a computing device by offering expanded functionality with limited computing resources. Yet further, the exemplary approaches disclosed herein improve other industries, for example by limiting the amount of industrial waste needlessly produced to generate high-performance processing components such as memory management units, when principles of the present disclosure allow such components to be eliminated.

When a binary image is built, standard linkers will typically target the image to be loaded at a particular code and data address. Unless a true position independent image is produced, loading the image in any other location without additional processing will prevent the image from executing properly. However, depending on memory usage and characteristics, these physical locations may not be available at module load time. On larger systems, this discrepancy can often be resolved simply by mapping actual physical addresses to the expected locations through the virtual memory mapping capabilities of the MMU. However, this option may not always be a suitable solution, even when an MMU is present. In these instances the actual content of the code and/or data segments of the image need to be modified to adjust for the address changes, a process called relocation. When relocation will be required, the ELF file will contain all the information needed to perform the actual relocation process. Larger systems will typically load the entire code and data segment directly into RAM and subsequently enumerate through the relocation sections to determine how and where address fix ups need to be performed and make the corresponding changes in the code and data locations in RAM accordingly. Once relocation has completed, the RAM section containing the code will be configured for code execution (if applicable) and control is passed to the entry location in the image as specified in the ELF file 1100. For optimization purposes, certain systems may not load the entire image at once but rather page by page on an as needed basis. However, the basic relocation process remains the same.

In contrast, in various exemplary embodiments user device 202 comprises a lightweight system, for example with limited processing capabilities, limited RAM, limited flash memory, no MMU, and so forth. In order to produce a solution suitable for this environment, exemplary systems and approaches disclosed herein are able to take full advantage of this available code space and offer the ability to load modules into flash (hence the term "Flash Loadable Modules").

Given that code and data space is often at a premium in lightweight systems, an important consideration is the ability of exemplary systems and approaches to be able to make efficient use of the available flash and RAM space, for example in a user device 202. The ability to load binary modules freely at any memory location, regardless of the initial target addresses used during build time, is highly desirable. Since the amount of memory in user device 202 may be relatively small, user device 202 may lack an MMU unfortunately (which eliminates the relatively straightforward virtual-to-physical address mapping methods as an option to compensate for location changes). Instead, exemplary systems and methods perform customized relocation processing in order to load a binary image at a different address.

Figure 12:
FIG. 12 illustrates a Flash Loadable Module file format in accordance with exemplary embodiments of the disclosure.
Figure 12:
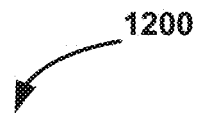
Figure 13:
FIG. 13 illustrates a Flash Loadable Module file format in accordance with exemplary embodiments of the disclosure.

With reference now to FIGS. 12 and 13, in various exemplary embodiments a software application and/or related methods are configured to transform an ELF file 1100 into a Flash Loadable Module (FLM) file via a flash linker. An exemplary format for a FLM file 1200 is shown in FIG. 12. Another exemplary format for a FLM file 1300 is shown in FIG. 13.

Figure 14:
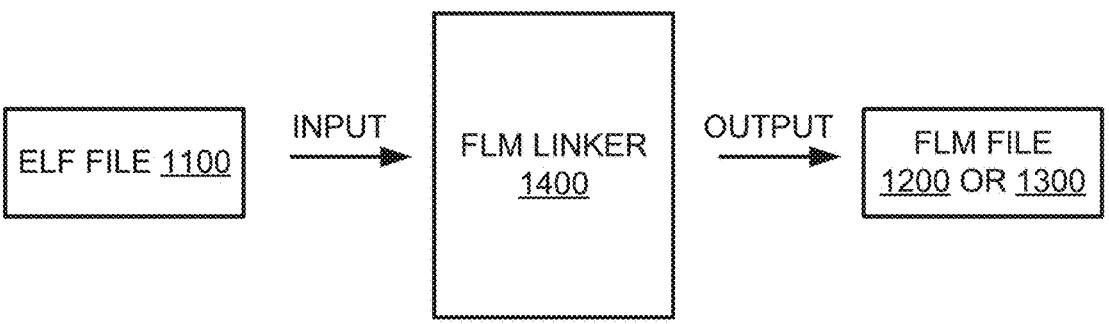
FIG. 14 illustrates creation and use of a Flash Loadable Module file format in accordance with exemplary embodiments of the disclosure.
Figure 14:
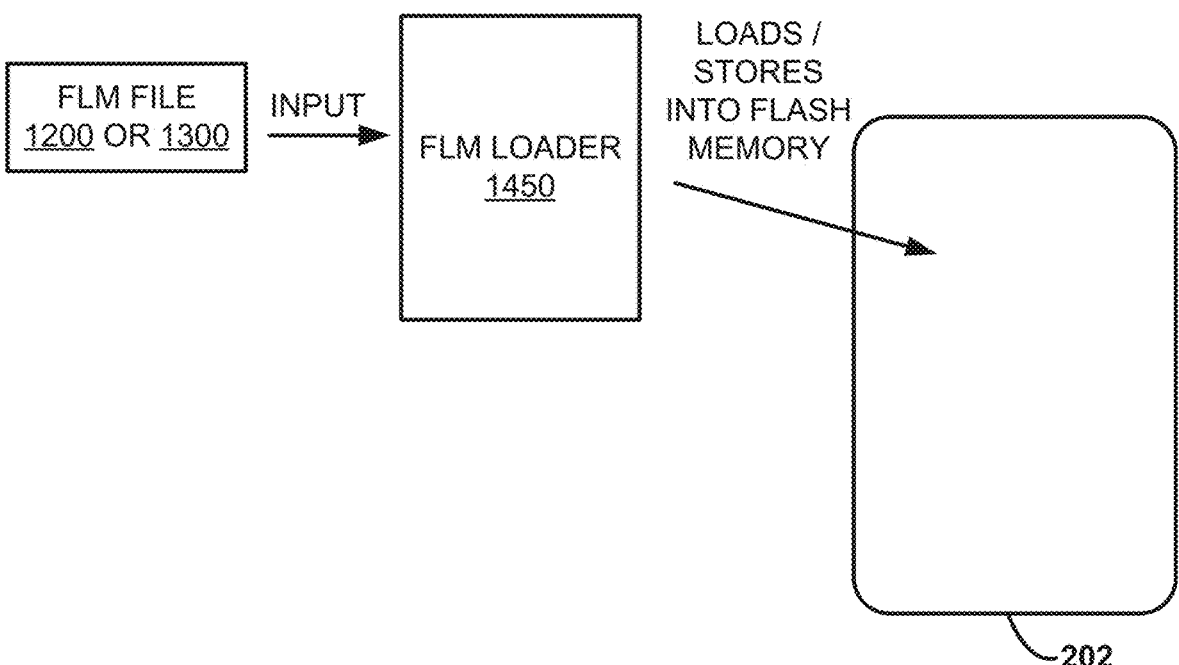

With reference to FIG. 14, in an exemplary embodiment, a flash linker 1400 is configured to convert a regular ELF file 1100 to an FLM file 1200, which is much more suitable for loading binary images into flash memory on embedded systems with limited resources, such as certain embodiments of user device 202. Flash linker 1400 collects all the relevant relocation entries from all sections in ELF file 1100 and orders them by relocation address. Flash linker 1400 subsequently breaks the code segment into blocks based on a configurable block size and groups each block with all relocation entries pertaining to that block. All groups are subsequently written to an FLM file 1200, following an FLM header. In FLM file 1200, the relocation entries for the data segment are also grouped together but the segment itself is not split into blocks since the data can be loaded directly into RAM and relocated in-place. The resulting FLM file is generally formatted as shown in FIG. 12. In these exemplary embodiments, it can be seen that the combined size of a code block (i.e., 1 through N) and its corresponding relocation information are of a fixed size.

In various exemplary embodiments, the FLM header contains details about the ROM and RAM regions the binary image was originally built for, while the segment headers indicate information such as segment type, location, size and number of following blocks. In FLM file 1200, the code segment header is followed by code sections where each section consists of the actual code block and code relocation entries. Flash linker 1400 ensures that the combined size of a section does not exceed a specified size, making the code block smaller if more relocation entries are present. This allows lightweight embedded systems, for example certain embodiments of user device 202, to allocate a RAM buffer of predefined fixed size, load each code section into the buffer and use the entries in the buffer to relocate the content of the code block. When completed, the modified code block can be written directly to a flash buffer and the embedded loader can move on and read in the next section. The same process is followed for the data section except that the RAM buffer is bypassed and the data block written directly to the target region in RAM and relocation is performed in-place.

In some exemplary embodiments, user device 202 may be configured as an embedded system that does not utilize an intermediate RAM buffer, but rather utilizes a designated flash buffer directly. A flash buffer is a region of RAM that matches the exact size of a flash write page and is used to read, modify and write back to flash in order to update non-page aligned content. In these exemplary embodiments, FLM linker 1400 may produce an FLM file 1300 wherein the block size is fixed rather than the section size, producing a format as illustrated in FIG. 13. In these exemplary embodiments, it can be seen that code blocks 1 through N are of equal size, while the corresponding relocation information is of a variable size. When the code block size matches the size of the flash buffer in user device 202, the embedded module loader can write the code block directly into the flash buffer and read to subsequent code relocation entries to perform relocation directly in this buffer. Once completed, the buffer content can be written to flash after, which the loader can load in the next code block from the FLM file.

Once an FLM file (e.g., 1200, 1300, and/or the like) is created, it may be loaded into the flash memory of user device 202, for example via operation of FLM loader 1450. In this manner, user device 202 may be provided with a variety of functions, depending on the contents of the FLM file. Various functions which may be programmed into user device 202 in this manner are disclosed in the following Example Sets.

In some exemplary embodiments, FLM loader 1450 is external to user device 202. In other exemplary embodiments, FLM loader 1450 is internal to user device 202. FLM loader 1450 may comprise any suitable software and/or hardware components configured to write data to flash memory of user device 202 as disclosed herein.

Figure 15:
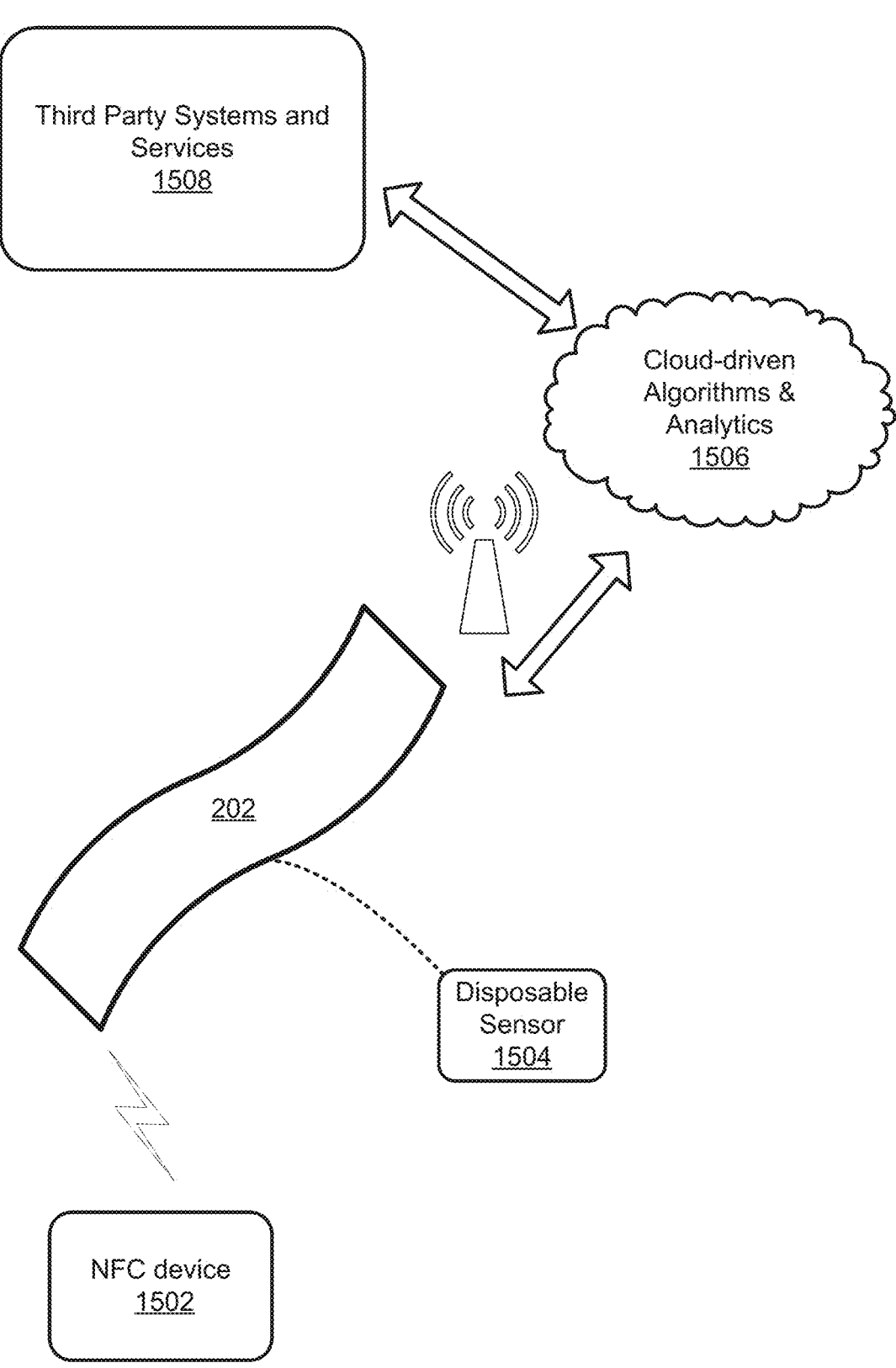
FIG. 15 illustrates an exemplary user device and related capabilities and systems in accordance with exemplary embodiments of the disclosure.

With reference now to FIG. 15, in various exemplary embodiments a user device 202 is configured with various sensors, indicia, communication capabilities, and/or the like. In an exemplary embodiment, user device 202 comprises a microphone, a haptic vibration element, a buzzer, various buttons and switches, a display, and the like. User device 202 may be worn, for example on a wrist, ankle, or so forth. User device 202 may measure galvanic skin response (for example, in order to evaluate stress, hydration, etc.). Moreover, user device 202 may comprise a six axis accelerometer for use in fall detection, activity monitoring, step counting, sleep monitoring, calorie burning, and the like. Yet further, user device 202 may include a rechargeable battery that may be recharged via inductive coupling. Additionally, user device 202 may comprise a temperature sensor to measure ambient temperature, body temperature, and so forth. Various indicators and screens, for example LEDs, may display information about heart rate, heart rate variability, oxygen saturation (SpO2), and so forth.

With continued reference to FIG. 15, in various exemplary embodiments a user device 202 may be configured to interface with and/or interact with various other components and systems to implement desired functionality and/or capabilities. For example, user device 202 may wirelessly communicate with one or more nearby NFC devices 1052. NFC device 1502 may provide various supplementary functionality to user device 202, for example an immunoassay on a disposable NFC-enabled chip. Moreover, user device 202 may be configured with one or more access ports, snap-in couplings, and/or the like, in order accommodate integration with various disposable sensors 1504. Disposable sensors 1504 may be configured for one time use (or repeated use) to monitor or detect a particular condition, substance, or the like, for example environmental sensors, medical sensors, or other exemplary sensors disclosed in the following Example Sets. Information from NFC device 1502, disposable sensor 1504, and/or the like may be transmitted to user device 202 and from there to various cloud-based evaluation, assessment, and/or analytics services 1506 (which may, in turn, send various information, reports, alerts, warnings, reminders, and/or the like back to user device 202). For example, services 1506 may monitor and/or evaluate blood pressure, ECG, SpO2, skin temperature, hydration level, movement, impact, and/or the like.

Services 1506 may interface with local software on devices other than user device 202, for example tablet software utilized by caregivers, in order to facilitate interaction with and/or care for a user of user device 202. Moreover, services 1506 may interface with systems and services provided by third parties, for example emergency medical services, in order to provide actionable data about a user of user device 202. Services 1506 may also be utilized to revise, update, replace, and/or supplement the capabilities of user device 202, for example via providing updated functionality applications over a wireless connection to user device 202 as disclosed herein. In some exemplary embodiments, these functionality applications may take the form of an FLM file 1200 and/or 1300, as desired.

In various exemplary embodiments, user device 202 may be utilized (for example, in connection with services 1506), to provide an extensible platform of services and capabilities to a user. For example, in connection with automation, user device 202 may be utilized as a controller to control a television, lights, thermostats, and the like. User device 202 may act as a beacon for positional awareness of a user of user device 202.

Moreover, in connection with security and authentication, user device 202 may be utilized, for example, to: arm or disarm an alarm system; operate as a personal emergency response system; provide attack or fall detection; provide geofencing; act as a lost and found aid; provide location of a person; authenticate and/or enable use of a weapon; operate as a pass key for a hotel room, garage, event, or the like; act as an airline ticket and/or biometric security authentication; unlock a personal electronic device, such as a cell phone, tablet, learning thermostat, or the like; provide tap communication capabilities, such as tap and pair, provide network authentication capabilities, and so forth.

Yet further, in connection with healthcare and fitness, user device 202 may be utilized, for example, to: track medication adherence; communicate with biometric devices such as a scale, blood pressure measurement system, glucometer, pulse oximeter, or the like; store personal health records, personal health information, or genetic information; coordinate gym workouts, such as preset equipment settings, workout records; provide activity tracking, such as exercise, steps, calories, sleep, and so forth; provide hospital and/or home healthcare identification or access; provide digital nutrition delivery, and so forth.

Still further, in connection with vehicles, user device 202 may be utilized, for example, to: lock or unlock doors; provide driver identification; provide driver warnings (over center line, following too close, etc.); integrate with a vehicle navigation system, and so forth.

In various exemplary embodiments, for example as disclosed hereinabove, user device 202 may be utilized in connection with mobile payments to enable electronic wallet and ticketing capabilities, point of purchase payments, event entrances, and so forth.

User device 202 may be utilized as and/or in connection with an attached disposable sensor (e.g., for ovulation monitoring, diabetes monitoring, etc.), a tremor monitor, a stress monitor, and/or point of care diagnostics.

In various exemplary embodiments, user device 202 may be utilized in connection with services 1506 to provide remote point of care diagnostics capabilities. For example, a series of diagnostic tests may be ordered at a point of care for a patient associated with user device 202. Appropriate software for the diagnostic tests (for example, formatted as an FLM file 1200 or 1300) may be sent to user device 202 via services 1506. The software is loaded onto user device 202 and the tests are performed (for example, in connection with one or more of disposable sensor 1504, NFC device 1502, or the like). The results are transmitted back to the ordering system/clinician via services 1506. Based on the results, the ordering system/clinician may order additional tests or treatment, add or remove functionality to user device 202, and/or the like. Trends and other changes in tests over time may be reviewed and assessed. In this manner, improved diagnostic capabilities and follow up are achieved.

It will be appreciated that, via interaction of user device 202 with services 1506, various third-party systems and services 1508 may provide services to user device 202 and/or a wearer thereof. For example, health care providers, financial services providers, and the like may desirably interact with a user of user device 202 via the functions and capabilities described herein.

Examples of various exemplary embodiments embodying aspects of the invention are presented in the following Example Set I. It will be appreciated that all the examples contained in this disclosure are given by way of explanation, and not of limitation.

Examples of the Invention. Example 1: A device for being attached to a person, the device comprising: (a) band including electronic circuitry, a first power source, and a display; and (b) the band, electronic circuitry and display being flexible so as to be functional when manipulated into a circle having a diameter of 4" or more, 5" or more, 6" or more, 7" or more, 8" or more, 9" or more, or 10" or more. Example 2: The device of example 1 that can be manipulated into a circle leaving a diameter of 4" to 10". Example 3: The device of any of examples 1-2 that has a thickness of ¼" or less. Example 4: The device of any of examples 1-2 that has a thickness of ⅛" or less. Example 5: The device of any of examples 1-2 that has a thickness of ³⁄₁₆" or less. Example 6: The device of any of examples 1-5 that has a width of 2" or less, or 1½" or less, or 1" or less or ¾" or less. Example 7: The device of any of examples 1-6 wherein the power source is a battery. Example 8: The device of example 7 wherein the battery is rechargeable. Example 9: The device of any of examples 1-8 that includes a second power source that provides power when the first power source is drained. Example 10: The device of example 9 wherein the second power source is a primary battery or a secondary battery.

Example 11: The device of any of examples 1-10 that includes a solar cell that recharges the primary power source and/or the secondary power source. Example 12: The device of any of examples 1-11 that connects to a solar cell that recharges the primary power source and/or the secondary power source. Example 13: The device of any of examples 1-12 wherein the circuitry can be flexed into an arc of a circle having a diameter of between 5" to 25" or more. Example 14: The device of any of examples 1-13 wherein the circuitry is 50% or less of the length of the band, or 80% or less of the length of the band. Example 15: The device of any of examples 1-14 wherein the circuitry has a thickness of 25% of the band or less, or 25%-50% of the band, or 75% of the band or less. Example 16: The device of any of examples 1-15 wherein the circuitry has a width of 90% of the width of the band or less, or between 50% and 80% of the width of the band, or between 80% and 100% the width of the band. Example 17: The device of any of examples 1-12 wherein the display can be flexed into an arc of a circle having a diameter of between 5" to 25" or more. Example 18: The device of any of examples 1-13 wherein the display is 50% or less of the length of the band, or 80% or less of the length of the band. Example 19: The device of any of examples 1-14 wherein the display has a thickness of 25% of the band or less, or 25%-50% of the band, or 80% of the band or less. Example 20: The device of any of examples 1-15 wherein the display has a width of 90% of the width of the band or less, or between 50% and 80% the width of the band, or between 90%-100% the width of the band.

Example 21: The device of any of examples 1-20 that is configured to be worn on a wrist. Example 22: The device of any of examples 1-20 that is configured to be worn on either the arm, the leg, or the torso. Example 23: The device of any of examples 1-20 that is a belt or part of a belt. Example 24: The device of any of examples 1-20 that is a watch or part of a watch. Example 25: The device of any of examples 1-20 that is jewelry or part of jewelry. Example 26: The device of any of examples 1-25 that can measure heart rate. Example 27: The device of any of examples 1-26 that can measure blood oxygen. Example 28: The device of any of examples 1-27 that can measure perspiration. Example 29: The device of any of examples 1-28 that can measure electrical resistance on the skin by directing a current across at least part of the skin. Example 30: The device of any of examples 1-29 that includes at least one accelerator.

Example 31: The device of any of examples 1-30 that can measure blood pressure. Example 32: The device of any of examples 1-31 that includes a thermometer to measure the temperature of the wearer. Example 33: The device of any of examples 1-32 that includes a thermometer to measure air temperature. Example 34: The device of any of examples 1-33 that includes a clock. Example 35: The device of any of examples 1-34 that includes a calendar. Example 36: The device of any of examples 1-35 that includes a GPS locator. Example 37: The device of any of examples 1-36 wherein the display can be lit. Example 38: The device of any of examples 1-37 that includes multiple displays. Example 39: The device of any of examples 1-38 that includes multiple circuitries. Example 40: The device of any of examples 1-39 that includes multiple first power sources.

Example 41: The device of any of examples 1-40 that measures physical steps taken by the wearer. Example 42: The device of any of examples 1-41 that measures physical distance walked, run, or biked by the wearer. Example 43: The device of any of examples 1-42 that includes analog controls and/or digital controls. Example 44: The device of any of examples 1-43 that includes a touch screen, the touch screen displaying commands to assist in controlling the device. Example 45: The device of any of examples 1-44 that estimates calories used by a wearer. Example 46: The device of any of examples 1-45 that communicates with a cellular phone or other handheld device. Example 47: The device of any of examples 1-46 that communicates with a computer. Example 48: The device of any of examples 1-47 that suggests a first activity on the display based on the date and time. Example 49: The device of example 48 wherein the first activity can be selected or rejected by the wearer through the use of a control. Example 50: The device of example 49 that suggests a different activity if the first activity is rejected.

Example 51: The device of any of examples 1-50 wherein the wearer can select among multiple activities in which to participate. Example 52: The device of any of examples 1-51 that is connected to a database of past activities of the wearer, the database including the activity, date and time of the activity, and optionally the duration of the activity. Example 53: The device of example 52 wherein the database can be updated or changed manually by the wearer. Example 54: The device of example 52 or 53 wherein the database is updated automatically based upon activity by the wearer. Example 55: The device of any of examples 1-54 that includes an alarm to remind the wearer of an activity. Example 56: The device of example 55 wherein the alarm is one or more of an audio alarm, a visual alarm, or physical alarm. Example 57: The device of example 56 wherein the physical alarm is vibration. Example 58: The device of any of examples 1-57 that identifies the wearer based on (a) entering an identification code, (b) fingerprint recognition, and/or (c) other biometric information. Example 59: The device of any of examples 1-58 that activates one or more of the wearer's (a) home and/or development gate code, (b) automobile ignition, (c) garage door, (d) cellular phone, (e) computer, (f) entrance door, and/or (g) security alarm, when the device is within a predetermined proximity. Example 60: The device of example 59 wherein the predetermined proximity is between 6" and 30'.

Example 61: The device of any of examples 1-60 that operates a television set or a television set control when in a predetermined proximity to the set or control. Example 62: The device of any of examples 1-61 wherein the wearer can select or reject an activity, or otherwise send a communication from the device, by movements that move the device. Example 63: The device of any of examples 59-62 wherein the wearer can activate another device, such as a gate, television, television control, automobile door, lock or ignition, cell phone, computer, security system, garage door, or entrance door, by movements that move the device. Example 64: The device of any of examples 1-63 that contacts an emergency center and provides the wearer's location if it senses an emergency. Example 65: The device of example 64 wherein the emergency can be one or more of (a) a sudden impact, (b) unstable or lack of heart beat, or (c) unstable or lack of blood pressure. Example 66: The device of any of examples 1-65 that communicates with advertising signals in a store to customize electronic advertising in the store for the wearer. Example 67: The device of any of examples 1-66 that is water resistant. Example 68: The device of any of examples 1-67 that can withstand an impact force of 5 lbs or more, or 10 lbs or more, or between 20 lbs and 25 lbs, or between 25 lbs and 30 lbs. Example 69: The device of any of examples 1-68 that further includes a transmitter and a receiver. Example 70: The device of any of examples of 1-69 that further includes: (a) connectivity to a database; (b) a wearer input; (c) a transmitter; and (d) a wearer application, wherein the wearer application stores information about one or more merchants and order information associated with one or more merchants.

Example 71: The device of example 70 wherein the wearer can transmit an order to a merchant from the device utilizing the information. Example 72: The device of any of examples 1-71 that further comprises a database. Example 73: The device of any of examples 70-72 wherein the database stores at least two of (a) one or more merchant names, (b) one or more items previously purchased or ordered from the one or more merchants, (c) the prices of the items previously ordered or purchased, (d) the location of the one or more merchants, and (e) offers by the one or more merchants for the sale of items. Example 74: The device of any of examples 70-73 that includes a wearer application wherein the wearer application determines the proximity of the device to one or more merchants. Example 75: The device of example 74 that displays the proximity. Example 76: The device of any of examples 74 or 75 wherein the one or more merchants are selected from merchants previously visited by the wearer. Example 77: The device of any of examples 74-76 wherein the one or more merchants are selected from one or more merchants that participate in a program. Example 78: The device of any of examples 1-77 wherein the device displays a merchant and most-frequent order information corresponding to the merchant. Example 79: The device of any of examples 1-78 wherein a wearer can place an order for an item or service using the device. Example 80: The device of example 79 wherein the item or service ordered is stored in the database.

Example 81: The device of any of examples 79-80 wherein the wearer is prompted to pay for the item or service. Example 82: The device of any of examples 70-81 wherein one or more payment sources are stored in the device, or in the wearer application where they are accessible by the device. Example 83: The device of any of examples 70-81 wherein the one or more payment sources are stored on a server separate from the device and wearer application. Example 84: The device of any of examples 70-81 wherein the device initiates a payment to the merchant for an item or service. Example 85: The device of any of examples 70-84 wherein the device is connected to a payment issuer. Example 86: The device of example 85 wherein the payment issuer issues a payment to the merchant. Example 87: The device of example 84 or 85 wherein the payment issuer is one of a payment network and a bank. Example 88: The device of any of examples 85-87 wherein the payment issuer issues a payment verification to the device. Example 89: The device of example 88 wherein the payment issuer issues a payment verification to the merchant. Example 90: The device of example 89 wherein the merchant device or the payment issuer transmits a payment verification to the device.

Example 91: The device of any of examples 70-90 wherein the wearer application comprises a pay-it-forward function. Example 92: The device of any of examples 70-91 wherein the wearer application comprises a pay-it-backward function. Example 93: The device of any of examples 70-92 wherein the wearer application comprises a "get in queue" function. Example 94: The device of any of examples 70-93 wherein the wearer application is not resident on the device. Example 95: The device of any of examples 70-94 wherein the database is not resident on the wearer application or on the device. Example 96: The device of any of examples 70, 71 or 74 wherein the application or the device communicates with a separate, second database. Example 97: The device of any of examples 70-96 wherein the wearer application or the device calculates the time it will take for an order to be ready, and the time is displayed on the device. Example 98: The device of any of examples 70-97 wherein the merchant transmits a signal with the time the order will be ready, and the time is displayed on the device. Example 99: The device of any of examples 70-98 wherein the device displays a merchant and most-recent order information corresponding to the merchant. Example 100: The device of example 79 wherein the database is updated by the item ordered being stored in the database.

Example 101: The device of any of examples 70-81 wherein the merchant transmits the price of the item, and the price is displayed on the device. Example 102: The device of example 88 wherein the payment verification sent to the merchant does not include the wearer's card number or bank account number. Example 103: The device of example 102 wherein the payment verification sent to the merchant does not include the wearer's card expiration date, billing address, or CVV number. Example 104: The device of any of examples 70-103 that further accesses one or more of (a) the time of day, day of the week, day of the year, month, and/or year, (b) health information related to the wearer, and (c) information related to the nutritional aspects of one or more food items. Example 105: The device of example 104 wherein the one or more of (a)-(c) is stored in the wearer application, which is either included in the device or is separate from the device. Example 106: The device of example 104 wherein the one or more of (a)-(c) is stored in one or more separate databases accessible by the wearer application, or by the device. Example 107: The device of any of examples 104-106 wherein the health information of the individual includes one or more of the wearer's weight, age, measured blood sugar level, measured blood pressure, heart condition, whether the wearer is diabetic, whether the wearer has high blood pressure, and whether the wearer is pregnant and the stage (by days or weeks) of the pregnancy. Example 108: The device of any of examples 104-106 wherein the information related to a food item includes one or more of (a) its ingredients, (b) the amount by weight of each ingredient, (c) its calories, (d) carbohydrate content, (e) vitamin content, (f) fat content, and (g) sugar content. Example 109: The device of any of examples 104-106 that compares the wearer's health information to the information related to one or more food items, and the device displays one or more suggested food items. Example 110: The device of any of examples 1-109 that adds new information and updates a database as it is used.

Example 111: A device according to any of examples 1-110, the device connectable to a server having a memory, and further having at least one wearer interface for receiving data from the device, the memory configured to store data received by the device in a file for that wearer. Example 112: The device of example 111 wherein the data further includes one or more of: audio data, text, advertisements, prices, wearer contact information, at least one merchant and items or services related to each merchant. Example 113: The device of any of examples 1-112 wherein data is received wirelessly by the device from a remote source. Example 114: The device of example 113 wherein each data entered by a wearer into the device, or entered automatically by the device, includes the date and time the data was entered. Example 115: The device of any of examples 111-114 wherein the data can be retrieved from the server and displayed on the device. Example 116: The device of any of examples 111-115 wherein the server configures the data to be displayed in one of the following formats: (a) chronologically; (b) by entity that entered the data; or (c) by the type of data. Example 117: The device of any of examples 111-116 that further includes an API in communication with the server wherein the data input device is programmed to send a communication to the API prior to transmitting data and the API is configured to receive the communication to determine a type of the device. Example 118: The device of example 117 that further includes an API in communication with the server wherein the data input device is programmed to send a communication to the API prior to transmitting data and the API is configured to receive the communication to determine a type of the device. Example 119: A system including a server and multiple devices. Example 120: The system of example 119 wherein at least one of the multiple devices transmits data in a format different than the format used by the other of the devices.

Example 121: The system of example 119 or 120 wherein each device for a specific wearer includes unique identification indicia specific to that wearer. Example 122: The device or system of any of examples 1-118 that further includes at least one receiving device remote from a server. Example 123: The device of any of examples 1-118 wherein information transmitted to the device includes one or more of: (a) an advertisement; (b) a price; and (c) contact information for a merchant, such as a phone number, SMS address, email address, and/or physical address.

Example 124: A system for facilitating use of a device, the system comprising: a network; the device having an application, the device coupled to the network; wherein the application allows a wearer to transmit information documenting proposed services or items to be provided or purchased; wherein the application displays information regarding the proposed services or items on the device; and wherein the wearer can use the application to contact a merchant or caregiver in response to the proposed services or items. Example 125: The system of example 124 further comprising a database coupled to the network, wherein the database comprises wearer information. Example 126: The system of example 125 wherein the device further comprises a web services server and the database forms part of the web services server. Example 127: The system of example 125 wherein wearer information comprises contact information, such as phone number, email address, and/or physical address. Example 128: The system of example 125 wherein wearer information comprises at least one charge account identification number. Example 129: The system of any of examples 124-128 further comprising a streaming server coupled to the network. Example 130: The system of example 129 wherein the streaming server comprises a streaming server application.

Example 131: The system of example 129 wherein the streaming server application determines a communication bandwidth of the network. Example 132: The system of any of examples 129-131 wherein the streaming server application determines an operating system of the device. Example 133: The system of any of examples 124-132 wherein the wearer application sends a notification to the server when the device displays information regarding proposed services or items. Example 134: The system of any of examples 124-133 wherein the information comprises a history of related services. Example 135: The system of any of examples 124-133 further comprising a step of sending to the device a cost of the services or items. Example 136: Any of the devices or systems of examples 1-135 that further includes a microphone and speaker as part of the device, or that are connectable to the device. Example 137: Any of the devices or systems of examples 1-136 that further includes an emergency signal on the device that can be activated by the wearer to summon help. Example 138: A device configured to communicate with one or more servers that contains data specific to the device wearer, the device being configured to receive the data via email, SMS, or other wireless communications protocol. Example 139: The device of example 138 that includes an operating system and software on the operating system that configures the device to communicate with the one or more servers. Example 140: The device of examples 138 or 139 wherein an alert is received when new data is displayed on the device.

Example 141: The device of any of examples 138-140 wherein, if the data includes a recommended purchase, the recommended purchase may be accepted by activating an icon or rejected by activating a different icon. Example 142: The device of any of examples 138-141 wherein in addition to the recommended purchase, contact information regarding a merchant is provided. Example 143: The device of example 142 wherein the contact information includes one or more of a phone number, an email address, an SMS address, and a physical address. Example 144: The device of any of examples 138-143 that communicates with the one or more servers or an API communicating with the one or more servers. Example 145: The device of any of examples 138-144 that can locate merchants based on the device location and the merchant location. Example 146: The device of any of examples 138-145 that can locate merchants based on the services or items desired by the device wearer. Example 147: The device or system of any of examples 1-146 wherein the device further includes a camera. Example 148: The methods performed, respectively, by each of examples 1-147. Example 149: The device, system or method of any of examples 1-148 wherein the device communicates using one or more of a NFC signal, Bluetooth signal, Wi-Fi signal or Zigbee protocol. Example 150: The device, system or method of any of examples 1-149 that is connectable to a separate power source.

Example 151: The device, system or method of any of examples 1-150 that communicates directly with a wireless cellular network. Example 152: The device, system or method of any of examples 1-151 that further includes a docking station, the docking station for receiving the device and transmitting information from the device to an application, server, intermediary device, or database. Example 153: The device, system or method of example 152 wherein the transmitting is done wirelessly. Example 154: The device, system or method of any of examples 1-153 that includes a command server, the command server for sending one or more commands to the device to activate a function of the device. Example 155: The device, system or method of example 154 wherein the one or more commands includes (a) identifying the current location, (b) taking a blood pressure reading, (c) measuring heart rate, (d) measuring blood oxygen level, (d) measuring respiration rate, (e) measuring perspiration, (f) taking a photograph, (g) transmitting audio signals, and (h) activating an alarm. Example 156: The device that has a band for attaching to a body part or an article of clothing, but that does not have flexible circuitry or a flexible display. Example 157: The device, system or method according to any of examples 7-155 that includes the device of example 156 rather than the device of examples 1-6. Example 158: The device, system or method according to any of examples 1-157 that stores in a database nutritional information concerning meals available at one or more merchants, and the nutritional information is accessible on the device. Example 159: A device, system or method according to example 158 that includes for each meal one or more of (a) amount of sugar, (b) amount of calories, (c) type and amount of vitamins, (d) type and amount of minerals, (e) amount of soluble fiber, (f) amount of fat, and (g) amount of sodium. Example 160: A device, system or method according to any of examples 1-159 that includes an identification code that verifies the wearer is the owner of one or more secondary devices, such as (a) credit card, (b) mobile phone, (c) computer, or (d) other device, and permits use of the secondary device.

Example 161: A device, system or method according to example 160 that permits use of the secondary device without entering a password. Example 162: A device, system or method according to any of examples 1-159 wherein the wearer can access a database including one or more credit card accounts, select a credit card account, and make a charge to the credit card account using the device. Example 163: A device, system or method according to example 162 wherein the charge is made from the device using NFC to a point of sale terminal. Example 164: A device, system or method according to example 162 or 163 wherein the credit card account number is displayed on the device display. Example 165: A device, system or method according to example 162, 163 or 164 wherein the CVV number of the credit card account number is displayed on the device display. Example 166: A device, system or method according to any of examples 1-165 wherein the device includes a monitoring unit comprising: at least one sensor operatively coupled to a controller, wherein the controller is configured to receive a measured input from the at least one sensor; and a wireless communication device coupled to the controller, wherein the wireless communication device is configured to communicate with a central control system. Example 167: A device, system or method according to example 166 wherein the at least one sensor is one or more of a thermometer, a heart rate monitor, a blood oxygen sensor, an electric resistance meter, a pressure transducer, and an air quality sensor. Example 168: A device, system or method according to any of examples of 166 or 167 wherein the wireless communication device is configured to transmit data from the at least one sensor to the central control system. Example 169: The device, system or method according to any of examples 1-168 that has a wireless communication device that is configured to transmit using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network. Example 170: The system or method according to any of examples 1-169 that includes a plurality of devices.

Example 171: The system or method according to example 170 wherein each of the plurality of devices is configured to communicate with at least one other device of the plurality of devices. Example 172: The device, system or method according to any of examples 166-171 wherein the wireless communication device transmits data to the central control system at regular intervals. Example 173: The device, system or method according to any of examples 166-172 wherein the wireless communication device transmits data to the central control system in response to a measured input exceeding a predetermined threshold. Example 174: The device, system or method according to any of examples 166-173 wherein the wireless communication device transmits data to the central control system when the device detects a short-range transmission signal sufficient to transmit the data. Example 175: The device, system or method of any of examples 1-165 wherein the device transmits data to a server (a) on regular intervals, (b) when requested by the central control system, (c) in the event of a predetermined value being exceeded, (d) when a sufficiently strong wireless signal is determined for transmitting the data, and/or (e) when sent by the device wearer.

Example 176: A patient monitoring system comprising one or more devices on a patient, at least one of the devices being flexible to wrap around part of an arm, leg, head, neck or torso; and receiving, by a monitoring sensor included as part of the device, medical data from the patient; transmitting the medical data to a central control system; and optionally comparing the transmitted medical data to a predetermined level for the patient. Example 177: The patient monitoring system of example 176 wherein the patient data is transmitted to the central control system in real-time. Example 178: The patient monitoring system of example 176 wherein the patient data is transmitted to the central control system in batch form. Example 179: The patient monitoring system of any of examples 176-178 wherein the patient data includes one or more of blood pressure, temperature, heart rate, blood oxygen level, skin electric conductivity, perspiration rate, physical location, air quality, and respiration rate. Example 180: The patient monitoring system of any of examples 176-179 further comprising notifying, by the monitoring unit, the central control system in response to the patient data exceeding a patient data threshold level.

Example 181: The patient monitoring system of example 179 that includes an electrical conductivity meter. Example 182: The patient monitoring system of any of examples 176-181 wherein the wireless communication device is configured to transmit using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network. Example 183: The device, system or method of any of examples 1-182 wherein the device is at least partially powered by a piezo chip. Example 184: The device, system or method of any of examples 1-183 wherein the power source is at least partially recharged by a piezo chip. Example 185: A method according to any device or system of any of examples 1-184 wherein there is a plurality of devices, the method comprising the steps of: receiving data from at least one of the plurality of devices, wherein each of the plurality of devices is in communication with a wearer, and wherein the data comprises medical or personal information about the wearer; transmitting the medical information condition to a first server; and transmitting the personal information to a second server. Example 186: The method of example 185 wherein the plurality of devices includes one or more of a thermometer, pressure transducer, accelerometer, electric conductivity meter, perspiration sensor, heart rate sensor, blood oxygen sensor, respiration rate sensor, and a GPS device. Example 187: The method of example 185 or 186 wherein the data is provided to a monitoring unit by one or more of the plurality of devices. Example 188: The method of any of examples 185-187 wherein the medical and/or personal information is transmitted in real time. Example 189: The method of any of examples 185-187 wherein the medical and/or personal information is transmitted at predetermined times, or when an electrical communications signal sufficient for transmitting the information is detected. Example 190: The method of any of examples 185-189 wherein each of the plurality of devices comprises: at least one sensor operatively coupled to a controller, wherein the controller is configured to receive an input from the at least one sensor; and a wireless communication device coupled to the controller, wherein the wireless communication device is configured to communicate with a central control system. Example 191: The method of example 190 wherein the wireless communication device is configured to transmit using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network.

Example 192: A system comprising: (a) a device, the device comprising a band for being worn on the body of a wearer and further comprising: (i) a processor; (ii) a transceiver coupled to the processor; (iii) a sensor coupled to the processor and configured to measure a characteristic associated with the wearer; and (iv) a non-transitory memory coupled to the processor and storing instructions executable by the processor for: (1) receiving data from the sensor; and (2) transmitting the received data via the transceiver; and (b) a coordinator configured to receive the transmitted data. Example 193: The system of example 192 wherein the transceiver is configured to transmit data using one or more of: a Zigbee protocol, a Wibree protocol, an IEEE 802.11 protocol, an IEEE 802.15 protocol, an IEEE 802.16 protocol, an Ultra-Wideband (UWB) protocol, an Infrared Data Association (IrDA) protocol, a Bluetooth protocol, and combinations thereof. Example 194: The system of example 191 or 192 wherein the transceiver is configured to transmit data through a wired connection selected from the group consisting of an optical fiber connection, a tip and sleeve (TS) connection, a tip, ring, and sleeve (TRS) connection, a tip, ring, ring, and sleeve (TRRS) connection, a serial peripheral interface bus (SPI) connection, a universal serial bus (USB) connection, an RS-232 serial connection, an Ethernet connection, a FireWire connection, and combinations thereof. Example 195: The system of any of examples 192-194 further comprising a gateway configured to receive the data transmitted from the coordinator, wherein the gateway transmits the data received from the coordinator through a network. Example 196: The system of example 195 wherein the network comprises one or more of a local area network (LAN), wide area network (WAN), wireless mobile telephony network, General Packet Radio Service (GPRS) network, wireless Local Area Network (WLAN), Global System for Mobile Communications (GSM) network, Personal Communication Service (PCS) network, Advanced Mobile Phone System (AMPS) network, a satellite communication network, and combinations thereof. Example 197: The system of example 195 or 196 further comprising a server coupled to the network, the server configured to receive the data from the gateway. Example 198: The system of example 197 wherein the server is configured to analyze the data and determine a metric. Example 199: The system of any of examples 192-198 wherein the device is configured to transmit the data intermittently to the coordinator. Example 200: The system of example 199 wherein the coordinator is configured to transmit the data intermittently to the gateway.

Example 201: The system of example 200 wherein the gateway transmits data intermittently via the network. Example 202: The system of any of examples 192-201 further comprising a plurality of devices. Example 203: The system of any of examples 192-202 further comprising a plurality of gateways. Example 204: The system of any of examples 192-203 wherein at least one device communicates with a first coordinator, and at least one other device communicates with a second coordinator. Example 205: The system of example 204 wherein the first coordinator is in communication with at least one gateway. Example 206: The system of example 205 wherein the first coordinator is configured to relay communications between the at least one gateway and the second coordinator. Example 207: The system of any of examples 192-206 wherein the data received from each device is analyzed by the processor. Example 208: The system of any of examples 192-207 wherein each device has an outer casing and the power source, processor and transmitter are inside the casing. Example 209: The system of any of examples 192-208 wherein each device monitors a separate medical condition of the wearer. Example 210: The system of any of examples 192-208 wherein at least one device monitors at least one medical condition of the wearer and at least one other device is used to transmit and receive non-medical information relevant to the wearer.

Example 211: The system of any of examples 192-210 wherein there is one or more devices that are collectively configured to measure a characteristic selected from the group consisting of: temperature, pressure, vibration, an electrical resistance parameter, an atmospheric condition, sound, a blood chemical, radiation, position, force, movement, and combinations thereof. Example 212: The system of any of examples 192-210 wherein each device transmits data to the coordinator at regular intervals. Example 213: The system of any of examples 192-212 wherein each device is configured to transmit data to the coordinator, and the data is analyzed to detect a condition associated with the wearer. Example 214: The system of any of examples 192-213 wherein the device further comprises a communication interface. Example 215: The system of example 214 wherein the device is configured to receive data from a computer system. Example 216: The system of any of examples 192-215 wherein the device is configured to perform a self-diagnostic to determine if it is functioning properly. Example 217: The system of any of examples 192-215 that further includes an intermediary device that performs a diagnostic on the device to determine if it is functioning properly. Example 218: The system of any of examples 216 or 217 wherein the device is configured to generate an alert in response to a determination that it is not functioning properly. Example 219: The system of any of examples 192-218 wherein one or more of each device, the coordinator, and the gateway is configured to receive and install a software update directly, or indirectly via an intermediary device, to at least one device.

Example 220: A method comprising: (a) measuring medical data of a patient via a device; (b) converting the medical data into electronic data; (c) storing the electronic data in a database; (d) establishing a communications link between a first transmitter and a first receiver; (e) establishing a communications link between a first transmitter and the database; (f) transmitting all or part of the database to the first receiver; and (g) analyzing the transmitted part of the database to monitor the medical condition of a wearer of the device. Example 221: The method of example 220 wherein the database is resident on the device. Example 222: The method of example 220 or 221 wherein the medical data is measured using one or more sensors. Example 223: The method of example 220 wherein the database is resident on a server. Example 224: The method of example 220 wherein the database is resident remote from the device. Example 225: The method of any of examples 220-224 wherein the data is continuously measured. Example 226: The method of any of examples 220-225 wherein at least part of the database comprises medical data and is analyzed to establish a standard operating parameter for the wearer. Example 227: The method of example 226 wherein more than one type of medical data is measured and analyzed. Example 228: The method of any of examples 226-227 wherein after the standard operating parameter is established, each subsequent medical data measured is compared to the standard operating parameter to determine the wearer's medical condition. Example 229: The method of example 228 wherein if an operating parameter is not met an alarm is transmitted to one or more of the devices and a medical provider. Example 230: The method of any of examples 225-229 wherein after the operating parameter is established, the medical data measured thereafter is compared to the standard operating parameter on predetermined time intervals.

Example 231: The method of example 230 wherein when medical data measured after the standard operating parameter has been established is outside of a predetermined range, an alarm is transmitted that is detectable by the wearer and/or a medical provider. Example 232: The method of any of examples 220-231 wherein the memory is constantly accessed by a controller. Example 233: The system or method of any of examples 192-232 comprising a plurality of devices attached to the wearer. Example 234: The system or method of example 233 wherein each device monitors at least one medical condition of the wearer separate from any medical condition monitored by each of the other of the plurality of devices. Example 235: The system or method of any of examples 192-232 wherein each device receives a signal from a secondary unit and transmits the signal. Example 236: The system of example 235 wherein the secondary unit is a glucose meter or another device for measuring blood chemistry. Example 237: The system or method of any of examples 192-232 wherein the device is on a wrist or the bicep, or the ankle, or the thigh, or the torso, or the neck, or the head, of the wearer. Example 238: The system or method of any of examples 192-232 wherein the device further includes a power source. Example 239: The system of example 238 wherein the device further includes a system for recharging the power source. Example 240: The system or method of any of examples 192-232 wherein at least one of the device(s) is not flexible.

Example 241: The system or method of any of examples 192-232 wherein a device is configured to measure a characteristic selected from the group consisting of: temperature, pressure, blood flow, vibration, an electrical resistance parameter, an atmospheric condition, sound, a chemical, radiation, position, force, movement, and/or combinations thereof. Example 242: The system or method of any of examples 192-232 wherein the device transmits data when commanded by the wearer. Example 243: The system or method of any of examples 192-232 that is configured to: (a) analyze the data from the device to detect a condition associated with the wearer; and (b) transmit the data to the coordinator when the condition is detected. Example 244: The system or method of example 243 wherein the detected condition is selected from the group consisting of: a possible heart attack, stroke, fainting, and/or dangerously low or high blood sugar levels. Example 245: The system or method of any of examples 192-232 wherein the device further comprises a receiver and a transmitter. Example 246: The system of example 245 wherein the device is configured to receive data from a computer system. Example 247: The system or method of any of examples 192-232 wherein the device is configured to perform a diagnostic on itself to determine whether it is functioning properly. Example 248: The system or method of any of examples 192-232 wherein the processor is configured to perform a diagnostic on the device to determine whether the device is functioning properly. Example 249: The system or method of any of examples 192-232 wherein the device is configured to generate an alert in response to a determination that the device is not functioning properly. Example 250: The system or method of any of examples 192-232 wherein one or more of the device, the coordinator, and the gateway is configured to wirelessly receive, directly or indirectly, and install a software update.

Example 251: A device for being worn by a wearer, the device being a band that wraps around either the arm, leg, foot, hand, torso, neck or head of the wearer and having one or more of the structures or functions of any of examples 1-250. Example 252: The device of example 251 that has a width of between ½" and 1", or 1" or more. Example 253: The device of example 251 or 252 that has a first side that faces outward when on a user and a second side that faces inward when on a user, a display being on the first side and/or the second side. Example 254: The device of any of examples 251-253 that has controls separate from the display and the controls are on the first side and/or the second side. Example 255: The device of either examples 253 or 254 wherein the display includes a touch screen control. Example 256: The device of any of examples 251-255 that includes an identifier that unlocks and makes useable one or more of an automobile, a cell phone, a computer, a garage door, an entry door, a security system, or other electronically configured device. Example 257: The device of example 256 wherein the identifier is an RFID code. Example 258: The device of example 256 that transmits the identifier either directly or intermittently to the electronically configured device. Example 259: The device of example 258 that uses NFC to communicate the identifier. Example 260: The device of any of examples 251-259 that includes a clock, an alarm, and a calendar.

Example 261: The device of any of examples 251-260 that includes more than one display on the first side and/or more than one display on the second side. Example 262: The device of any of examples 251-261 that has a first display related to a first function of the device and a second display related to a second function of the device. Example 263: The device of example 262 wherein the first function is monitoring, retrieving, displaying, measuring and/or transmitting medical information related to the wearer. Example 264: The device of example 262 or 263 wherein the second function is assisting the wearer with the wearer's daily routine by monitoring, measuring, displaying, retrieving, and/or transmitting personal information related to the wearer. Example 265: The device of any of examples 251-264 that can be controlled at least in part by motions of the wearer. Example 266: The device of any of examples 251-264 wherein the controls can change the display(s) to display different information and/or functions of the device. Example 267: The device of any of examples 251-266 that is configured to control one or more functions of a television set, stereo, one or more internal lights, and/or one or more external lights. Example 268: The device of any of examples 251-267 that is configured to control one or more functions of a car. Example 269: The device of any of examples 251-268 that includes a cellular phone. Example 270: The device of any of examples 251-269 that includes a walkie talkie.

Example 271: The device of any of examples 251-270 that learns a wearer's routine by hour and day based upon inputs by the wearer and/or one or more sensors in the device. Example 272: The device of any of examples 251-271 that recommends or alerts a wearer via the display(s) an activity based on the learned routine. Example 273: The device of any of examples 251-272 that has a first control related to a first function of the device and a second control related to a second function of the device. Example 274: The device of example 273 wherein the first function is monitoring, measuring, retrieving, displaying, and/or transmitting medical information related to the wearer. Example 275: The device of example 273 or 274 wherein the second function is assisting with the wearer's personal daily routine by monitoring, measuring, retrieving, displaying, and/or transmitting personal information related to the wearer.

Yet further exemplary embodiments of the invention are reflected in the following Example Set II. These examples in Example Set II may be combined with and/or utilized in connection with any and/or all of the examples in Example Set I, as appropriate.

Example 1: A device for being attached to a person, or a person's clothing, the device comprising electronic circuitry, a transmitter, software, and one or more sensors to measure a physical condition of the person. Example 2: The device of example 1 wherein the physical condition is one or more of: blood glucose level; perspiration level; heart rate; blood pressure; blood oxygen level; salinity; skin temperature; ambient air temperature; interstitial chloride levels; and the amount of a selected substance in the ambient air. Example 3: The device of example 1 wherein the device includes one or more ports into which a sensor may be connected. Example 4: The device of example 3 that includes a plurality of ports, wherein each port can be connected to a sensor, and the device can receive and transmit information received from each sensor. Example 5: The device of example 1 wherein the device can receive and transmit information measured by the one or more sensors. Example 6: The device of example 1 that has data storage software to store information received by the one or more sensors. Example 7: The device of example 4 that has data storage software to store information received by the plurality of sensors. Example 8: The device of any of examples 1-7 that includes a switch to manually change it to one of a plurality of operating modes. Example 9: The device of any of examples 1-8 that is attachable to one or more connectors, wherein each of the one or more connectors is used to connect the device to a particular body portion or a particular position on an article of clothing. Example 10: The device of example 9 wherein the operating mode of the device changes depending upon the connector to which it is attached.

Example 11: The device of any of examples 1-9 wherein the device includes a location sensor and the operating mode of the device changes based on input form the location sensor. Example 12: The device of any of examples 8, or 10-11 wherein the device measures at least one different physical condition when in one operating mode, than it measures when in any other operating mode. Example 13: The device of any of examples 8, or 10-12 wherein the device transmits at least one different physical condition when in one operating mode, than it transmits when in any other operating mode. Example 14: The device of any of examples 8, or 10-13 wherein the device transmits at least one physical condition data at different intervals, than it does when in any other operating mode. Example 15: The device of any of examples 1-14 wherein the software performs an analysis on the measured physical condition. Example 16: The device of any of examples 1-15 wherein the device remotely accesses different software to analyze different measured physical conditions. Example 17: The device of any of examples 1-16 wherein the software is not permanently resident on the device. Example 18: The device of example 16 wherein the software to analyze different measured physical conditions is remote from the device. Example 19: The device of any of examples 1-18 that includes a receiver to receive a transmission from one or more second devices, wherein at least one, or all, of the one or more second devices transmits information about a physical condition of the user. Example 20: The device of any of examples 1-19 that analyzes a plurality of measured physical conditions to determine a heath attribute of the device user.

Example 21: The device of example 20 that transmits the health attribute of the device user. Example 22: The device of any of examples 1-21 that can be attached to a band that fits around one of a user's: wrist, arm, thigh, calf, knee, ankle, head, torso, or neck. Example 23: The device of any of examples 1-22 that can be attached to a clip, pin, or other structure, that can then be attached to a user's clothing. Example 24: The device of any of examples 1-23 wherein the power source is a battery. Example 25: The device of example 24 wherein the battery is rechargeable. Example 26: The device of any of examples 1-25 that includes a thermometer to measure air temperature. Example 27: The device of any of examples 1-26 that includes a clock. Example 28: The device of any of examples 1-27 that includes a calendar. Example 29: The device of any of examples 1-28 that includes a GPS locator. Example 30: The device of any of examples 1-29 that communicates with a computer.

Example 31: The device of any of examples 1-30 that suggests a first activity on a display based on the date and time. Example 32: The device of example 31 wherein the first activity can be selected or rejected by the wearer through the use of a control. Example 33: The device of example 32 that suggests a different activity if the first activity is rejected. Example 34: The device of any of examples 31-33 wherein the wearer can select among multiple activities in which to participate. Example 35: The device of any of examples 1-34 that is connected to a database of past activities of the wearer, the database including the activity, date and time of the activity, and optionally the duration of the activity. Example 36: The device of example 35 wherein the database can be updated or changed manually by the wearer. Example 37: The device of example 35 or 36 wherein the database is updated automatically based upon activity by the wearer. Example 38: The device of any of examples 1-37 that includes an alarm to remind the wearer of an activity. Example 39: The device of example 38 wherein the alarm is one or more of an audio alarm, a visual alarm, or physical alarm. Example 40: The device of example 38 wherein the physical alarm is vibrational.

Example 41: The device of any of examples 1-40 that contacts an emergency center and provides the user's location if it senses an emergency. Example 42: The device of example 41 wherein the emergency can be one or more of (a) a sudden impact, (b) unstable or lack of heart beat, (c) unstable or lack of blood pressure, or (d) a fall. Example 43: The device of any of examples 1-42 that further accesses one or more of (a) the time of day, day of the week, day of the year, month, and/or year, (b) health information related to the user, and (c) information related to the nutritional aspects of one or more food items. Example 44: The device of example 43 wherein the one or more of (a)-(c) is stored in a memory, which is either included in the device or is separate from the device. Example 45: The device of example 43 wherein the one or more of (a)-(c) is stored in or more separate databases accessible by the device. Example 46: The device of any of examples 43-45 wherein the health information of the individual includes one or more of the wearer's weight, age, measured blood sugar level, measured blood pressure, heart condition, whether the wearer is diabetic, whether the wearer has high blood pressure, and whether the wearer is pregnant and the stage (by days or weeks) of the pregnancy. Example 47: The device of any of examples 43-46 wherein the information related to a food item includes one or more of (a) its ingredients, (b) the amount by weight of each ingredient, (c) its calories, (d) carbohydrate content, (e) vitamin content, (f) fat content, and (g) sugar content. Example 48: The device of any of examples 43-46 that compares the wearer's health information to the information related to one or more food items, and the device displays one or more suggested food items. Example 49: The device of any of examples 1-48 that adds new information and updates a database as it is used. Example 50: A device according to any of examples 1-49, the device connectable to a server having a memory, and further having at least one user interface for receiving data from the device, the memory configured to store data received by the device in a file for that user.

Example 51: A system including a server and multiple devices according to any of examples 1-50. Example 52: The system of example 51 wherein at least one of the multiple devices transmits data in a format different than the format used by at least one of the other of the devices. Example 53: The system of example 51 or 52 wherein each device for a specific user includes unique identification indicia specific to that user. Example 54: The device or system of any of examples 1-53 that further includes at least one receiving device remote from a server. Example 55: Any of the devices or systems of examples 1-54 that further includes a microphone and speaker as port of the device, or that are connectable to the device. Example 56: Any of the devices or systems of examples 1-55 that further includes an emergency signal on the device that can be activated by the user to summon help. Example 57: Any of the devices of examples 1-50 that is configured to communicate with one or more servers that contains data specific to the device user, the device being configured to receive the data via email, SMS, or other wireless communications protocol. Example 58: The device of example 57 that includes an operating system and software on the operating system that configures the device to communicate with one or more servers, or one or more other devices. Example 59: The device of example 57 or 58 wherein an alert is received when new data is displayed on the device. Example 60: The device or system of any of examples 1-59 wherein the device communicates using one or more of a NFC signal, blue tooth signal, Wi-Fi signal or Zigbee protocol.

Example 61: The device or system of any of examples 1-60 that is connectable to a separate power source. Example 62: The device or system of any of examples 1-61 that communicates directly with a wireless cellular network. Example 63: The device or system of any of examples 1-62 that further includes a docking station, the docking station for receiving a deice and transmitting information from the device to an application, server, intermediary device, or database. Example 64: The device or system of any of example 63 wherein the transmitting is done wirelessly. Example 65: The device or system of any of examples 1-64 that includes a command server, the command server for sending one or more commands to the device to activate a function of the device. Example 66: The device or system of any of examples 1-65 wherein the at least one sensor is one or more of a thermometer, a heart rate monitor, a blood oxygen sensor, an electric resistance meter, a pressure transducer, and an air quality sensor. Example 67: The device or system of any of examples 1-66 that has a wireless communication device that is configured to transmit using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network. Example 68: The system of any of examples 50-54 or 57 wherein each of the plurality of devices is configured to communicate with at least one other of the plurality of devices. Example 69: The device or system of any of examples 1-68 wherein at least one device transmits data (a) at regular intervals, (b) when requested by a central control system, (c) in the event of a predetermined value being exceeded, (d) when a sufficiently strong wireless signal is detected for transmitting the data, and/or (e) when sent by the device user.

Example 70: A method according to any system of any of examples 50-54, or 57 wherein there is a plurality of devices, the method comprising the steps of: receiving data from at least one of the plurality of devices, wherein each of the plurality of devices is in communication with a wearer, and wherein the data comprises medical or personal information about the wearer; and transmitting the medical information condition to a first server, and transmitting the personal information to a second server. Example 71: The method of example 70 wherein the plurality of devices includes one or more of a thermometer, pressure transducer, accelerometer, electric conductivity meter, perspiration sensor, heart rate sensor, blood oxygen sensor, respiration rate sensor, and a GPS device. Example 72: The method of example 70 or 71 wherein the data is provided to a monitoring unit by one or more of the plurality of devices. Example 73: The method of any of examples 70-72 wherein the medial and/or personal information is transmitted in real time. Example 74: The method of any of examples 70-72 wherein the medical and/or personal information is transmitted at predetermined times, or when an electrical communications signal sufficient for transmitting the information is detected. Example 75: The method of any of examples 70-74 wherein at least one device is configured to transmit using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network. Example 76: The device of example 19 that transmits the transmission received from the one or more second devices. Example 77: The device of example 76 that receives the transmission from the one or more second devices in a first communication format and transmits it in a second communication format. Example 78: The device of example 77 that is configured to receive transmissions in a plurality of communication formats. Example 79: The device of any of examples 1-19 or 76-78 that is configured to send transmissions in a plurality of different communication formats. Example 80: The device of example 77 wherein the second communication format is based upon a configuration of a receiving device to which the transmission is sent.

Example 81: The device of any of examples 3-7 wherein at least one of the sensors is disposable. Example 82: The device of example 81 wherein all of the sensors are disposable. Example 83: The device of any of examples 3-7 wherein the operating mode of the device changes based upon which sensor or sensors are attached to a port or ports. Example 84: The device, system, or method of any of examples 1-83 wherein the device can activate an RFID tag and read information from the RFID tag. Example 85: The device, system, or method of any of examples 1-84 wherein the RFID tag is located on or in a blood absorption strip. Example 86: The device, system, or method of example 85 wherein the information read is blood glucose level.

Yet further exemplary embodiments of the invention are reflected in the following Example Set III. These examples in Example Set III may be combined with and/or utilized in connection with any and/or all of the examples in Example Set I and/or II, as appropriate.

Example 1: A software system for improving the functioning of a wearable electronic device lacking a hardware memory management unit, the software system comprising: (a) a FLM linker that converts an executable and linkable format (ELF) file into a flash loadable module (FLM) file; and (b) an FLM loader that loads the FLM file into a flash memory of the wearable electronic device. Example 2: The software system of example 1, wherein the FLM linker collects all relevant relocation entries from all sections in the ELF file and orders them by relocation address. Example 3: The software system of example 2, wherein the FLM linker breaks a code segment of the ELF file into blocks based on a configurable block size. Example 4: The software system of example 3, wherein the FLM linker groups each block of the code segment with all relevant relocation entries pertaining to that block. Example 5: The software system of example 4, wherein the FLM linker creates an FLM file comprising: (a) an FLM header; (b) a code segment header; (c) a plurality of code blocks, each of the plurality of code blocks grouped with all relevant relocation entries for that code block; (d) a data segment header; (e) a plurality of data blocks; and (f) relevant relocation entries for each of the plurality of data blocks. Example 6: The software system of example 5, wherein the FLM loader loads the FLM file into a plurality of contiguous pages of the flash memory of the wearable electronic device. Example 7: The software system of example 6, wherein the wearable electronic device comprises an intermediate RAM buffer, and wherein the FLM loader loads the FLM file into the plurality of contiguous pages of the flash memory of the wearable electronic device via the intermediate RAM buffer. Example 8: The software system of example 6, wherein the wearable electronic device comprises a flash buffer, and wherein the FLM file code block size and the flash buffer size are identical. Example 9: The software system of example 8, wherein the FLM loader repeatedly: (a) loads a code block into the flash buffer; (b) reads the relevant relocation entries for the code block from the FLM file; (c) performs relocation as necessary on the code block in the flash buffer to form a relocated code block; and (d) writes the relocated code block to the flash memory of the wearable electronic device. Example 10: The software system of example 5, wherein the software system improves the operating of the wearable electronic device by reducing the number of write operations on the flash memory of the wearable electronic device, thus prolonging the life of the flash memory.

Example 11: The software system of example 5, wherein the software system improves the operating of the wearable electronic device by reducing the electrical power necessary for operation of the wearable electronic device, thus prolonging battery life. Example 12: The software system of example 5, wherein the software system improves the functioning of the wearable electronic device by eliminating the need for a hardware memory management unit, thus allowing the wearable electronic device to be made smaller and lighter. Example 13: The software system of example 1, whereby, via operation of the software system, the wearable electronic device is provided with a plurality of functions associated with a plurality of ELF files. Example 14: The software system of example 1, wherein the software system utilizes a first ELF file to implement a first function for the wearable electronic device, wherein the software system utilizes a second ELF file to implement a second function for the wearable electronic device, and wherein the first function and the second function are different. Example 15: The software system of example 14, whereby the first function is associated with operation of the wearable electronic device as at least one of: a blood glucose meter; a pacemaker; a blood pressure monitor; an insulin pump; a pulse oximeter; a Holter monitor; an electrocardiogram electroencephalograph; a blood alcohol monitor; an alcohol breathalyzer; an alcohol ignition interlock; a respiration monitor; an accelerometer; a skin galvanometer; a thermometer; a patient geolocation device; a scale; an intravenous flow regulator; a patient height measuring device; a biochip assay device; a monitor for biological agents; a hazardous chemical agent monitor; an ionizing radiation sensor; a sphygmomanometer; a loop recorder; a spirometer; an event monitor; a prothrombin time (PT) meter; an international normalized ratio (INR) meter; a tremor sensor; or a defibrillator. Example 16: The software system of example 14, wherein the software system is configured to receive, via communications hardware of the wearable electronic device, the second ELF file to replace the first ELF file. Example 17: The software system of example 1, wherein the software system provides, via operation of the FLM linker and the FLM loader, the ability to load binary modules freely at any location in the flash memory, regardless of the initial target address in the ELF file.

Yet further exemplary embodiments of the invention are reflected in the following Example Set IV. These examples in Example Set IV may be combined with and/or utilized in connection with any and/or all of the examples in Example Set I, II, and/or III, as appropriate.

Example 1: A flash loadable module (FLM) file for use in connection with flash memory of electronic computing devices lacking a memory management unit, the FLM file comprising: (a) an FLM header; (b) a code segment header; (c) a plurality of code blocks, each of the plurality of code blocks grouped with all relevant relocation entries for that code block; (d) a data segment header; (e) a plurality of data blocks; and (f) relevant relocation entries for each of the plurality of data blocks. Example 2: The FLM file of example 1, wherein the FLM file is created by an FLM linker from an executable and linkable format (ELF) file. Example 3: The FLM file of example 2, wherein the FLM header contains information regarding the original memory target location of the ELF file. Example 4: The FLM file of example 2, wherein the code segment header includes information regarding the segment type, location, size, and number of following code blocks. Example 5: The FLM file of example 4, wherein the size of a code block is a fixed size, and the size of all relevant relocation entries for that code block is a variable size. Example 6: The FLM file of example 5, wherein the fixed size is the size of a flash buffer for the flash memory. Example 7: The FLM file of example 4, wherein the combined size of a code block and the relevant relocation entries for that code block does not exceed a threshold size. Example 8: The FLM file of example 7, wherein the threshold size is the size of a random access memory (RAM) buffer of the electronic computing device. Example 9: The FLM file of example 2, wherein the data segment header includes information regarding the segment type, location, size, and number of following data blocks.

Example 10: The FLM file of example 1, wherein the FLM file improves the operating of the electronic computing device by reducing the number of write operations on the flash memory of the electronic computing device, thus prolonging the life of the flash memory.

Example 11: The FLM file of example 1, wherein the FLM file improves the operating of the electronic computing device by reducing the electrical power necessary for operation of the electronic computing device, thus prolonging battery life. Example 12: The FLM file of example 1, wherein the FLM file improves the functioning of the electronic computing device by eliminating the need for a hardware memory management unit, thus allowing the electronic computing device to be made smaller and lighter. Example 13: The FLM file of example 1, wherein the FLM file is created from a first ELF file to implement a first function for the electronic computing device, wherein the FLM file is created from a second ELF file to implement a second function for the electronic computing device, and wherein the first function and the second function are different. Example 14: The FLM file of example 1, wherein, when the FLM file is loaded into the flash memory of the electronic computing device, the FLM file allows the electronic computing device to function as at least one of: a blood glucose meter; a pacemaker; a blood pressure monitor; an insulin pump; a pulse oximeter; a Holter monitor; an electrocardiogram electroencephalograph; a blood alcohol monitor; an alcohol breathalyzer; an alcohol ignition interlock; a respiration monitor; an accelerometer; a skin galvanometer; a thermometer; a patient geolocation device; a scale; an intravenous flow regulator; a patient height measuring device; a biochip assay device; a monitor for biological agents; a hazardous chemical agent monitor; an ionizing radiation sensor; a sphygmomanometer; a loop recorder; a spirometer; an event monitor; a prothrombin time (PT) meter; an international normalized ratio (INR) meter; a tremor sensor; or a defibrillator. Example 15: The FLM file of example 1, wherein the FLM file is suitable for use by a first electronic computing device and a second electronic computing device, and wherein the first electronic computing device and the second electronic computing device utilize different hardware configurations. Example 16: The FLM file of example 2, wherein the FLM file provides the ability to load binary modules freely at any location in the flash memory, regardless of the initial target address in the ELF file.

Yet further exemplary embodiments of the invention are reflected in the following Example Set V. These examples in Example Set V may be combined with and/or utilized in connection with any and/or all of the examples in Example Sets I-IV, as appropriate.

Example 1: A device for being attached to a user or the user's clothing, the device comprising: (a) a band having a length, a width, and a thickness, the band including electronic circuitry, a first power source, and a display; and (b) the band, electronic circuitry, and display being flexible so as to be functional when manipulated into a circle having a diameter of 4" or more, 5" or more, 6" or more, 7" or more, 8" or more, 9" or more, or 10" or more. Example 2: The device of example 1 wherein the band has a thickness of ¼" or less. Example 3: The device of example 1 wherein the band has a width of 2" or less, or 1½" or less, or 1" or less or ¾" or less. Example 4: The device of example 1 wherein the first power source is a battery. Example 5: The device of example 4 wherein the battery is rechargeable. Example 6: The device of example 1 that further includes a second power source. Example 7: The device of example 6 wherein the second power source is a primary battery or a secondary battery. Example 8: The device of claim 1 wherein the circuitry has a length that is 50% or less of the length of the band, or 80% or less the length of the band. Example 9: The device of example 1 wherein the circuitry has a thickness of 25% or less of the thickness of the band, or 25%-50% of the thickness of the band, or 75% of the thickness of the band. Example 10: The device of example 1 wherein the circuitry has a width of 90% or less of the width of the band, or between 50% and 80% of the width of the band, or between 80% and 100% of the width of the band.

Example 11: The device of example 1 wherein the display has a length that is 50% or less of the length of the band, or 80% or less of the length of the band. Example 12: The device of example 1 wherein the display has a thickness that is 25% or less of the thickness of the band, or 25%-50% of the thickness of the band, or 80% or less of the thickness of the band. Example 13: The device of example 1 wherein the display has a width of 90% or less of the width of the band, or between 50% and 80% of the width of the band, or between 90%-100% of the width of the band. Example 14: The device of example 1 that is configured to measure one or more of the group consisting of a user's: heart rate, blood oxygen, perspiration, electrical resistance on the skin, blood pressure, and skin temperature. Example 15: The device of example 1 that further includes one or more of the group consisting of: a clock, a calendar, and a GPS locator. Example 16: The device of example 1 that further includes a touch screen, the touch screen displaying commands to assist in controlling the device. Example 17: The device of example 1 that is configured to show a first activity on the display based on the date and time. Example 18: The device of example 17 that is configured to show a different activity if the first activity is rejected. Example 19: The device of example 1 that is configured to permit a user to select among multiple activities in which to participate. Example 20: The device of example 1 that is configured to communicate with a database of past activities of the user, the database including the activity, and date and time the user participated in the activity.

Example 21: The device of example 20 wherein the database can be updated or changed manually by the user. Example 22: The device of example 20 wherein the database is updated automatically based upon activity by the user. Example 23: The device of example 1 that in configured to activate one or more of a user's apparatuses when the device is within a predetermined proximity of the apparatus, the apparatus consisting of the group selected from: (a) home gate code, (b) a development gate code, (c) automobile ignition, (d) a garage door, (e) a cellular phone, (f) a computer, (g) an entrance door, (h) a television set, (i) a television set control, and (j) a security alarm. Example 24: The device of example 1 that can withstand an impact force of 5 lbs or more, or 10 lbs or more, or between 20 lbs and 25 lbs, or between 20 lbs and 30 lbs.

Yet further exemplary embodiments of the invention are reflected in the following Example Set VI. These examples in Example Set VI may be combined with and/or utilized in connection with any and/or all of the examples in Example Sets I-V, as appropriate.

Example 1: A device for being attached to a user or the user's clothing, the device having a length, a width, and a thickness, the device comprising: (a) electronic circuitry, a first power source, and a display; (b) a thickness of ¼" or less; and (c) the device being configured to communicate with and receive data from one or more medical devices. Example 2: The device of example 1 that has a width of 2"

or less, or 1½" or less, or 1" or less or ¾" or less. Example 3: The device of example 1 wherein the first power source is a battery. Example 4: The device of example 1 wherein the circuitry has a length that is 50% or less of the length of the device, or 80% or less of the length of the device. Example 5: The device of example 1 wherein the circuitry has a thickness of 25% or less of the thickness of the device, or 25%-50% of the thickness of the thickness of the device, or 75% or less of the thickness of the device. Example 6: The device of example 1 wherein the circuitry has a width of 90% or less of the width of the device, or between 50% and 80% of the width of the device, or between 80% and 100% the width of the device. Example 7: The device of example 1 wherein the display has a length that is 50% or less of the length of the device, or 80% or less of the length of the device. Example 8: The device of example 1 that is configured to monitor one or more physical conditions of the user. Example 9: The device of example 1 that is configured to analyze a plurality of the one or more physical conditions of the user to determine a health attribute of the user. Example 10: The device of example 1 that includes one or more ports, wherein each of the one or more ports can be connected to a sensor, and the device is configured to receive information from at least one sensor.

Example 11: The device of example 10 that has a plurality of ports. Example 12: The device of example 11 that has a plurality of sensors, wherein each of the plurality of sensors is connected to a port. Example 13: The device of example 10 that has a plurality of operating modes, and the operating mode of the device changes depending upon one or more of the sensors attached to the device. Example 14: The device of example 12 that has a plurality of operating modes, and the operating mode of the device changes upon one or more of the sensors attached to the device. Example 15: The device of example 1 wherein data is received by the device from the medical device through a connection that is selected from the group consisting of an optical fiber connection, a tip and sleeve (TS) connection, a tip, ring, and sleeve (TRS) connection, a tip, ring, ring, and sleeve (TRRS) connection, a serial peripheral interface bus (SPI) connection, a universal serial bus (USB) connection, an RS-232 serial connection, an Ethernet connection, a Fire-Wire connection, and combinations thereof. Example 16: The device of example 1 wherein data is received by the device from the medical device wirelessly using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network. Example 17: The device of example 1 wherein the medical device comprises one or more of: a blood glucose meter; a pacemaker; a blood pressure monitor; an insulin pump; a pulse oximeter; a Holter monitor; an electrocardiograph; an electroencephalograph; a blood alcohol monitor; an alcohol breathalyzer; an alcohol ignition interlock; a respiration monitor; an accelerometer; a skin galvanometer; a thermometer; a patient geolocation device; a scale; an intravenous flow regulator; a patient height measuring device; a biochip assay device; a monitor for biological agents; a hazardous chemical agent monitor; an ionizing radiation sensor; a sphygmomanometer; a loop recorder; a spirometer; an event monitor; a prothrombin time (PT) meter; an international normalized ratio (INR) meter; a tremor sensor; a defibrillator. Example 18: The device of example 1 that is configured to transmit at least some of the data received from the medical device. Example 19: The device of example 18 wherein the data received and transmitted includes one of a battery charge level, a temperature, a barometric pressure, a code relating to an accessory for the medical device, a data validity measurement, an elapsed time since a previous reading by the medical device, a test result parameter, a signal-to-noise parameter, a quality of service (QoS) parameter; and a user's: heart rate, blood oxygen level, perspiration, electrical resistance on the skin, movement, blood pressure, fall or sudden impact, calories used, calories consumed, body temperature; and ambient air temperature, time, day, and location. Example 20: The device of example 1 that is configured to communicate with a plurality of medical devices.

Example 21: The device of example 1 that is configured to communicate simultaneously with a plurality of medical devices. Example 22: The device of example 1 wherein its functionality changes depending upon the medical device with which the device communicates. Example 23: The device of example 1 that is configured to also communicate with an intermediary device, or a central server. Example 24: The device of example 1 that is configured to receive data from an apparatus implanted in a user of the device. Example 25: The device of example 18 that is configured to transmit or receive a user's health information. Example 26: The device of example 25 that is configured to analyze the user's health information to identify a condition for the user. Example 27: The device of example 26 that is configured to alert the user or a health care professional when the user condition satisfies a predetermined threshold condition. Example 28: The device of example 1 that is configured to analyze one or more medications taken by the patient and determines whether the patient is in compliance with a prescribed medical treatment. Example 29: The device of example 28 that is configured to determine whether a medication of one or more medications taken by a patient may interact with one or more of: a second medication of the one or more medications taken by the patient; a newly prescribed medication; an over-the-counter medication; an herbal supplement; a vitamin; and a food or a beverage. Example 30: The device of example 1 wherein the electronic circuitry and display are flexible so as to be functional when manipulated into a circle having a diameter of 4" or more, 5" or more, 6" or more, 7" or more, 8" or more, 9" or more, or 10" or more.

Yet further exemplary embodiments of the invention are reflected in the following Example Set VII. These examples in Example Set VII may be combined with and/or utilized in connection with any and/or all of the examples in Example Sets I-VI, as appropriate.

Example 1: A device for being attached to a user or the user's clothing, the device having a length, a width, and a thickness, the device comprising: electronic circuitry, a first power source, and a display; wherein the device, electronic circuitry, and display are flexible so as to be functional when manipulated into a circle having a diameter of 4" or more, 5" or more, 6" or more, 7" or more, 8" or more, 9" or more, or 10" or more. Example 2: The device of example 1 that has a thickness of ¼" or less. Example 3: The device of example 1 that has a width of 2" or less, or 1½" or less, or 1" or less or ¾" or less. Example 4: The device of example 1 wherein the power source is a battery. Example 5: The device of example 1 wherein the circuitry has a length that is 50% or less of the length of the device, or 80% or less than the length of the device. Example 6: The device of example 1 wherein the circuitry has a thickness of 25% or less of the thickness of the device, or 25%-50% of the thickness of the device, or 75% or less of the thickness of the device. Example 7: The device of example 1 wherein the circuitry has a width of 90% or less of the width of the device, or between 50% and 80% of the width of the device, or between 80% and 100% of the width of the device. Example 8: The device of example 1 wherein the display has a length that is 50% or less of the length of the device, or 80% or less of the length of the device. Example 9: The device of example 1 that communicates using one or more of: a cell phone, computer, wifi, or other short-range communication protocol. Example 10: The device of example 1 that communicates wirelessly and is configured to transmit using at least one of a satellite communication network, a local area network (LAN), a wide area network (WAN), a wireless mobile telephone network, a General Packet Radio Service (GPRS) network, a wireless local area network (WLAN), a Global System for Mobile Communications (GSM) network, a Personal Communication Service (PCS) network, and an Advanced Mobile Phone System (AMPS) network.

Example 11: The device of example 1 that is configured to transmit data when a short-range transmission signal sufficient to transmit the data is detected. Example 12: The device of example 1 that is configured to transmit or receive data (a) on regular intervals, (b) when requested by a central control system, (c) in the event of a predetermined value being exceeded, (d) when a sufficiently strong wireless signal is determined for transmitting the data, and/or (e) when sent by the device user. Example 13: The device of example 1 that is configured to receive data (a) on regular intervals, (b) when requested by a central control system, (c) in the event of a predetermined value being exceeded, (d) when a sufficiently strong wireless signal is determined for receiving the data, and/or (e) when sent by the device user. Example 14: The device of example 1 that is configured to transmit data using: a Zigbee protocol, a Wibree protocol, an IEEE 802.11 protocol, an IEEE 802.15 protocol, an IEEE 802.16 protocol, an Ultra-Wideband (UWB) protocol, an Infrared Data Association (IrDA) protocol, a Bluetooth protocol, and combinations thereof. Example 15: The device of example 1 that is configured to transmit data through a wired connection selected from the group consisting of: an optical fiber connection, a tip and sleeve (TS) connection, a tip, ring, and sleeve (TRS) connection, a tip, ring, ring, and sleeve (TRRS) connection, a serial peripheral interface bus (SPI) connection, a universal serial bus (USB) connection, an RS-232 serial connection, an Ethernet connection, a FireWire connection, and combinations thereof. Example 16: The device of example 12 in which the transmitted data is encrypted. Example 17: The device of example 13 in which the received data is encrypted. Example 18: The device of example 12 wherein the data is encrypted using at least one encryption key comprising: a private encryption key associated with the patient; a private encryption key of a health care provider associated with the patient; a public encryption key associated with at least one of: an intended recipient, a medical data server; or combinations thereof. Example 19: The device of example 1 that is configured to transmit or receive data in a frequency range comprising at least one of the medical implant communications service (MICS) frequency band, the frequency range of 402 MHz to 405 MHZ, the Wireless Medical Telemetry Service (WMTS) frequency band, the frequency range of 608 MHz to 614 MHZ, the frequency range of 1395 MHz to 1400 MHZ, the frequency range of 1427 MHz to 1432 MHz, the frequency range 32 KHz to 175 KHz, and combinations thereof. Example 20: The device of example 1 that is configured to transmit or receive data using a wireless connection, a wired connection, or both. Example 21: The device of example 1 that is configured to be authenticated before communicating with a network.

Yet further exemplary embodiments of the invention are reflected in the following Example Set VIII. These examples in Example Set VIII may be combined with and/or utilized in connection with any and/or all of the examples in Example Sets I-VII, as appropriate.

Example 1: A device for being attached to a user or the user's clothing, the device having a length, a width, and a thickness, the device comprising: electronic circuitry, a first power source, and a display; and being configured to receive data and transmit the data to a medical device after reformatting the data into a format compatible for the medical device. Example 2: The device of example 1 that has a thickness of ¼" or less. Example 3: The device of example 1 that has a width of 2" or less, or 1½" or less, or 1" or less or ¾" or less. Example 4: The device of example 1 wherein the power source is a battery. Example 5: The device of example 1 wherein the circuitry has a length that is 50% or less of the length of the device, or 80% or less of the length of the device. Example 6: The device of example 1 wherein the circuitry has a thickness of 25% or less of the thickness of the device, or 25%-50% of the thickness of the device, or 75% or less than the thickness of the device. Example 7: The device of example 1 wherein the circuitry has a width of 90% or less of the width of the device, or between 50% and 80% of the width of the device, or between 80% and 100% of the width of the device. Example 8: The device of example 1 wherein the display has a length that is 50% or less of the length of the device, or 80% or less of the length of the device. Example 9: The device of example 1 that is configured to receive data in one or more transmission protocols and/or frequencies and transmit the data in one or more different transmission protocols and/or frequencies. Example 10: The device of example 1 that is configured to receive data from a plurality of medical devices.

Example 11: The device of example 9 that is configured to receive data from a plurality of medical devices. Example 12: The device of example 9 that is configured to simultaneously receive data from a plurality of medical devices. Example 13: The device of example 1 that is configured to receive data from a plurality of medical devices, wherein at least one of the plurality of medical devices transmits data using a different transmission protocol or frequency than the protocol or frequency used by each of the other of the plurality of medical devices. Example 14: The device of example 10 wherein the medical device comprises at least one of a blood glucose meter; a pacemaker; a blood pressure monitor; an insulin pump; a pulse oximeter; a Holter monitor; an electrocardiograph; an electroencephalograph; a blood alcohol monitor; an alcohol breathalyzer; an alcohol ignition interlock; a respiration monitor; an accelerometer; a skin galvanometer; a thermometer; a patient geolocation device; a scale; an intravenous flow regulator; a patient height measuring device; a biochip assay device; a monitor for biological agents; a hazardous chemical agent monitor; an ionizing radiation sensor; a sphygmomanometer; a loop recorder; a spirometer; an event monitor; a prothrombin time (PT) meter; an international normalized ratio (INR) meter; a tremor sensor; and a defibrillator. Example 15: The device of example 1 wherein the data transmitted includes at least one of a battery charge level, a temperature, a barometric pressure, a code relating to an accessory for the medical device, a data validity measurement, an elapsed time since a previous reading by the medical device, a test result parameter, a signal-to-noise parameter, and a quality of service (QoS) parameter; and a user's: heart rate, blood oxygen level, perspiration, electrical resistance on the skin, movement, blood pressure, fall or sudden impact, calories used, calories consumed, body temperature; and ambient air temperature, time, day, and location. Example 16: The device of example 1 wherein the data transmitted by the device is encrypted. Example 17: The device of example 15 wherein data is encrypted utilizing a key comprising at least one of a private encryption key associated with the user; a private encryption key of a health care provider or merchant; an encryption key associated with a medical data server; and combinations thereof. Example 18: The device of example 1 that is configured to contact an emergency center and provide a user's location if the device senses an emergency. Example 19: The device of example 17 wherein the emergency is one or more of (a) a sudden impact, (b) unstable or lack of heart beat, (c) unstable or lack of blood pressure, (d) undesirable physical location, (e) improper glucose reading, (f) medication overdose or incompatibility, and (g) transmission by a user of an emergency. Example 20: The device of example 1 that is configured to communicate with an intermediary device that performs a diagnostic on the device to determine if the device is functioning properly.

Example 21: The device of example 1 that is configured to perform a diagnostic on itself to determine whether it is functioning properly. Example 22: The device of example 20 that is configured to generate an alert in response to a determination that it is not functioning properly. Example 23: The device of example 1 wherein one or more of the device, an intermediary device, a coordinator, and a gateway is configured to receive and install a software update directly, or indirectly, on the device. Example 24: The device of example 22 wherein the software update is installed automatically. Example 25: The device of example 22 wherein the software update is installed upon acceptance by the user. Example 26: The device of example 22 wherein the software update is installed automatically based upon the user's location. Example 27: The device of example 20 wherein the software update is installed automatically based upon the current function of the device. Example 28: The device of example 1 wherein the electronic circuitry and display are flexible so as to be functional when manipulated into a circle having a diameter of 4" or more, 5" or more, 6" or more, 7" or more, 8" or more, 9" or more, or 10" or more.

Functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Systems, methods and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one," unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. The disclosure includes a system and method, and it is contemplated that it may be embodied as computer program instructions on a tangible computer-readable carrier, such as a magnetic or optical memory or a magnetic or optical disk. All structural, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims.

What is claimed is:

1. An article of manufacture including a tangible, non-transitory computer-readable storage medium having instructions stored thereon that, in response to execution by a processor of a device attached to a user or the user's clothing, cause the device to perform operations comprising:

communicating with and receiving data from one or more medical devices comprising a plurality of alcohol monitoring devices; and changing, by the device, functionality of the device depending upon the one or more medical devices with which the device communicates, wherein the device has a length, a width, and a thickness, wherein the device comprises:

electronic circuitry, a first power source, and a display; and a thickness of 2" or less, wherein the electronic circuitry has a thickness of 25% or less of the thickness of the device, or 25%-50% of the thickness of the device, or 75% or less of the thickness of the device, and wherein the functionality of the device comprises locking doors of a vehicle and unlocking doors of the vehicle when a measured input to at least one of the plurality of alcohol monitoring devices falls below or exceeds a predetermined threshold.

2. The article of manufacture of claim 1, wherein the device has a width of 1 1/2" or less, or 1" or less or ¾" or less.

3. The article of manufacture of claim 1, wherein the electronic circuitry has a length that is 50% or less of the length of the device, or 80% or less of the length of the device.

4. The article of manufacture of claim 1, wherein the electronic circuitry has a width of 90% or less of the width of the device, or between 50% and 80% of the width of the device, or between 80% and 100% the width of the device.

5. The article of manufacture of claim 1, wherein the display has a length that is 50% or less of the length of the device, or 80% or less of the length of the device.

6. The article of manufacture of claim 1, wherein the device monitors one or more physical conditions of the user.

7. The article of manufacture of claim 6, wherein the device analyzes a plurality of the one or more physical conditions of the user to determine a health attribute of the user.

8. The article of manufacture of claim 1, wherein the device includes one or more ports, wherein each of the one or more ports can be connected to a sensor, and wherein the device receives information from at least one sensor.

9. The article of manufacture of claim 8, wherein the device has a plurality of ports.

10. The article of manufacture of claim 9, wherein the device has a plurality of sensors, and wherein each of the plurality of sensors is connected to a port.

11. The article of manufacture of claim 10, wherein the device has a plurality of operating modes, and wherein the functionality of the device changes depending upon one or more of the plurality of sensors attached to the device.

12. The article of manufacture of claim 1, wherein the data is received by the device from the one or more medical devices through a connection comprising at least one of an optical fiber connection, a tip and sleeve (TS) connection, a tip, ring, and sleeve (TRS) connection, a tip, ring, ring, and sleeve (TRRS) connection, a serial peripheral interface bus (SPI) connection, a universal serial bus (USB) connection, an RS-232 serial connection, an Ethernet connection, a FireWire connection, or combinations thereof.

13. The article of manufacture of claim 1, wherein the device transmits at least some of the data received from the one or more medical devices.

14. The article of manufacture of claim 13, wherein the data received and transmitted includes:

a. at least one of a battery charge level, a temperature, a barometric pressure, a code relating to an accessory for the one or more medical devices, a data validity measurement, an elapsed time since a previous reading by the one or more medical devices, a test result parameter, a signal-to-noise parameter, or a quality of service (QOS) parameter;

b. at least one of the user's: heart rate, blood oxygen level, perspiration, electrical resistance on skin of the user, movement, blood pressure, fall or sudden impact, calories used, calories consumed, or body temperature; and c. at least one of ambient air temperature, time, day, or location.

15. The article of manufacture of claim 1, wherein the device communicates simultaneously with a plurality of medical devices.

16. The article of manufacture of claim 1, wherein the device also communicates with an intermediary device or a central server.

17. The article of manufacture of claim 1, wherein the device analyzes the user's health information to identify a condition for the user and wherein the device alerts the user or a health care professional when the user condition satisfies a predetermined threshold condition.

18. The article of manufacture of claim 1, wherein the device analyzes one or more medications taken by the user and determines whether the user is in compliance with a prescribed medical treatment.

19. The article of manufacture of claim 1, wherein the plurality of alcohol monitoring devices a blood alcohol monitor; an alcohol breathalyzer; and an alcohol ignition interlock.

20. The article of manufacture of claim 1, wherein the functionality of the device further comprises providing driver identification, providing driver warnings, and integrating with a vehicle navigation system when the measured input to at least one of the plurality of alcohol monitoring devices falls below or exceeds a predetermined threshold.

* * * * *